United States Patent
Salituro et al.

(10) Patent No.: US 11,279,730 B2
(45) Date of Patent: Mar. 22, 2022

(54) OXYSTEROLS AND METHODS OF USE THEREOF

(71) Applicant: Sage Therapeutics, Inc., Cambridge, MA (US)

(72) Inventors: Francesco G. Salituro, Marlborough, MA (US); Albert Jean Robichaud, Boston, MA (US); Gabriel Martinez Botella, Wayland, MA (US); Boyd L. Harrison, Princeton Junction, NJ (US); Andrew Griffin, L'lle Bizard (CA); Daniel La, Chestnut Hill, MA (US)

(73) Assignee: SAGE THERAPEUTICS, INC., Cambridge, MA (US)

(*) Notice: Subject to any disclaimer, the term of this patent is extended or adjusted under 35 U.S.C. 154(b) by 0 days.

(21) Appl. No.: 16/943,649

(22) Filed: Jul. 30, 2020

(65) Prior Publication Data

US 2021/0147468 A1 May 20, 2021

Related U.S. Application Data

(62) Division of application No. 16/315,250, filed as application No. PCT/US2017/041199 on Jul. 7, 2017, now Pat. No. 10,781,231.

(60) Provisional application No. 62/359,532, filed on Jul. 7, 2016.

(51) Int. Cl.
   *C07J 9/00* (2006.01)
(52) U.S. Cl.
   CPC ..................... *C07J 9/00* (2013.01)
(58) Field of Classification Search
   CPC ........................................................ C07J 9/00
   USPC ........................................................ 514/178
   See application file for complete search history.

(56) References Cited

U.S. PATENT DOCUMENTS

| | | | |
|---|---|---|---|
| 2,594,323 A | 4/1952 | Levin et al. |
| 2,673,206 A | 3/1954 | Ryer |
| 3,079,385 A | 2/1963 | Bertin et al. |
| 3,206,459 A | 9/1965 | Cross |
| 4,071,625 A | 1/1978 | Grunwell et al. |
| 4,174,345 A | 11/1979 | Kaiser |
| 4,183,852 A | 1/1980 | Kaiser |
| 4,868,165 A | 9/1989 | Ikekawa |
| 5,232,917 A | 8/1993 | Bolger et al. |
| 5,376,645 A | 12/1994 | Stella et al. |
| 5,512,570 A | 4/1996 | Dorn et al. |
| 5,595,996 A | 1/1997 | Graham et al. |
| 5,888,996 A | 3/1999 | Farb |
| 5,925,630 A | 7/1999 | Upasani et al. |
| 6,407,086 B2 | 6/2002 | Faarup et al. |
| 6,645,953 B2 | 11/2003 | Gronvald et al. |
| 6,884,796 B2 | 4/2005 | Faarup et al. |
| 6,933,312 B2 | 8/2005 | Price et al. |
| 8,034,798 B2 | 10/2011 | Baulieu et al. |
| 8,247,436 B2 | 8/2012 | Baettig et al. |
| 8,604,011 B2 | 12/2013 | Mellon |
| 8,673,843 B2 | 3/2014 | Moskal et al. |
| 8,829,213 B2 | 9/2014 | Peng et al. |
| 10,201,550 B2 | 2/2019 | Salituro et al. |
| 10,227,375 B2 | 3/2019 | Botella et al. |
| 10,259,840 B2 | 4/2019 | Harrison et al. |
| 10,696,712 B2 | 6/2020 | Salituro et al. |
| 10,723,758 B2 | 7/2020 | Harrison et al. |
| 2004/0048838 A1 | 3/2004 | Gronvald et al. |
| 2005/0101573 A1 | 5/2005 | Faarup et al. |
| 2006/0199790 A1 | 9/2006 | Baulieu et al. |
| 2008/0193423 A1 | 8/2008 | Brunton et al. |
| 2008/0269183 A1 | 10/2008 | Mellon et al. |
| 2008/0319026 A1 | 12/2008 | Gant et al. |

(Continued)

FOREIGN PATENT DOCUMENTS

| AU | 728843 | 1/2001 |
|---|---|---|
| CN | 1257077 | 6/2000 |

(Continued)

OTHER PUBLICATIONS

Bjorkhem et al., "Oxysterols in the circulation of patients with the Smith-Lemli-Opitz syndrome: abnormal levels of 24S- and 27-hydroxycholesterol," Journal of Lipid Research, 42(3):366-371 (2001).

Bukelis et al., "Smith-Lemli-Opitz syndrome and autism spectrum disorder," American Journal of Psychiatry, 164(11):1655-1661 (2007).

Cancer [online], [retrieved on Jul. 6, 2007]. Retrieved from the internet, URL http://www.nlm.nih.gov/medlineplus/ cancer.html> (11 pages).

Chen et al., "The chemical biology of clinically tolerated NMDA receptor antagonists," Journal of Neurochemistry, 97(6):1611-1626 (2006).

(Continued)

*Primary Examiner* — Kristin A Vajda
(74) *Attorney, Agent, or Firm* — Haley Guiliano LLP; Karen Mangasarian

(57) ABSTRACT

Compounds are provided according to Formula (I): and pharmaceutically acceptable salts thereof, and pharmaceutical compositions thereof; wherein $R^1$, $R^2$, $R^3$ and $R^6$, $R^{11a}$, and $R^{11b}$ are as defined herein. Compounds of the present invention are contemplated useful for the prevention and treatment of a variety of conditions.

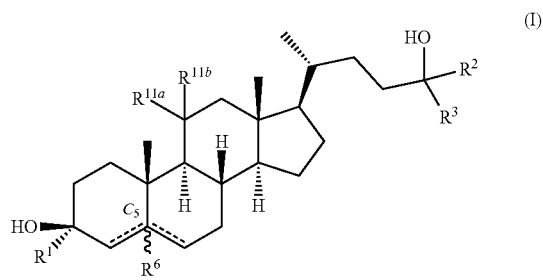

13 Claims, No Drawings

(56) References Cited

U.S. PATENT DOCUMENTS

| | | |
|---|---|---|
| 2010/0034781 A1 | 2/2010 | Parhami et al. |
| 2010/0087411 A1 | 4/2010 | Barraclough et al. |
| 2011/0160223 A1 | 6/2011 | Dingledine et al. |
| 2011/0190249 A1 | 8/2011 | Rees et al. |
| 2012/0035156 A1 | 2/2012 | Alberati et al. |
| 2012/0040916 A1 | 2/2012 | Moon et al. |
| 2012/0041016 A1 | 2/2012 | Frincke |
| 2012/0115169 A1 | 5/2012 | Mullenix et al. |
| 2013/0210792 A1 | 8/2013 | Song et al. |
| 2014/0045943 A1 | 2/2014 | Khan et al. |
| 2014/0148412 A1 | 5/2014 | Hogenkamp |
| 2014/0235600 A1 | 8/2014 | Covey et al. |
| 2014/0335050 A1 | 11/2014 | Haggerty et al. |
| 2015/0158903 A1 | 6/2015 | Upasani |
| 2015/0291654 A1 | 10/2015 | Upasani et al. |
| 2015/0376225 A1 | 12/2015 | Dugar et al. |
| 2016/0022701 A1 | 1/2016 | Reddy et al. |
| 2016/0031930 A1 | 2/2016 | Botella et al. |
| 2017/0247405 A1 | 8/2017 | Harrison et al. |
| 2017/0304321 A1 | 10/2017 | Quirk et al. |
| 2017/0305960 A1 | 10/2017 | Botella et al. |
| 2018/0194797 A1 | 7/2018 | Salituro et al. |
| 2018/0200267 A1 | 7/2018 | Salituro et al. |
| 2018/0201643 A1 | 7/2018 | Salituro et al. |
| 2018/0237470 A1 | 8/2018 | Botella et al. |
| 2018/0362573 A1 | 12/2018 | Upasani et al. |
| 2018/0371009 A1 | 12/2018 | Pellicciari et al. |
| 2019/0125764 A1 | 5/2019 | Salituro et al. |
| 2019/0127414 A1 | 5/2019 | Botella et al. |
| 2019/0135854 A1 | 5/2019 | Harrison et al. |
| 2019/0160078 A1 | 5/2019 | Masuoka et al. |
| 2019/0248829 A1 | 8/2019 | Salituro et al. |
| 2019/0330259 A1 | 10/2019 | Robichaud et al. |
| 2019/0359646 A1 | 11/2019 | Botella et al. |
| 2020/0002371 A1 | 1/2020 | Salituro et al. |
| 2020/0024300 A1 | 1/2020 | Salituro et al. |
| 2020/0123195 A1 | 4/2020 | Salituro et al. |

FOREIGN PATENT DOCUMENTS

| | | |
|---|---|---|
| CN | 1254716 | 5/2008 |
| FR | 2850023 | 7/2004 |
| GB | 1564806 | 4/1980 |
| JP | 50140435 | 11/1975 |
| JP | 53082766 | 7/1978 |
| JP | 54163565 | 12/1979 |
| JP | 57035597 | 2/1982 |
| JP | 61254599 | 11/1986 |
| JP | 62187485 | 8/1987 |
| JP | 08268917 | 10/1996 |
| JP | 09328498 | 12/1997 |
| JP | H11509844 A | 8/1999 |
| JP | 2005508368 | 3/2005 |
| RU | 2194712 | 12/2002 |
| WO | WO1980002562 | 11/1980 |
| WO | WO1994027608 | 12/1994 |
| WO | WO1995002409 | 1/1995 |
| WO | WO1995013287 | 5/1995 |
| WO | WO1995021617 | 8/1995 |
| WO | WO1996012705 | 5/1996 |
| WO | WO1996040043 | 12/1996 |
| WO | WO1997000884 | 1/1997 |
| WO | WO1997042215 | 11/1997 |
| WO | WO1998007740 | 2/1998 |
| WO | WO1999058497 | 11/1999 |
| WO | WO2000063228 | 10/2000 |
| WO | WO2000068246 | 11/2000 |
| WO | WO2001049703 | 7/2001 |
| WO | WO2002011708 | 2/2002 |
| WO | WO2002053577 | 7/2002 |
| WO | WO2002079221 | 10/2002 |
| WO | WO2003039480 | 5/2003 |
| WO | WO2003049685 | 6/2003 |
| WO | WO2003082893 | 10/2003 |
| WO | WO2004055201 | 7/2004 |
| WO | WO2005079810 | 9/2005 |
| WO | WO2008041003 | 4/2008 |
| WO | WO2009001097 | 12/2008 |
| WO | WO2009059961 | 5/2009 |
| WO | WO2009073186 | 6/2009 |
| WO | WO2009090063 | 7/2009 |
| WO | WO2010075282 | 7/2010 |
| WO | WO2010088414 | 8/2010 |
| WO | WO2011014661 | 2/2011 |
| WO | WO2011028794 | 3/2011 |
| WO | WO2011067501 | 6/2011 |
| WO | WO2011092127 | 8/2011 |
| WO | WO2012064501 | 5/2012 |
| WO | WO2012142039 | 10/2012 |
| WO | WO2013019711 | 2/2013 |
| WO | WO2013036835 | 3/2013 |
| WO | WO2013056181 | 4/2013 |
| WO | WO2013163455 | 10/2013 |
| WO | WO2014115167 | 7/2014 |
| WO | WO2014120786 | 8/2014 |
| WO | WO2014160441 | 10/2014 |
| WO | WO2014160480 | 10/2014 |
| WO | WO2015195967 | 12/2015 |
| WO | WO2016007762 | 1/2016 |
| WO | WO2016057713 | 4/2016 |
| WO | WO2017007832 | 1/2017 |
| WO | WO2017007836 | 1/2017 |
| WO | WO2017007840 | 1/2017 |
| WO | WO2017037465 | 3/2017 |
| WO | WO2018170336 | 9/2018 |

OTHER PUBLICATIONS

Citraro et al., "Effects of some neurosteroids injected into some brain areas of WAG/Rij rats, an animal model of generalized absence epilepsy," Neuropharmacology, 50(8):1059-1071 (2006).

Collingridge et al., "The NMDA receptor as a target for cognitive enhancement," Neuropharmacology, 64:13-26 (2013).

Connick et al., "Program No. 613 1/B86," 2009 Neuroscience Meeting Planner, Chicago, IL: Society for Neuroscience (2009) (2 pages).

Cook et al., "24-hydroxycholesterol sulfation by human cytosolic sulfotransferases: formation of monosulfates and disulfates, molecular modeling, sulfatase sensitivity, and inhibition of liver X receptor activation," Drug Metabolism and Disposition, 37(10):2069-2078 (2009).

Corman et al., "Structure-activity relationships for side chain oxysterol agonists of the hedgehog signaling pathway," ACS Medicinal Chemistry Letters, 3(10):828-833 (2012).

Cross et al., "Steroids CCLXXIN[1]. Biologically-active labile ethers IV[2]. The synthesis of 22-oxa-25-azacholesterol and related compounds," Steroids, 5(5):585-598 (1965).

Dayal et al., "Stereospecific synthesis of 3 beta-hydroxylated bile alcohols," Journal of Lipid Research, 25(6):646-650 (1984).

Deng et al., "Fluoro analogs of bioactive oxy-steroids: Synthesis of an $EBI_2$ agonist with enhanced metabolic stability," Bioorganic and Medicinal Chemistry Letters, 26(2):4888-4891 (2016).

Domasio, "Alzheimer's disease and related dementias," Cecil Textbook of Medicine, 20th edition, 2:1992-1996 (1996).

Elbarbry et al., "Cyclosporine-induced changes in drug metabolizing enzymes in hyperlipemic rabbit kidneys could explain its toxicity," Xenobiotica, 40(11):772-781 (2010).

European Search Partial Supplementary Report for European Application No. 14775126.7, dated Sep. 14, 2016 (7 pages).

Extended European Search Report for Application No. 15809462.3, dated Nov. 29, 2017 (8 pages).

Extended European Search Report for Application No. 16821920.2, dated Jan. 31, 2019 (12 pages).

Extended European Search Report for Application No. 16821924.4, dated Jan. 31, 2019 (12 pages).

Extended European Search Report for Application No. 16821926.9, dated Jan. 31, 2019 (10 pages).

Extended European Search Report for European Application No. 14774060.9, dated Aug. 17, 2016 (11 pages).

(56) References Cited

OTHER PUBLICATIONS

Extended European Search Report for European Application No. 14775126.7, dated Dec. 15, 2016 (6 pages).
Extended European Search Report for European Application No. 15849514.3, dated May 23, 2018 (7 pages).
FDA mulls drug to slow late-stage Alzheimer's [online] (cnn.com/health), [retrieved on Sep. 23, 2003]. Retrieved from the Internet, URL; http://www.cnn.com/2003/HEALTH/conditions/09/24/alzheimers.drug.ap/indexhtml> (2 pages).
Festa et al., "Exploitation of cholane scaffold for the discovery of potent and selective farnesoid X receptor (FXR) and G-protein coupled bile acid receptor 1 (GP-BAR$_1$) ligands," Journal of Medicinal Chemistry, 57(20):8477-8495 (2014).
Foster et al., "Effect of steroids on beta-adrenoceptor-mediated relaxation of pig bronchus," British Journal of Pharmacology, 78(2):441-445 (1983).
Golub et al., "Molecular classification of cancer: class discovery and class prediction by gene expression monitoring," Science, 286(5439):531-537 (1999).
Gunatilaka et al., "Bioactive ergost-5-ene-3 beta, 7 alpha-diol derivatives from *Pseudobersama mossambicensis*," Journal of Natural Products, 55(11):1648-1654 (1992).
Hoffmeister et al., "Zur chemie des ecdysons, III: Vergleichende spektrometrische untersuchungen an a.b-ungesättigten steroidketonen," Chemische Berichte, 98(7):2361-2375 (1965).
Iida et al., "An improved method for the capillary gas chromatographic derivatization of polyhydroxylated steroids having tert-hydroxyl groups," Analytical Sciences, 19(9):1317-1321 (2003).
Karaki et al., "Structure-activity relationship studies of Niemann-Pick type C1-like 1 (NPC1L1) ligands identified by screening assay monitoring pharmacological chaperone effect," Bioorganic and Medicinal Chemistry, 21(17):5297-5309 (2013).
Khripach et al., "Synthesis of (24S)-hydroxy-and (24S)-24,25-epoxycholesterol analogues, potential agonists of nuclear LXR receptors," Russian Journal of Bioorganic Chemistry, 32(6):586-594 (2006).
Knoppert et al., "Position paper: Paediatric age categories to be used in differentiating between listing on a model essential medicines list for children," pp. 1-5 (2007).
Kurosawa et al., "Synthesis of 19-hydroxylated bile acids and identification of 3 alpha,7 alpha,12 alpha,19-tetrahydroxy-5 beta-cholan-24oic acid in human neonatal urine," Chemical and Pharmaceutical Bulletin, 43(9):1551-1557 (1995).
Lakhan et al., "NMDA receptor activity in neuropsychiatric disorders," Frontiers in Psychiatry, 4:1-7 (2013).
Lala et al., "Role of nitric oxide in tumor progression: Lessons from experimental tumors," Cancer and Metastasis Reviews, 17(1):91-106 (1998).
Layzer, "Section five-degenerative diseases of the nervous system," Cecil Textbook of Medicine, 20th edition, 2:2050-2057 (1996).
Leoni et al., "Oxysterols as biomarkers in neurodegenerative diseases," Chemistry and Physics of Lipids, 164(6):515-524 (2011).
Lettré et al., "Mehrwertige alkohole aus sterinen und sterinderivaten, VI Steroide mit strukturmerkmalen des ecdysons und der elatericine," Justus Liebigs Annalen der Chemie, 758:89-110 (1972) (English Abstract).
Li et al., "Synthesis of 7alpha-hydroxy derivatives of regulatory oxysterols," Steroids, 65(9):529-535 (2000).
Linsenbardt et al., "Different oxysterols have opposing actions at N-methyl-D-aspartate receptors," Neuropharmacology, 85:232-242 (2014).
Luu et al., "Oxysterols: Old Tale, New Twists," Annual Review of Pharmacology and Toxicology, 56:447-467 (2016).
Mateos et al., "Activity-regulated cytoskeleton-associated protein in rodent brain is down regulated by high fat diet in vivo and by 27-hydroxycholesterol in vitro," Brain Pathology, 19(1):69-80 (2009).
Meljon et al., "Analysis by liquid chromatography-mass spectrometry of sterols and oxysterols in brain of the newborn Dhcr7(Δ3-5/T93M) mouse: a model of Smith-Lemli-Opitz syndrome," Biochemical Pharmacology, 86(1):43-55 (2013).
Mourino et al., "Studies on vitamin D (calciferol) and its analogs. 15. 24-nor-1a,25-dihydroxyvitamin D3 and 24-nor-25¬hydroxy-5,6-trans-vitamin D3," Journal of Medicinal Chemistry, 21(10):1025-1029 (1978).
Nagano et al., "Chemistry and biochemistry of Chinese drugs. Part II. Hydroxylated sterols, cytotoxic towards cancerous cells: synthesis and testing," Journal of Chemical Research, 9:218 (1977).
Olkkonen et al., "Oxysterols and their cellular effectors," Biomolecules, 2(1):76-103 (2012).
Park-Chung et al., "Distinct sites for inverse modulation of N-methyl-D-aspartate receptors by sulfated steroids," Molecular Pharmacology, 52(6):1113-1123 (1997).
Paul et al., "The major brain cholesterol metabolite 24(S)-hydroxycholesterol is a potent allosteric modulator of N-methyl-D-aspartate receptors," The Journal of Neuroscience, 33(44):17290-17300 (2013).
PCT International Search Report and Written Opinion for corresponding International Application No. PCT/US2012/054261, dated Nov. 28, 2012 (10 pages).
PCT International Search Report and Written Opinion for corresponding International Application No. PCT/US2014/026633, dated Jul. 14, 2014 (6 pages).
PCT International Search Report and Written Opinion for corresponding International Application No. PCT/US2014/026784, dated Jul. 8, 2014 (13 pages).
PCT International Search Report and Written Opinion for corresponding International Application No. PCT/US2015/036510, dated Sep. 15, 2015 (7 pages).
PCT International Search Report and Written Opinion for corresponding International Application No. PCT/US2015/054551, dated Jan. 8, 2016 (10 pages).
PCT International Search Report and Written Opinion for corresponding International Application No. PCT/US2016/041160, dated Oct. 28, 2016 (7 pages).
PCT International Search Report and Written Opinion for corresponding International Application No. PCT/US2016/041168, dated Sep. 15, 2016 (6 pages).
PCT International Search Report and Written Opinion for corresponding International Application No. PCT/US2016/041175, dated Sep. 16, 2016 (6 pages).
PCT International Search Report and Written Opinion for corresponding International Application No. PCT/US2017/025535, dated Jul. 3, 2017 (7 pages).
PCT International Search Report and Written Opinion for corresponding International Application No. PCT/US2017/031374, dated Jul. 17, 2017 (8 pages).
PCT International Search Report and Written Opinion for corresponding International Application No. PCT/US2017/041199, dated Aug. 29, 2017 (12 pages).
PCT International Search Report and Written Opinion for corresponding International Application No. PCT/US2017/054657, dated Nov. 21, 2017 (18 pages).
PCT International Search Report and Written Opinion for corresponding International Application No. PCT/US2017/057276, dated Nov. 12, 2017 (13 pages).
PCT International Search Report and Written Opinion for corresponding International Application No. PCT/US2017/057277, dated Feb. 20, 2018 (19 pages).
PCT Invitation to Correct Fees and Partial International Search Report and Provisional Opinion for corresponding International Application No. PCT/US2017/057277, dated Dec. 20, 2017 (13 pages).
PubChem, CID 132021, Ergostan-3,24-diol, Mar. 5, 2018 (15 pages).
PubChem, CID 54083335, Schembl4961477, Nov. 8, 2016 (13 pages).
PubChem, CID 54160779, Schembl4961477, Nov. 8, 2016 (13 pages).
PubChem, CID 58455549, Schembl12198161, Nov. 8, 2016 (13 pages).
PubChem, CID 65094, 25-Hydroxycholesterol, Nov. 18, 2016 (17 pages).

(56) References Cited

OTHER PUBLICATIONS

PubChem, CID 66966798, Cholane-3alpha,24,-diol, Nov. 8, 2016 (11 pages).
PubChem, CID 70604305, Schembl11528874, Nov. 8, 2016 (13 pages).
PubChem, CID 71508953, Mar. 5, 2018 (13 pages).
Reddy, "Pharmacology of endogenous neuroactive steroids," Critical Reviews in Neurobiology, 15(3-4):197-234 (2013).
Registry (STN) [online] CAS Registration No. 1392266-35-1; 13392266-34-0; 1271523-00-2; 185138-08-3; 185138-00-5; 1851387-82-0; 66450-87-1 (2012).
Roh et al., "Neuroprotective effects of ginsenoside Rg3 against 24-OH-cholesterol-induced cytotoxicity in cortical neurons," Journal of Ginseng Research, 34(3):246-253 (2010).
Schmidt et al "Inhibitory effect of oxygenated cholestan-3b-ol derivatives on the growth of *Mycobacterium tuberculosis*," Bioorganic & Medicinal Chemistry Letters, 23(22):6111-6113 (2013).
Sepe et al., "Total synthesis and pharmacological characterization of solomonsterol A, a potent marine pregnane-X-receptor agonist endowed with anti-inflammatory activity," Journal of Medicinal Chemistry, 54:4590-4599 (2011).
Stamp et al., "Plasma levels and therapeutic effect of 25-hydroxycholecalciferol in epileptic patients taking anticonvulsant drugs," British Medical Journal, 4(5831):9-12 (1972).
Stastna et al., "Synthesis of C3, C5, and C7 pregnane derivatives and their effect on NMDA receptor responses in cultured rat hippocampal neurons," Steroids, 74(2):256-263 (2008).
Steinrauf et al., "Synthesis and evaluation of sulfur-containing steroids against methylmercuric chloride toxicity," Journal of Pharmaceutical Sciences, 67(12):1739-1743 (1978).
Svoboda et al., "Treatment of Smith-Lemli-Opitz syndrome and other sterol disorders," American Journal of Medical Genetics Part C: Seminars in Medical Genetics, 160C(4): 285-294 (2012).
Takano et al., "Simple synthesis of 3b,24-dihydroxychol-5-en-7-one by oxidative cleavage of the side chain of cholesterol," Chemistry Letters, 14(8):1265-1266 (1995).
Tierney et al., "Abnormalities of cholesterol metabolism in autism spectrum disorders," American Journal of Medical Genetics Part B: Neuropsychiatric Genetics, 141B(6):666-668 (2006).
Tomek et al., "NMDA receptor modulators in the treatment of drug addiction," Pharmaceuticals (Basel), 6(2):251-258 (2013).
Wolozin et al., "The cellular biochemistry of cholesterol and statins: Insights into the pathophysiology and therapy of Alzheimer's disease," CNS Drug Review, 10(2):127-146 (2004).
Wong et al., "An efficient and convenient transformation of a-haloketones to a-hydroxyketones using cesium formate," Journal of Organometallic Chemistry, 694(21):3452-3455 (2004).
Xiangdong et al., "Highly stereoselective synthesis of 24R,25- and 24S, 25-dihydroxysteroid," Database Chemical Abstracts Service, Database accession No. 2001:174431 (2000) (4 pages).
Xilouri et al., "Neuroprotective effects of steroid analogues on P19-N neurons," Neurochemistry International, 50(4):660-670 (2007).
Yan et al., "Characterization of a synthetic steroid 24-keto-cholest-5-en-3b,19-diol as a neuroprotectant," CNS Neuroscience & Therapeutics, 21(6):486-495 (2015).
Yang et al., "New cytotoxic oxygenated sterols from marine bryozoan *Bugula neritina*," Natural Product Research, 25(16):1505-1511 (2011).
Zuliani et al., "Plasma 24S-hydroxycholesterol levels in elderly subjects with late onset Alzheimer's disease or vascular dementia: a case-control study," BMC Neurology, 11(121):1-8 (2011).
Berge et al., "Pharmaceutical salts," Journal of Pharmaceutical Sciences, 66(1):1-19 (1977).
Cais et al., "Temperature dependence of NR1/NR2B NMDA receptor channels," Neuroscience, 151(2):428-438 (2008).
Costa et al., "A novel family of negative and positive allosteric modulators of NMDA receptors," Journal of Pharmacology and Experimental Therapeutics, 335(3):614-21 (2010).
Dale et al., "Nuclear magnetic resonance enantiomer regents. Configurational correlations via nuclear magnetic resonance chemical shifts of diastereomeric mandelate, O-methylmandelate, and .alpha.-methoxy-.alpha.-trifluoromethylphenylacetate (MTPA) esters," Journal of the American Chemical Society, 95(2):512-519 (1973).
Ferriz et al., "Prodrug Design of Phenolic Drugs", Current Pharmaceutical Designs, vol. 16, pp. 2033-2052 (2010).
Fukuto et al., "Determination of the Mechanism of Demethlenation of (methylenedioxy)phenyl compounds by cytochrome P450 using deuterium isotope effects," Journal of Medicinal Chemistry, 34(9):2871-2876 (1991).
Gee et al., "GABA-dependent modulation of the Cl-ionophore by steroids in rat brain," European Journal of Pharmacology, 136(3):419-423 (1987).
Groden et al., "Determination of Fura-2 dissociation constants following adjustment of the apparent Ca-EGTA association constant for temperature and ionic strength," Cell Calcium, 12:(4)279-287 (1991).
Grynkiewicz et at., "A new generation of Ca2+ indicators with greatly improved fluorescence properties," Journal of Biological Chemistiy, 260(6):3440-3345 (1985).
Guthrie et al., "Morphological and biochemical differences expressed in separate dissociated cell cultures of dorsal and ventral halves of the mouse spinal cord," Brain Research, 420(2):313-323 (1987).
Hoeve et al., "The design of resolving agents. Chiral cyclic phosphoric acids," Journal of Organic Chemistry, 50(23):4508-4514 (1985).
Hogg et al., "An automated system for intracellular and intranuclear injection," Journal of Neuroscience, Methods, 169(1):65-75 (2008).
Hollmann et al., "Zinc potentiates agonist-induced currents at certain splice variants of the NMDA receptor," Neuron, 10(5):943-954 (1993).
Horak et al., "Molecular mechanism of pregnenolone sulfate action at NR1/NR2B receptors," Journal of Neuroscience, 24(46):10318-10325 (2004).
Huttunen et al., "Prodrugs—from serendipity to rational design," Pharmacological Reviews, 63(3):750-771 (2011).
Irwin et al., "Steroid potentiation and inhibition of N-methyl-D-aspartate receptor-mediated intracellular Ca++ responses: structure-activity studies," Journal of Pharmacology and Experimental Therapeutics, 271(2):677-682 (1994).
Jurman et al., "Visual identification of individual transfected cells for electrophysiology using antibody-coated beads," Biotechniques, 17(5):876-881 (1994).
Leoni et al., "Changes in human plasma levels of the brain specific oxysterol 24S-hydroxycholesterol during progression of multiple sclerosis," Neuroscience Letters, 331(3):163-166 (2002).
Lutjohann et al., "Cholesterol homeostasis in human brain: evidence for an age-dependent flux of 24S-hydroxycholesterol from the brain into the circulation," PNAS, 93(18):9799-804 (1996).
Madau et al, Program No. 613.2/B87. 2009 Neuroscience Meeting Planner. Chicago, IL: Society for Neuroscience (2009) (3 pages).
Monyer et al., "Heteromeric NMDA receptors: molecular and functional distinction of subtypes," Science, 256(5060):1217-1221 (1992).
Nagasaka et al., "Oxysterol changes along with cholesterol and vitamin D changes in adult phenylketonuric patients diagnosed by newborn mass-screening," Clinica Chimica Acta, 416:54-59 (2013).
Niemann-Pick overview [online] retrieved from the internet on Jul. 17, 2021 (URL: https://www.mayoclinic.org/diseases-conditions/niemann-pick/symptoms-causes/syc-20355887).
Niemann-Pick diagnosis-treatment [online] retrieved from the internet on Jul. 17, 2021 (URL: https://www.mayoclinic.org/diseases-conditions/niemann-pick/diagnosis-treatment/drc-20355890).
Petrovic et al., "Pregnenolone sulfate modulation of N-methyl-D-aspartate receptors is phosphorylation dependent," Neuroscience, 160:616-628 (2009).
Pritchett et al., "Transient expression shows ligand gating and allosteric potentiation of GABAA receptor subunits," Science, 242(4883)1306-1308 (1988).
Segal, "Pat hippocampal Neurons in Culture: Responses to Electrical and Chemical Stimuli," Journal of Neurophysiology, 50(6)1249-1264 (1983).

(56) References Cited

OTHER PUBLICATIONS

Takahashi et al., "Stereochemistry of reduction of the C-24,25 double bond in the conversion of desmosterol into cholesterol," Tetrahedron Letters, 44(2):341-344 (2003).

Verdoorn et al., "Functional properties of recombinant rat GABAA receptors depend upon subunit composition," Neuron, 4(6):919-928 (1990).

Vyklicky et al., "Calcium-mediated modulation of N-methyl-D-aspartate (NMDA) responses in cultured rat hippocampal neurones," Journal of Physiology, 470:575-600 (1993).

Wieland et al., "Comparative behavioral characterization of the neuroactive steroids 3 alpha-OH,5 alpha-pregnan-20-one and 3 alpha-OH,5 beta-pregnan-20-one in rodents," Psychopharmacology 118(1):65-71 (1995).

Wilen et al., "Strategies in Optical Resolutions," Tetrahedron 33:2725-2736 (1977).

Zhou et al., "Properties of HERG channels stably expressed in HEK 293 cells studied at physiological temperature," Biophysical Journal, 74(1):230-241 (1998).

U.S. Appl. No. 14/343,603, filed Nov. 25, 2014, Ravindra B. Upasani et al., Abandoned.

U.S. Appl. No. 14/775,401, filed Sep. 11, 2015, Kiran Reddy et al., Abandoned.

U.S. Appl. No. 14/775,678, filed Sep. 12, 2015, Gabriel Martinez Botella et al., Abandoned.

U.S. Appl. No. 15/319,504, filed Dec. 16, 2016, Boyd L. Harrison et al., Issued.

U.S. Appl. No. 15/517,886, filed Apr. 7, 2017, Michael C. Quirk et al., Pending.

U.S. Appl. No. 15/588,305, filed May 5, 2017, Gabriel Martinez Botella et al., Abandoned.

U.S. Appl. No. 15/742,422, filed Jan. 5, 2018, Francesco G. Salituro et al., Issued.

U.S. Appl. No. 15/742,424, filed Jan. 5, 2018, Francesco G. Salituro et al., Issued.

U.S. Appl. No. 15/742,425, filed Jan. 5, 2018, Francesco G. Salituro et al., Issued.

U.S. Appl. No. 15/917,263, filed Mar. 9, 2018, Gabriel Martinez Botella et al., Issued.

U.S. Appl. No. 15/917,272, filed Mar. 9, 2018, Gabriel Martinez Botella et al., Abandoned.

U.S. Appl. No. 16/028,790, filed Jul. 6, 2018, Boyd L. Harrison et al., Issued.

U.S. Appl. No. 16/089,896, filed Sep. 28, 2018, Albert Jean Robichaud et al., Abandoned.

U.S. Appl. No. 16/099,122, filed Nov. 5, 2018, Gabriel Martinez Botella et al., Issued.

U.S. Appl. No. 16/114,791, filed Aug. 28, 2018, Ravindra B. Upasani et al., Issued.

U.S. Appl. No. 16/227,013, filed Dec. 20, 2018, Gabriel Martinez Botella et al., Issued.

U.S. Appl. No. 16/227,009, filed Dec. 20, 2018, Francesco G. Salituro et al., Issued.

U.S. Appl. No. 16/315,250, filed Jan. 4, 2019, Francesco G. Salituro et al., Issued.

U.S. Appl. No. 16/338,315, filed Mar. 29, 2019, Francesco G. Salituro et al., Issued.

U.S. Appl. No. 16/343,235, filed Apr. 18, 2019, Francesco G. Salituro et al., Issued.

U.S. Appl. No. 16/343,238, filed Apr. 18, 2019, Francesco G. Salituro et al., Issued.

U.S. Appl. No. 16/879,460, filed May 20, 2020, Francesco G. Salituro et al., Pending.

U.S. Appl. No. 16/902,730, filed Jun. 16, 2020, Boyd L. Harrison et al., Pending.

U.S. Appl. No. 16/930,047, filed Jul. 15, 2020, Gabriel Martinez Botella et al., Pending.

U.S. Appl. No. 16/938,348, filed Jul. 24, 2020, James J. Doherty, Pending.

U.S. Appl. No. 16/942,235, filed Jul. 29, 2020, Ravindra B. Upasani et al., Pending.

U.S. Appl. No. 16/942,245, filed Jul. 29, 2020, Francesco G. Salituro et al., Pending.

U.S. Appl. No. 17/242,860, filed Apr. 28, 2021, Albert Jean Robichaud et al., Pending.

U.S. Appl. No. 17/381,829, filed Jul. 21, 2021, Gabriel Martinez Botella et al., Pending.

U.S. Appl. No. 17/386,364, filed Jul. 27, 2021, Francesco G. Salituro et al., Pending.

U.S. Appl. No. 17/395,155, filed Aug. 5, 2021, Francesco G. Salituro et al., Pending.

U.S. Appl. No. 17/396,034, filed Aug. 5, 2021, Francesco G. Salituro et al., Pending.

U.S. Appl. No. 17/476,153, filed Sep. 15, 2021, Francesco G. Salituro et al., Pending.

U.S. Appl. No. 15/742,424, filed Jan. 5, 2018, Francesco G. Salituro et al., Pending.

U.S. Appl. No. 16/089,896, filed Sep. 28, 2018, Albert Jean Robichaud et al., Pending.

U.S. Appl. No. 16/227,013, filed Dec. 20, 2018, Gabriel Martinez Botella et al., Pending.

U.S. Appl. No. 16/227,099, filed Dec. 20, 2018, Francesco G. Salituro et al., Issued.

U.S. Appl. No. 16/338,315, filed Mar. 29, 2019, Francesco G. Salituro et al., Pending.

U.S. Appl. No. 16/343,235, filed Apr. 18, 2019, Francesco G. Salituro et al., Pending.

U.S. Appl. No. 16/343,238, filed Apr. 18, 2019, Francesco G. Salituro et al., Pending.

OXYSTEROLS AND METHODS OF USE THEREOF

CROSS-REFERENCE TO RELATED APPLICATIONS

The present Application is a Divisional of U.S. Ser. No. 16/315,250, filed Jan. 4, 2019, which is a U.S. National Phase Application under 35 U.S.C. § 371 of International Application PCT/US2017/041199, filed Jul. 7, 2017, which claims priority to U.S. Ser. No. 62/359,532 filed Jul. 7, 2016, which is incorporated herein by reference in its entirety.

BACKGROUND OF THE INVENTION

NMDA receptors are heteromeric complexes comprised of NR1, NR2, and/or NR3 subunits and possess distinct recognition sites for exogenous and endogenous ligands. These recognition sites include binding sites for glycine, and glutamate agonists and modulators. NMDA receptors are expressed in the peripheral tissues and the CNS, where they are involved in excitatory synaptic transmission. Activating these receptors contributes to synaptic plasticity in some circumstances and excitotoxicity in others. These receptors are ligand-gated ion channels that admit Ca2+ after binding of the glutamate and glycine, and are fundamental to excitatory neurotransmission and normal CNS function. Positive modulators may be useful as therapeutic agents with potential clinical uses as cognitive enhancers and in the treatment of psychiatric disorders in which glutamatergic transmission is reduced or defective (see, e.g., Horak et al., J. of Neuroscience, 2004, 24(46), 10318-10325). In contrast, negative modulators may be useful as therapeutic agents with potential clinical uses in the treatment of psychiatric disorders in which glutamatergic transmission is pathologically increased (e.g., treatment resistant depression).

Oxysterols are cholesterol analogs that are modulators of NMDA receptor function. There is a need for new oxysterols that modulate the NMDA receptor for the prevention and treatment of conditions associated with NMDA expression and function. Compounds, compositions, and methods described herein are directed toward this end.

SUMMARY OF THE INVENTION

Provided herein are new oxysterols useful for preventing and/or treating a broad range of disorders, including, but not limited to, NMDA-mediated disorders. Further provided are pharmaceutical compositions comprising the compounds of the present invention, and methods of their use and treatment.

In one aspect, provided herein are compounds according to Formula (I):

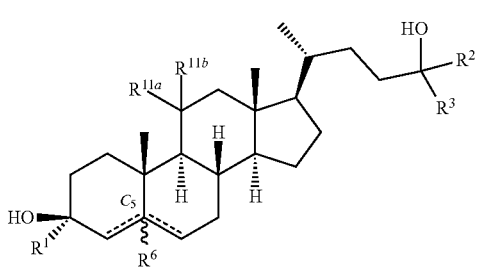

(I)

or a pharmaceutically acceptable salt thereof, wherein:

$R^1$ is hydrogen or $C_1$-$C_6$ alkyl; each of $R^2$ and $R^3$ is independently hydrogen, $C_1$-$C_6$ alkyl, or carbocyclyl, or $R^2$ and $R^3$, together with the carbon atom to which they are attached, form a 3-8 membered ring; $R^6$ is absent or hydrogen; $R^{11a}$ is hydrogen or $C_1$-$C_6$ alkyl (e.g., methyl) and $R^{11b}$ is —OH, or $C_1$-$C_6$ alkyl, or $R^{11a}$ and $R^{11b}$ are joined together to form oxo; and ==== represents a single or double bond, wherein when one ==== is a double bond, the other ==== is a single bond; and when one of the ==== is a double bond, $R^6$ is absent.

In some embodiments, $R^{11a}$ and $R^{11b}$ are not joined together to form oxo.

In some embodiments, $R^1$ is $C_{1-6}$ alkyl. In some embodiments, $R^1$ is hydrogen, methyl or ethyl, —$CHF_2$, —$CF_3$, —$CH_2OCH_3$, or —$CH_2OCH_2CH_3$. In some embodiments, $R^1$ is unsubstituted $C_{1-6}$ alkyl (e.g., —$CH_3$ or —$CH_2CH_3$). In some embodiments, $R^1$ is hydrogen. In some embodiments, $R^1$ is —$CH_3$. In some embodiments, $R^1$ is —$CH_2CH_3$.

In some embodiments, each of $R^2$ and $R^3$ is independently hydrogen, methyl, ethyl, propyl, isopropyl, cyclopropyl, butyl (e.g., tert-butyl), —$CF_3$, or —$CH_2CF_3$. In some embodiments, each of $R^2$ and $R^3$ is independently methyl, isopropyl, or tert-butyl.

In some embodiments, $R^2$ is hydrogen, methyl, ethyl, or —$CF_3$.

In some embodiments, $R^3$ is methyl, ethyl, propyl, isopropyl, cyclopropyl, butyl (e.g., tert-butyl), —$CF_3$, or —$CH_2CF_3$.

In some embodiments, $R^{11a}$ is hydrogen and $R^{11b}$ is —OH. In some embodiments, $R^{11a}$ is $C_1$-$C_6$ alkyl (e.g., methyl) and $R^{11b}$ is —OH. In some embodiments, $R^{11a}$ and $R^{11b}$ are joined together to form oxo.

In some embodiments, the compound of Formula (I) is a compound of Formula (I-A) or Formula (I-B):

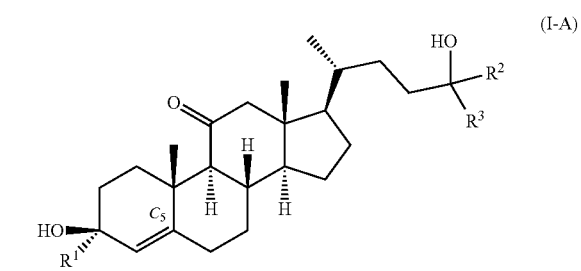

(I-A)

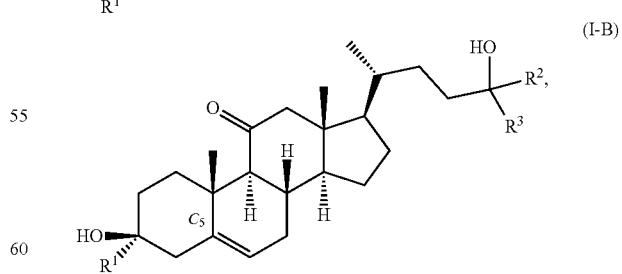

(I-B)

or a pharmaceutically acceptable salt thereof.

In some embodiments, each of ==== is a single bond.

In some embodiments, the compound of Formula (I) is a compound of Formula (II):

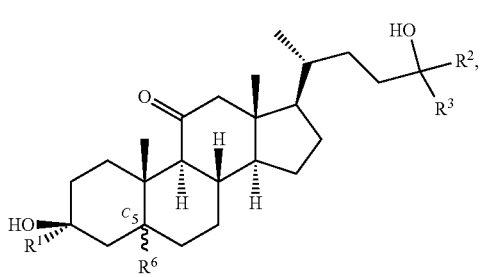

(II)

or a pharmaceutically acceptable salt thereof.

In some embodiments, the compound of Formula (II) is a compound of Formula (II-A) or Formula (II-B):

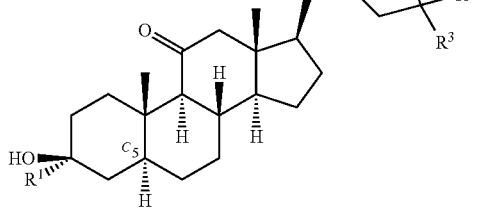

(II-A)

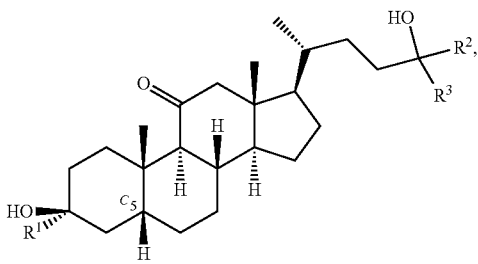

(II-B)

or a pharmaceutically acceptable salt thereof.

In some embodiments, $R^1$ is $C_{1-6}$ alkyl. In some embodiments, $R^1$ is hydrogen, methyl, ethyl, —$CHF_2$, —$CF_3$, —$CH_2OCH_3$, or —$CH_2OCH_2CH_3$.

In some embodiments, each of $R^2$ and $R^3$ is independently hydrogen, methyl, ethyl, propyl, isopropyl, cyclopropyl, butyl (e.g., tert-butyl), —$CF_3$, or —$CH_2CF_3$.

In some embodiments, $R^2$ is hydrogen, methyl, ethyl, or —$CF_3$.

In some embodiments, $R^3$ is methyl, ethyl, propyl, isopropyl, cyclopropyl, butyl, —$CF_3$, or —$CH_2CF_3$.

In an aspect, provided herein is a compound selected from the group consisting of:

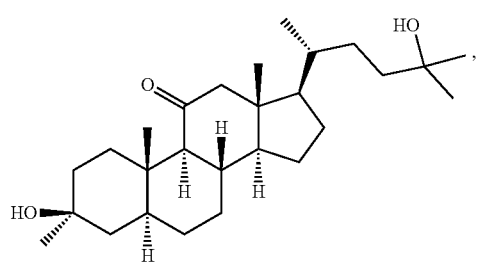

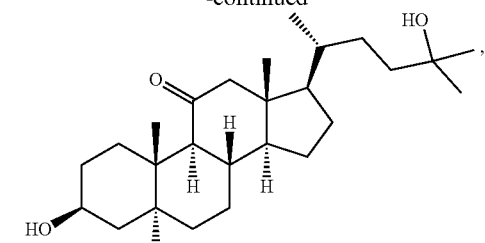

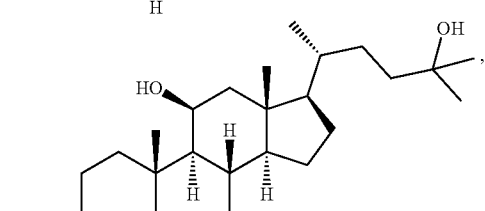

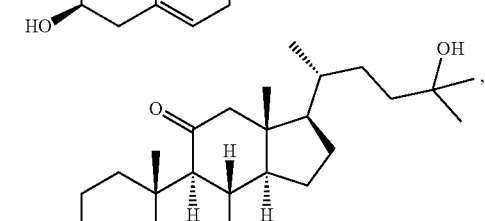

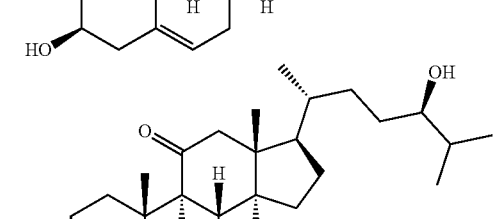

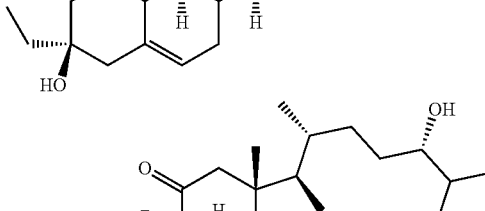

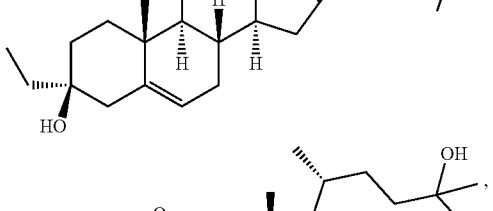

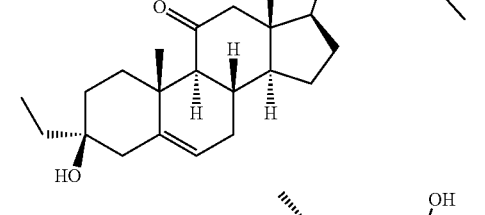

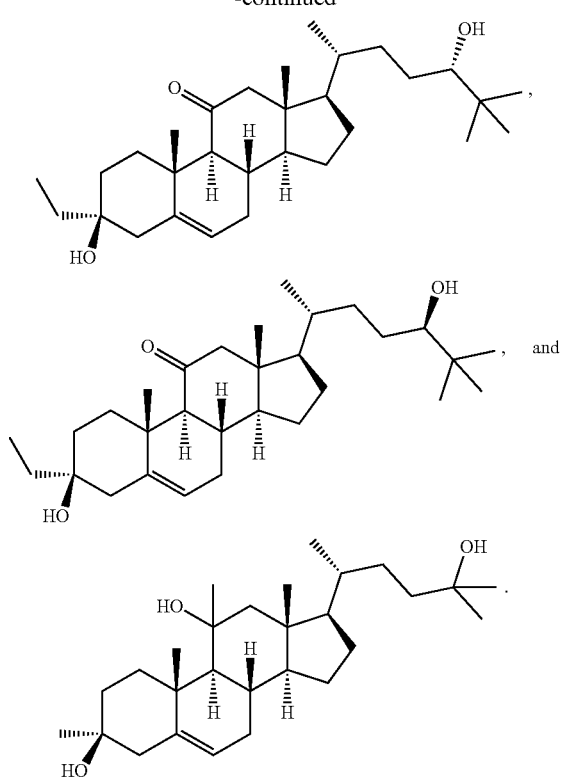
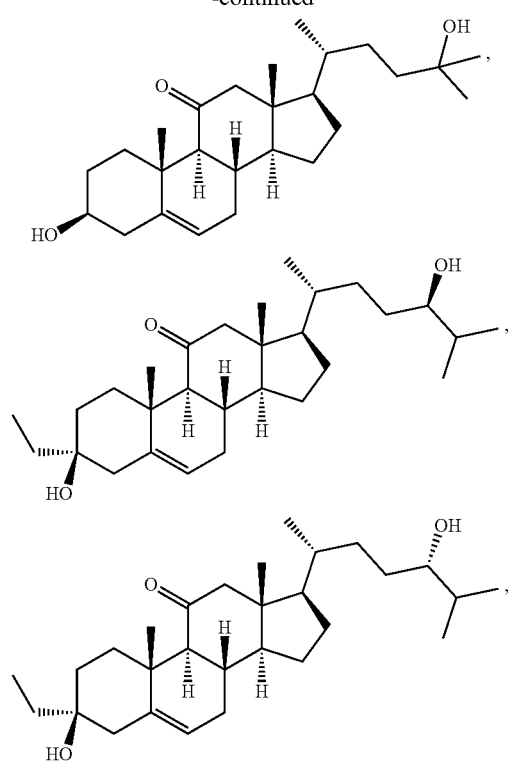
In an aspect, provided herein is a pharmaceutically acceptable salt of a compound selected from the group consisting of:
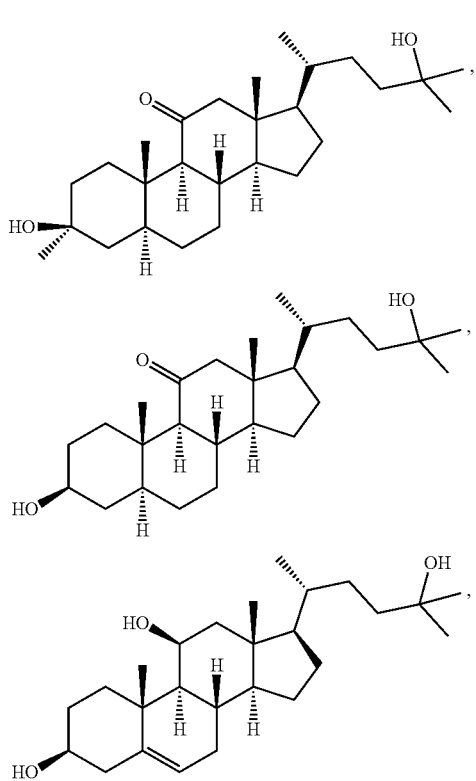
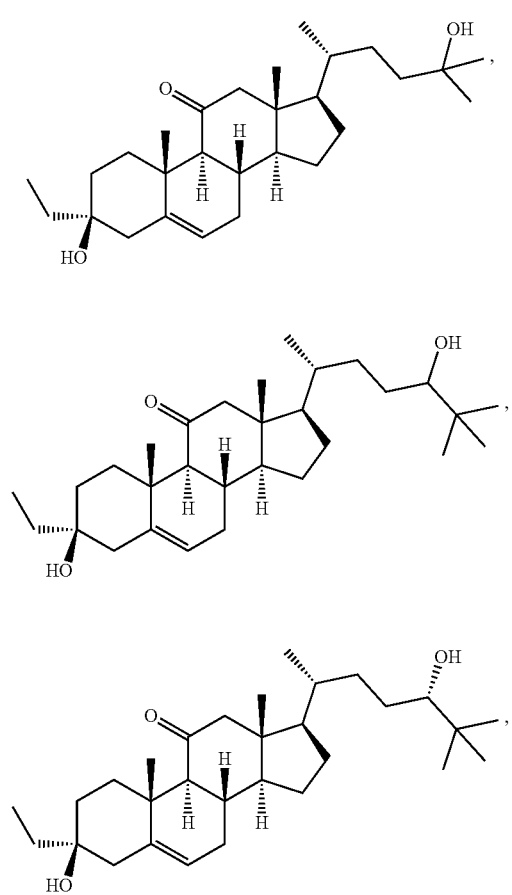

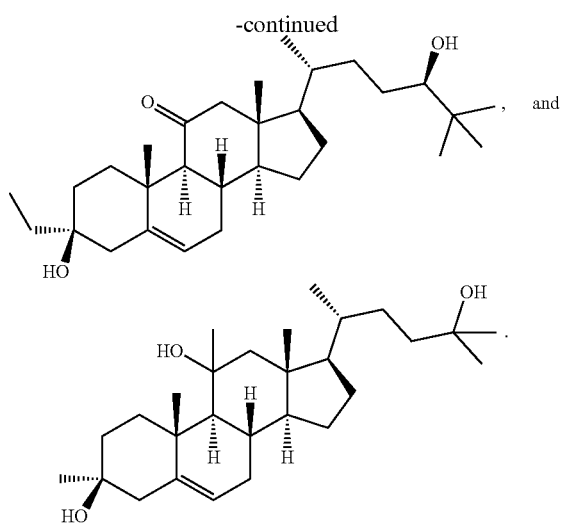

In some embodiments, the compound of Formula (I) is a compound of Formula (III):

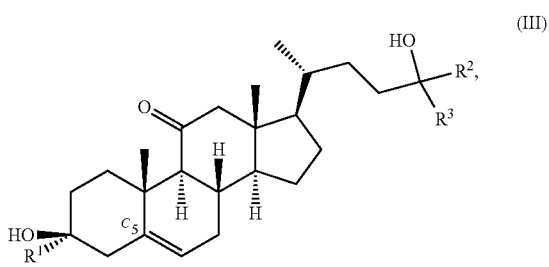

or a pharmaceutically acceptable salt thereof.

In some embodiments, $R^1$ is $C_{1-6}$ alkyl. In some embodiments, $R^1$ is hydrogen. In some embodiments, $R^1$ is —CH$_2$CH$_3$. In some embodiments, $R^1$ is hydrogen, methyl, ethyl, —CHF$_2$, —CF$_3$, —CH$_2$OCH$_3$, or —CH$_2$OCH$_2$CH$_3$.

In some embodiments, each of $R^2$ and $R^3$ is independently hydrogen, methyl, ethyl, propyl, isopropyl, cyclopropyl, butyl (e.g., tert-butyl), —CF$_3$, or —CH$_2$CF$_3$.

In some embodiments, $R^2$ is hydrogen, methyl, ethyl, or —CF$_3$.

In some embodiments, $R^3$ is methyl, ethyl, propyl, isopropyl, cyclopropyl, butyl (e.g., tert-butyl), —CF$_3$, or —CH$_2$CF$_3$.

In an aspect, provided herein is a pharmaceutical composition comprising a compound described herein, or pharmaceutically acceptable salt thereof, and a pharmaceutically acceptable carrier.

In an aspect, provided herein is a method of inducing sedation or anesthesia comprising administering to a subject an effective amount of a compound described herein, or pharmaceutically acceptable salt thereof, or pharmaceutical composition thereof.

In an aspect, provided herein is a method for treating or preventing a disorder described herein, comprising administering to a subject in need thereof an effective amount of a compound described herein, or pharmaceutically acceptable salt thereof, or pharmaceutical composition thereof.

In some embodiments, the disorder is a gastrointestinal (GI) disorder e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis.

In some embodiments, the disorder is inflammatory bowel disease.

In some embodiments, the disorder is cancer, diabetes, or a sterol synthesis disorder.

In an aspect, provided herein is a method for treating or preventing a condition (e.g., CNS-related condition) comprising administering to a subject in need thereof an effective amount of a compound described herein, or pharmaceutically acceptable salt thereof, or pharmaceutical composition thereof. In some embodiments, the condition is an adjustment disorder, anxiety disorders (including obsessive-compulsive disorder, posttraumatic stress disorder, social phobia, generalized anxiety disorder), cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g., Shank3)), neurodevelopmental disorders (including Rett syndrome), multiple sclerosis, sterol synthesis disorders, Smith-Lemli-Optiz syndrome, pain (including acute pain, chronic pain, and neuropathic pain), seizure disorders (including status epilepticus and monogenic forms of epilepsy such as Dravet's disease, Tuberous Sclerosis Complex (TSC), and infantile spasms), stroke, subarachnoid hemorrhage, intracerebral hemorrhage, cerebral ischemia, traumatic brain injury, movement disorders (including Huntington's disease and Parkinson's disease) attention deficit disorder, attention deficit hyperactivity disorder, metabolic encephalopathies (including phenylketoneuria), post-partum psychosis, syndromes associated with high titers of anti-NMDA receptor antibodies (including anti-NMDA receptor encephalitis), neurodegenerative disorders, neuroinflammation, neuropsychiatric lupus, Niemann-Pick C disorder, and tinnitus.

In some embodiments, the disorder is sterol synthesis disorder.

Other objects and advantages will become apparent to those skilled in the art from a consideration of the ensuing Detailed Description, Examples, and Claims.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley &

Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Isomers, e.g., stereoisomers, can be isolated from mixtures by methods known to those skilled in the art, including chiral high pressure liquid chromatography (HPLC), supercritical fluid chromatography (SFC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972).

The invention additionally encompasses compounds described herein as individual isomers substantially free of other isomers, and alternatively, as mixtures of various isomers.

The absolute configuration of an asymmetric center can be determined using methods known to one skilled in the art. In some embodiments, the absolute configuration of an asymmetric center in a compound can be elucidated from the X-ray single-crystal structure of the compound. In some embodiments, an asymmetric center of known absolute configuration can be introduced into a compound with a chiral reactant, e.g., a chiral epoxide.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The following terms are intended to have the meanings presented therewith below and are useful in understanding the description and intended scope of the present invention. When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

"Aliphatic" refers to an alkyl, alkenyl, alkynyl, or cycloalkyl group, as defined herein.

"Alkyl" refers to a radical of a straight-chain or branched saturated hydrocarbon group having from 1 to 20 carbon atoms ("$C_{1-20}$ alkyl"). In some embodiments, an alkyl group has 1 to 12 carbon atoms ("$C_{1-12}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl", also referred to herein as "lower alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), iPr (—$CH(CH_3)_2$), nPr (—$CH_2CH_2CH_3$), n-Bu (—$CH_2CH_2CH_2CH_3$), or i-Bu (—$CH_2CH(CH_3)_2$).

"Alkylene" refers to an alkyl group wherein two hydrogens are removed to provide a divalent radical, and which may be substituted or unsubstituted. Unsubstituted alkylene groups include, but are not limited to, methylene (—$CH_2$—), ethylene (—$CH_2CH_2$—), propylene (—$CH_2CH_2CH_2$—), butylene (—$CH_2CH_2CH_2CH_2$—), pentylene (—$CH_2CH_2CH_2CH_2CH_2$—), hexylene (—$CH_2CH_2CH_2CH_2CH_2CH_2$—), and the like. Exemplary substituted alkylene groups, e.g., substituted with one or more alkyl (methyl) groups, include but are not limited to, substituted methylene (—$CH(CH_3)$—, —$C(CH_3)_2$—), substituted ethylene (—$CH(CH_3)CH_2$—, —$CH_2CH(CH_3)$—, —$C(CH_3)_2CH_2$—, —$CH_2C(CH_3)_2$—), substituted propylene (—$CH(CH_3)CH_2CH_2$—, —$CH_2CH(CH_3)CH_2$—, —$CH_2CH_2CH(CH_3)$—, —$C(CH_3)_2CH_2CH_2$—, —$CH_2C(CH_3)_2CH_2$—, —$CH_2CH_2C(CH_3)_2$—), and the like. When a range or number of carbons is provided for a particular alkylene group, it is understood that the range or number refers to the range or number of carbons in the linear carbon divalent chain. Alkylene groups may be substituted or unsubstituted with one or more substituents as described herein.

"Alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_2$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_2$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents e.g., for instance from 1 to 5 substituents, 1 to 3 substituents, or 1 substituent. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon-carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents; e.g., for instance from 1 to 5 substituents, 1 to 3 substituents, or 1 substituent. In certain embodiments, the alkynyl group is unsubstituted $C_{2-10}$ alkynyl. In certain embodiments, the alkynyl group is substituted $C_{2-10}$ alkynyl.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("hetero$C_{1-10}$ alkyl"). In some embodiments, a heteroalkyl group is a saturated group having 1 to 9 carbon atoms and 1, 2, 3, or 4 heteroatoms ("hetero$C_{1-9}$ alkyl"). In some embodiments, a heteroalkyl group is a saturated group having 1 to 8 carbon atoms and 1, 2, 3, or 4 heteroatoms ("hetero$C_{1-8}$ alkyl"). In some embodiments, a heteroalkyl group is a saturated group having 1 to 7 carbon atoms and 1, 2, 3, or 4 heteroatoms ("hetero$C_{1-7}$ alkyl"). In some embodiments, a heteroalkyl group is a group having 1 to 6 carbon atoms and 1, 2, or 3 heteroatoms ("hetero$C_{1-6}$ alkyl"). In some embodiments, a heteroalkyl group is a saturated group having 1 to 5 carbon atoms and 1 or 2 heteroatoms ("hetero$C_{1-5}$ alkyl"). In some embodiments, a heteroalkyl group is a saturated group having 1 to 4 carbon atoms and for 2 heteroatoms ("hetero$C_{1-4}$ alkyl"). In some embodiments, a heteroalkyl group is a saturated group having 1 to 3 carbon atoms and 1 heteroatom ("hetero$C_{1-3}$ alkyl"). In some embodiments, a heteroalkyl group is a saturated group having 1 to 2 carbon atoms and 1 heteroatom ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

In certain embodiments, an aryl group substituted with one or more of groups selected from halo, $C_1$-$C_8$ alkyl, $C_1$-$C_8$ haloalkyl, cyano, hydroxy, $C_1$-$C_8$ alkoxy, and amino.

Examples of representative substituted aryls include the following

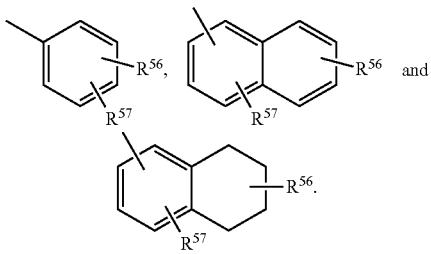

wherein one of $R^{56}$ and $R^{57}$ may be hydrogen and at least one of $R^{56}$ and $R^{57}$ is each independently selected from $C_1$-$C_8$ alkyl, $C_1$-$C_8$ haloalkyl, 4-10 membered heterocyclyl, alkanoyl, $C_1$-$C_8$ alkoxy, heteroaryloxy, alkylamino, arylamino, heteroarylamino, $NR^{58}COR^{59}$, $NR^{58}SOR^{59}NR^{58}SO_2R^{59}$, COOalkyl, COOaryl, $CONR^{58}R^{59}$, $CONR^{58}OR^{59}$, $NR^{58}R^{59}$, $SO_2NR^{58}R^{59}$, S-alkyl, SOalkyl, $SO_2$alkyl, Saryl, SOaryl, $SO_2$aryl; or $R^{56}$ and $R^{57}$ may be joined to form a cyclic ring (saturated or unsaturated) from 5 to 8 atoms, optionally containing one or more heteroatoms selected from the group N, O, or S. $R^{60}$ and $R^{61}$ are independently hydrogen, $C_1$-$C_8$ alkyl, $C_1$-$C_4$haloalkyl, $C_3$-$C_1$° cycloalkyl, 4-10 membered heterocyclyl, $C_6$-$C_1$° aryl, substituted $C_6$-$C_{10}$ aryl, 5-10 membered heteroaryl, or substituted 5-10 membered heteroaryl.

"Fused aryl" refers to an aryl having two of its ring carbon in common with a second aryl or heteroaryl ring or with a carbocyclyl or heterocyclyl ring.

"Aralkyl" is a subset of alkyl and aryl, as defined herein, and refers to an optionally substituted alkyl group substituted by an optionally substituted aryl group.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

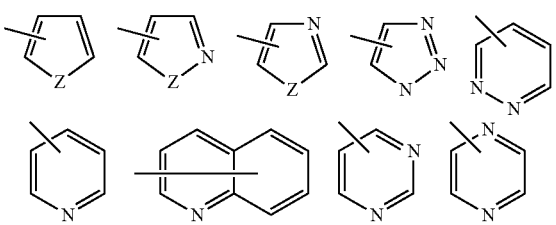

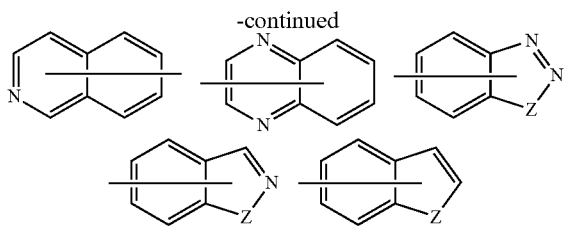

wherein each Z is selected from carbonyl, N, NR$^{65}$, O, and S; and CR$^{65}$ is independently hydrogen, C$_1$-C$_8$ alkyl, C$_3$-C$_{10}$ cycloalkyl, 4-10 membered heterocyclyl, C$_6$-C$_{10}$ aryl, and 5-10 membered heteroaryl.

"Heteroaralkyl" is a subset of alkyl and heteroaryl, as defined herein, and refers to an optionally substituted alkyl group substituted by an optionally substituted heteroaryl group.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 7 ring carbon atoms ("C$_{3-7}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is a substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Nitrogen-containing heterocyclyl" group means a 4- to 7-membered non-aromatic cyclic group containing at least one nitrogen atom, for example, but without limitation, morpholine, piperidine (e.g. 2-piperidinyl, 3-piperidinyl and 4-piperidinyl), pyrrolidine (e.g. 2-pyrrolidinyl and 3-pyrrolidinyl), azetidine, pyrrolidone, imidazoline, imidazolidinone, 2-pyrazoline, pyrazolidine, piperazine, and N-alkyl piperazines such as N-methyl piperazine. Particular examples include azetidine, piperidone and piperazone.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl, cycloalkyl, e.g., heterocyclyl, aryl, e.g., heteroaryl, cycloalkenyl, e.g., cycloheteroalkenyl, and the like having from 1 to 5, and particularly from 1 to 3 heteroatoms.

"Acyl" refers to a radical —C(O)$R^{20}$, where $R^{20}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, as defined herein. "Alkanoyl" is an acyl group wherein $R^{20}$ is a group other than hydrogen. Representative acyl groups include, but are not limited to, formyl (—CHO), acetyl (—C(=O)CH$_3$), cyclohexylcarbonyl, cyclohexylmethylcarbonyl, benzoyl (—C(=O)Ph), benzylcarbonyl (—C(=O)CH$_2$Ph), —C(O)—$C_1$-$C_8$ alkyl, —C(O)—(CH$_2$)$_t$($C_6$-$C_{10}$ aryl), —C(O)—(CH$_2$)$_t$(5-10 membered heteroaryl), —C(O)—(CH$_2$)$_t$($C_3$-$C_{10}$ cycloalkyl), and —C(O)—(CH$_2$)$_t$(4-10 membered heterocyclyl), wherein t is an integer from 0 to 4. In certain embodiments, $R^{21}$ is $C_1$-$C_8$ alkyl, substituted with halo or hydroxy; or $C_3$-$C_{10}$ cycloalkyl, 4-10 membered heterocyclyl, $C_6$-$C_{10}$ aryl, arylalkyl, 5-10 membered heteroaryl or heteroarylalkyl, each of which is substituted with unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy.

"Alkoxy" refers to the group —OR$^{29}$ where R$^{29}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl. Particular alkoxy groups are methoxy, ethoxy, n-propoxy, isopropoxy, n-butoxy, tert-butoxy, sec-butoxy, n-pentoxy, n-hexyloxy, and 1,2-dimethylbutoxy. Particular alkoxy groups are lower alkoxy, i.e. with between 1 and 6 carbon atoms. Further particular alkoxy groups have between 1 and 4 carbon atoms.

In certain embodiments, R$^{29}$ is a group that has 1 or more substituents, for instance from 1 to 5 substituents, and particularly from 1 to 3 substituents, in particular 1 substituent, selected from the group consisting of amino, substituted amino, $C_6$-$C_{10}$ aryl, aryloxy, carboxyl, cyano, $C_3$-$C_{10}$ cycloalkyl, 4-10 membered heterocyclyl, halogen, 5-10 membered heteroaryl, hydroxyl, nitro, thioalkoxy, thioaryloxy, thiol, alkyl-S(O)—, aryl-S(O)—, alkyl-S(O)$_2$— and aryl-S(O)$_2$—. Exemplary 'substituted alkoxy' groups include, but are not limited to, —O—(CH$_2$)$_t$($C_6$-$C_{10}$ aryl), —O—(CH$_2$)$_t$(5-10 membered heteroaryl), —O—(CH$_2$)$_t$($C_3$-$C_{10}$ cycloalkyl), and —O—(CH$_2$)$_t$(4-10 membered heterocyclyl), wherein t is an integer from 0 to 4 and any aryl, heteroaryl, cycloalkyl or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. Particular exemplary 'substituted alkoxy' groups are —OCF$_3$, —OCH$_2$CF$_3$, —OCH$_2$Ph, —OCH$_2$— cyclopropyl, —OCH$_2$CH$_2$OH, and —OCH$_2$CH$_2$NMe$_2$.

"Amino" refers to the radical —NH$_2$.

"Oxo" refers to the group =O.

"Substituted amino" refers to an amino group of the formula —N(R$^{38}$)$_2$ wherein each R$^{38}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an amino protecting group, wherein at least one of R$^{38}$ is not a hydrogen. In certain embodiments, each R$^{38}$ is independently selected from hydrogen, $C_1$-$C_8$ alkyl, $C_3$-$C_8$ alkenyl, $C_3$-$C_8$ alkynyl, $C_6$-$C_{10}$ aryl, 5-10 membered heteroaryl, 4-10 membered heterocyclyl, or $C_3$-$C_{10}$ cycloalkyl; or $C_1$-$C_8$ alkyl, substituted with halo or hydroxy; $C_3$-$C_8$ alkenyl, substituted with halo or hydroxy; $C_3$-$C_8$ alkynyl, substituted with halo or hydroxy, or —(CH$_2$)$_t$($C_6$-$C_{10}$ aryl), —(CH$_2$)$_t$(5-10 membered heteroaryl), —(CH$_2$)$_t$($C_3$-$C_{10}$ cycloalkyl), or —(CH$_2$)$_t$(4-10 membered heterocyclyl), wherein t is an integer between 0 and 8, each of which is substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy; or both R$^{38}$ groups are joined to form an alkylene group.

Exemplary "substituted amino" groups include, but are not limited to, —NR$^{39}$—$C_1$-$C_8$ alkyl, —NR$^{39}$—(CH$_2$)$_t$($C_6$-$C_{10}$ aryl), —NR$^{39}$—(CH$_2$)$_t$(5-10 membered heteroaryl), —NR$^{39}$—(CH$_2$)$_t$($C_3$-$C_{10}$ cycloalkyl), and —NR$^{39}$—(CH$_2$)$_t$ (4-10 membered heterocyclyl), wherein t is an integer from 0 to 4, for instance 1 or 2, each $R^{39}$ independently represents H or $C_1$-$C_8$ alkyl; and any alkyl groups present, may themselves be substituted by halo, substituted or unsubstituted amino, or hydroxy; and any aryl, heteroaryl, cycloalkyl, or heterocyclyl groups present, may themselves be substituted by unsubstituted $C_1$-$C_4$ alkyl, halo, unsubstituted $C_1$-$C_4$ alkoxy, unsubstituted $C_1$-$C_4$ haloalkyl, unsubstituted $C_1$-$C_4$ hydroxyalkyl, or unsubstituted $C_1$-$C_4$ haloalkoxy or hydroxy. For the avoidance of doubt, the term 'substituted amino' includes the groups alkylamino, substituted alkylamino, alkylarylamino, substituted alkylarylamino, arylamino, substituted arylamino, dialkylamino, and substituted dialkylamino as defined below. Substituted amino encompasses both monosubstituted amino and disubstituted amino groups.

"Carboxy" refers to the radical —C(O)OH.

"Cyano" refers to the radical —CN.

"Halo" or "halogen" refers to fluoro (F), chloro (Cl), bromo (Br), and iodo (I). In certain embodiments, the halo group is either fluoro or chloro.

"Hydroxy" refers to the radical —OH.

"Nitro" refers to the radical —$NO_2$.

"Cycloalkylalkyl" refers to an alkyl radical in which the alkyl group is substituted with a cycloalkyl group. Typical cycloalkylalkyl groups include, but are not limited to, cyclopropylmethyl, cyclobutylmethyl, cyclopentylmethyl, cyclohexylmethyl, cycloheptylmethyl, cyclooctylmethyl, cyclopropylethyl, cyclobutylethyl, cyclopentylethyl, cyclohexylethyl, cycloheptylethyl, and cyclooctylethyl, and the like.

"Heterocyclylalkyl" refers to an alkyl radical in which the alkyl group is substituted with a heterocyclyl group. Typical heterocyclylalkyl groups include, but are not limited to, pyrrolidinylmethyl, piperidinylmethyl, piperazinylmethyl, morpholinylmethyl, pyrrolidinylethyl, piperidinylethyl, piperazinylethyl, morpholinylethyl, and the like.

"Thioketo" refers to the group =S.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, $N(R^{bb})_2$, —$N(R^{bb})_3^+X^-$, —$N(OR^{cc})R^{bb}$, —SH, —$SR^{aa}$, —$SSR^{cc}$, —C(=O)$R^{aa}$, —$CO_2H$, —CHO, —C(O$R^{cc}$)$_2$, —$CO_2R^{aa}$, —OC(=O)$R^{aa}$, —$OCO_2R^{aa}$, —C(=O)N($R^{bb}$)$_2$, —OC(=O)N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —C(=N$R^{bb}$)$R^{aa}$, —C(=N$R^{bb}$)$OR^{aa}$, —OC(=N$R^{bb}$)$R^{aa}$, —OC(=N$R^{bb}$)$OR^{aa}$, —C(=N$R^{bb}$)N($R^{bb}$)$_2$, —OC(=N$R^{bb}$)N($R^{bb}$)$_2$, —$NR^{bb}$C(=N$R^{bb}$)N($R^{bb}$)$_2$, —C(=O)$NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —S(=O)$R^{aa}$, —OS(=O)$R^{aa}$, —Si($R^{aa}$)$_3$, —OSi($R^{aa}$)$_3$, —C(=S)N($R^{bb}$)$_2$, —C(=O)$SR^{aa}$, —C(=S)$SR^{aa}$, —SC(=S)$SR^{aa}$, —SC(=O)$SR^{aa}$, —OC(=O)$SR^{aa}$, —SC(=O)$OR^{aa}$, —SC(=O)$R^{aa}$, —P(=O)$_2R^{aa}$, —OP(=O)$_2R^{aa}$, —P(=O)($R^{aa}$)$_2$, —OP(=O)($R^{aa}$)$_2$, —OP(=O)($OR^{cc}$)$_2$, —P(=O)$_2N(R^{bb})_2$, —OP(=O)$_2N(R^{bb})_2$, —P(=O)(N$R^{bb}$)$_2$, —OP(=O)(N$R^{bb}$)$_2$, —$NR^{bb}$P(=O)($OR^{cc}$)$_2$, —$NR^{bb}$P(=O)(N$R^{bb}$)$_2$, —P($R^{cc}$)$_2$, —P($R^{cc}$)$_3$, —OP($R^{cc}$)$_2$, —OP($R^{cc}$)$_3$, —B($R^{aa}$)$_2$, —B($OR^{cc}$)$_2$, —B$R^{aa}$($OR^{cc}$), $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group =O, =S, =NN($R^{bb}$)$_2$, =NN$R^{bb}$C(=O)$R^{aa}$, =NN$R^{bb}$C(=O)$OR^{aa}$, =NN$R^{bb}$S(=O)$_2R^{aa}$, =N$R^{bb}$, or =NO$R^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —$OR^{aa}$, —N($R^{cc}$)$_2$, —CN, —C(=O)$R^{aa}$, —C(=O)N($R^{cc}$)$_2$, —$CO_2R^{aa}$, —$SO_2R^{aa}$, —C(=N$R^{cc}$)$OR^{aa}$, —C(=N$R^{cc}$)N($R^{cc}$)$_2$, —$SO_2N(R^{cc})_2$, —$SO_2R^{cc}$, —$SO_2OR^{cc}$, —$SOR^{aa}$, —C(=S)N($R^{cc}$)$_2$, —C(=O)$SR^{cc}$, —C(=S)$SR^{cc}$, —P(=O)$_2R^{aa}$, —P(=O)($R^{aa}$)$_2$, —P(=O)$_2N(R^{cc})_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —$NO_2$, —$N_3$, —$SO_2H$, —$SO_3H$, —OH, —$OR^{ee}$, —ON($R^{ff}$)$_2$, —N($R^{ff}$)$_2$, —N($R^{ff}$)$_3^+X^-$, —N($OR^{ee}$)$R^{ff}$, —SH, —$SR^{ee}$, —$SSR^{ee}$, —C(=O)$R^{ee}$, —$CO_2H$, —$CO_2R^{ee}$, —OC(=O)$R^{ee}$, —$OCO_2R^{ee}$, —C(=O)N($R^{ff}$)$_2$, —OC(=O)N($R^{ff}$)$_2$, —$NR^{ff}$C(=O)$R^{ee}$, —$NR^{ff}CO_2R^{ee}$, —$NR^{ff}$C(=O)N($R^{ff}$)$_2$, —C(=N$R^{ff}$)$OR^{ee}$, —OC(=N$R^{ff}$)

$R^{ee}$, —OC(=NR$^{ff}$)OR$^{ee}$, —C(=NR$^{ff}$)N(R))$_2$, —OC(=NR))N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{is}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two R groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal R$^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, SO$_4$$^{-2}$ sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^a$, —SO$_2$R$^{aa}$, —C(=NR$^{bb}$)R$^{aa}$, —(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

These and other exemplary substituents are described in more detail in the Detailed Description, Examples, and claims. The invention is not intended to be limited in any manner by the above exemplary listing of substituents.

Other Definitions

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

A "subject" to which administration is contemplated includes, but is not limited to, humans (i.e., a male or female of any age group, e.g., a pediatric subject (e.g. infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

DETAILED DESCRIPTION OF CERTAIN EMBODIMENTS OF THE INVENTION

As generally described herein, the present invention provides oxysterols useful for preventing and/or treating a broad range of disorders, including, but not limited to, NMDA-mediated disorders.

Compounds

In one aspect, provided herein are compounds according to Formula (I):

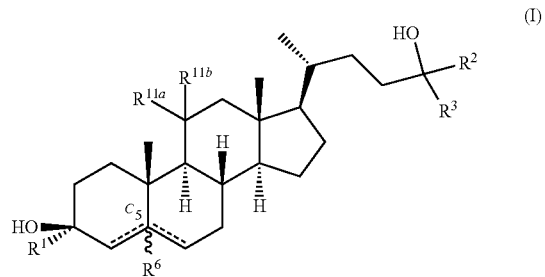

or a pharmaceutically acceptable salt thereof, wherein:

$R^1$ is hydrogen or $C_1$-$C_6$ alkyl; each of $R^2$ and $R^3$ is independently hydrogen, $C_1$-$C_6$ alkyl, or carbocyclyl, or $R^2$ and $R^3$, together with the carbon atom to which they are attached, form a 3-8 membered ring; $R^6$ is absent or hydrogen; $R^{11a}$ is hydrogen or $C_1$-$C_6$ alkyl (e.g., methyl) and $R^{11b}$ is —OH, or $C_1$-$C_6$ alkyl, or $R^{11a}$ and $R^{11b}$ are joined together to form oxo; and ==== represents a single or double bond, wherein when one ==== is a double bond, the other ==== is a single bond; and when one of the ==== is a double bond, $R^6$ is absent.

In some embodiments, $R^{11a}$ and $R^{11b}$ are not joined together to form oxo.

In some embodiments, $R^1$ is $C_{1-6}$ alkyl. In some embodiments, $R^1$ is hydrogen, methyl or ethyl, —CHF$_2$, —CF$_3$, —CH$_2$OCH$_3$, or —CH$_2$OCH$_2$CH$_3$. In some embodiments, $R^1$ is unsubstituted $C_{1-6}$ alkyl (e.g., —CH$_3$ or —CH$_2$CH$_3$). In some embodiments, $R^1$ is hydrogen. In some embodiments, $R^1$ is —CH$_3$. In some embodiments, $R^1$ is —CH$_2$CH$_3$.

In some embodiments, each of $R^2$ and $R^3$ is independently hydrogen, methyl, ethyl, propyl, isopropyl, cyclopropyl, butyl (e.g., tert-butyl), —CF$_3$, or —CH$_2$CF$_3$. In some embodiments, each of $R^2$ and $R^3$ is independently methyl, isopropyl, or tert-butyl.

In some embodiments, $R^2$ is hydrogen, methyl, ethyl, or —CF$_3$.

In some embodiments, $R^3$ is methyl, ethyl, propyl, isopropyl, cyclopropyl, butyl (e.g., tert-butyl), —CF$_3$, or —CH$_2$CF$_3$.

In some embodiments, $R^{11a}$ is hydrogen and $R^{11b}$ is —OH. In some embodiments, $R^{11b}$ is $C_1$-$C_6$ alkyl (e.g., methyl) and $R^{11b}$ is —OH. In some embodiments, $R^{11a}$ and $R^{11b}$ are joined together to form oxo.

In some embodiments, the compound of Formula (I) is a compound of Formula (I-A) or Formula (I-B):

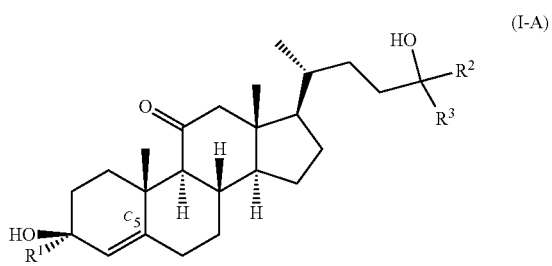

-continued (I-B)

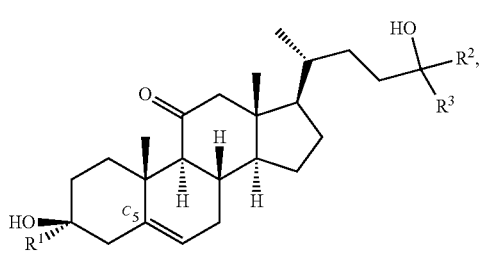

or a pharmaceutically acceptable salt thereof.

In some embodiments, each of ═══ is a single bond.

In some embodiments, the compound of Formula (I) is a compound of Formula (II):

(II)

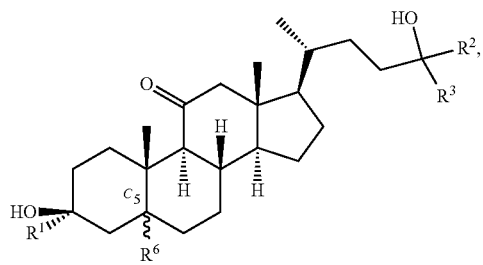

or a pharmaceutically acceptable salt thereof.

In some embodiments, the compound of Formula (II) is a compound of Formula (II-A) or Formula (II-B):

(II-A)

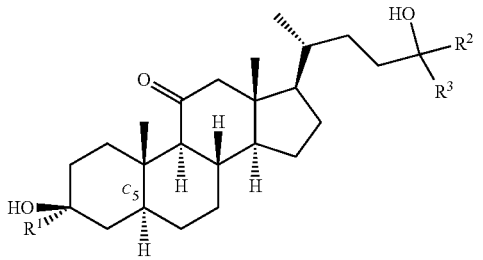

(II-B)

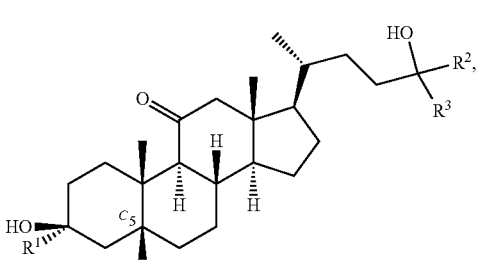

or a pharmaceutically acceptable salt thereof.

In some embodiments, $R^1$ is $C_{1-6}$ alkyl. In some embodiments, $R^1$ is hydrogen, methyl, ethyl, —CHF$_2$, —CF$_3$, —CH$_2$OCH$_3$, or —CH$_2$OCH$_2$CH$_3$.

In some embodiments, each of $R^2$ and $R^3$ is independently hydrogen, methyl, ethyl, propyl, isopropyl, cyclopropyl, butyl (e.g., tert-butyl), —CF$_3$, or —CH$_2$CF$_3$.

In some embodiments, $R^2$ is hydrogen, methyl, ethyl, or —CF$_3$.

In some embodiments, $R^3$ is methyl, ethyl, propyl, isopropyl, cyclopropyl, butyl, —CF$_3$, or —CH$_2$CF$_3$.

In an aspect, provided herein is a compound selected from the group consisting of:

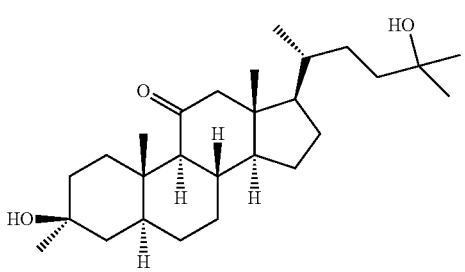

,

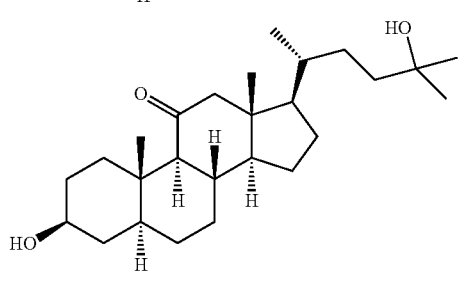

,

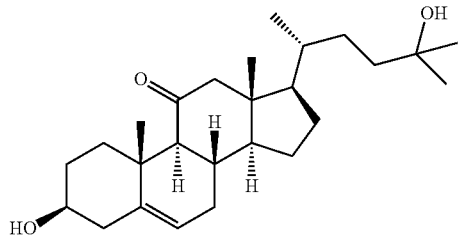

,

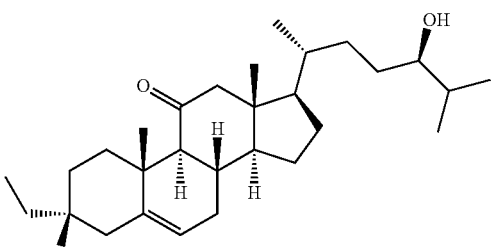

,

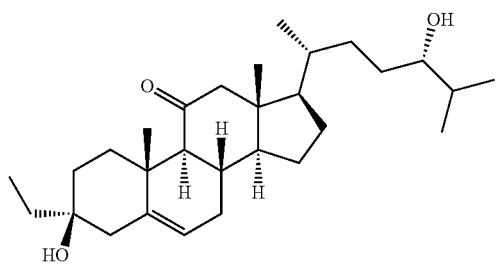

,

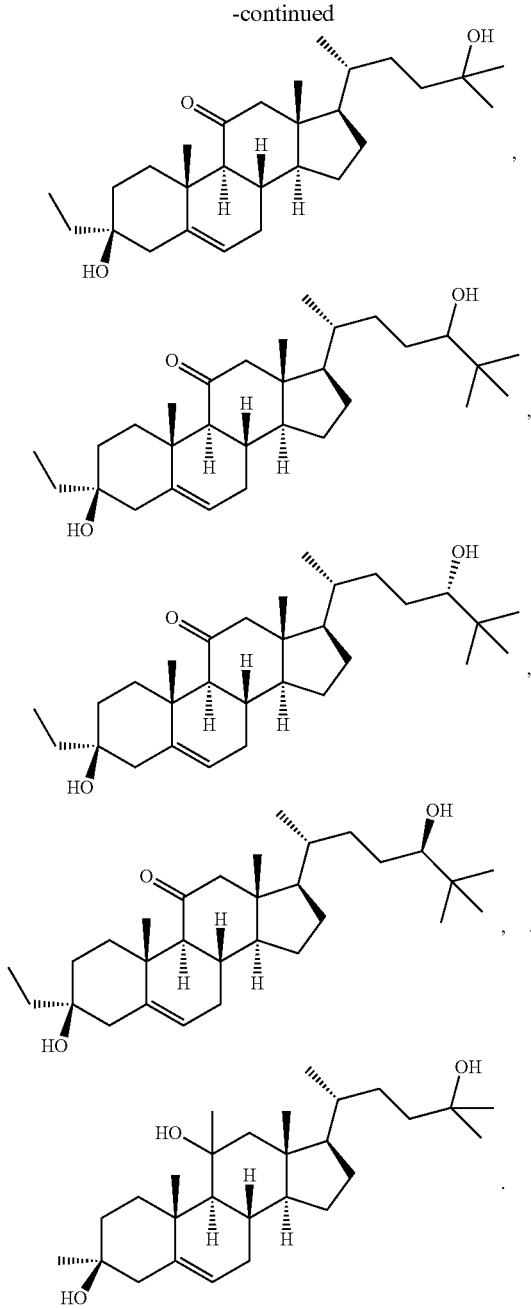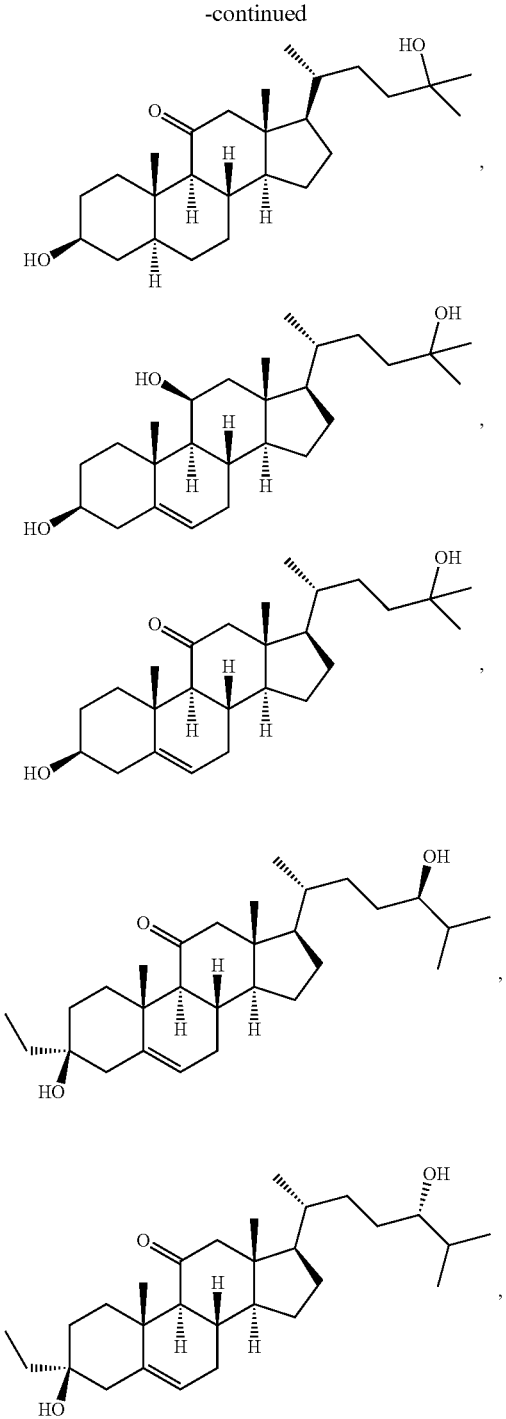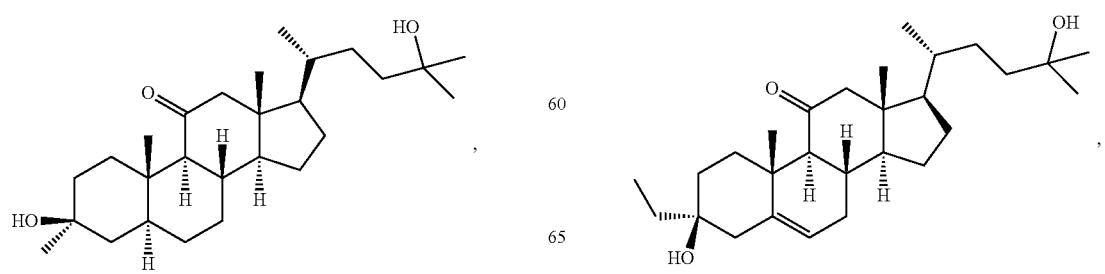
In an aspect, provided herein is a pharmaceutically acceptable salt of a compound selected from the group consisting of:

-continued

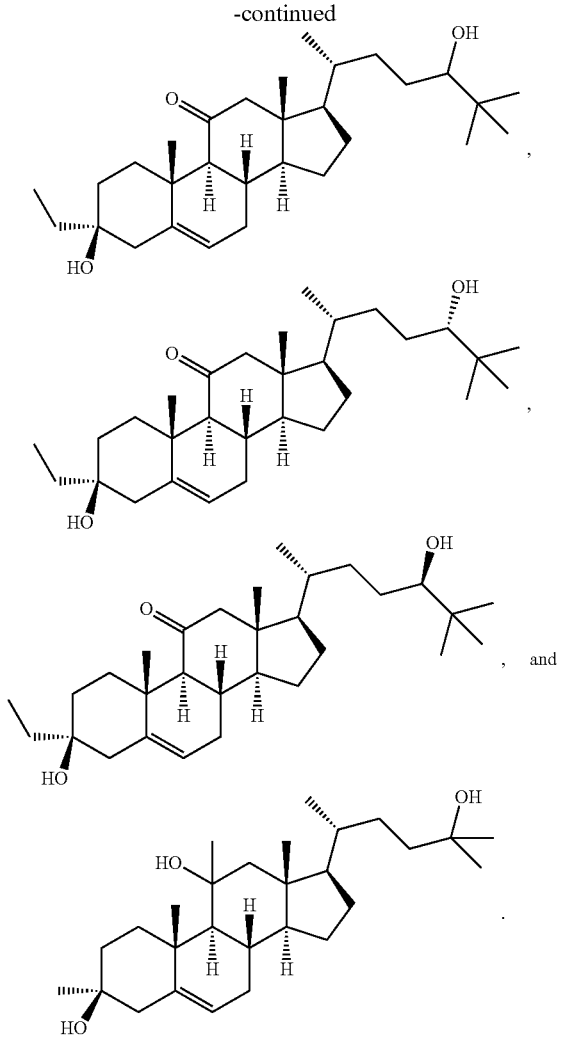
, ,
, and

.

In some embodiments, the compound of Formula (I) is a compound of Formula (III):

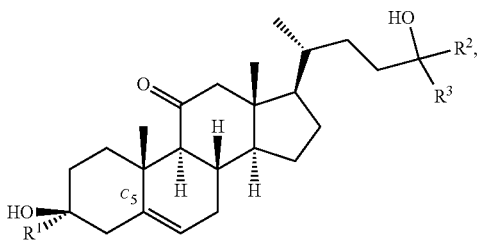
(III)

or a pharmaceutically acceptable salt thereof.

In some embodiments, $R^1$ is $C_{1-6}$ alkyl. In some embodiments, $R^1$ is hydrogen. In some embodiments, $R^1$ is —$CH_2CH_3$. In some embodiments, $R^1$ is hydrogen, methyl, ethyl, —$CHF_2$, —$CF_3$, —$CH_2OCH_3$, or —$CH_2OCH_2CH_3$.

In some embodiments, each of $R^2$ and $R^3$ is independently hydrogen, methyl, ethyl, propyl, isopropyl, cyclopropyl, butyl (e.g., tert-butyl), —$CF_3$, or —$CH_2CF_3$.

In some embodiments, $R^2$ is hydrogen, methyl, ethyl, or —$CF_3$.

In some embodiments, $R^3$ is methyl, ethyl, propyl, isopropyl, cyclopropyl, butyl (e.g., tert-butyl), —$CF_3$, or —$CH_2CF_3$.

Alternative Embodiments

In an alterative embodiment, compounds described herein may also comprise one or more isotopic substitutions. For example, hydrogen may be $^2H$ (D or deuterium) or $^3H$ (T or tritium); carbon may be, for example, $^{13}C$ or $^{14}C$; oxygen may be, for example, $^{18}O$; nitrogen may be, for example, $^{15}N$, and the like. In other embodiments, a particular isotope (e.g., $^3H$, $^{13}C$, $^{14}C$, $^{18}O$ or $^{15}N$) can represent at least 1%, at least 5%, at least 10%, at least 15%, at least 20%, at least 25%, at least 30%, at least 35%, at least 40%, at least 45%, at least 50%, at least 60%, at least 65%, at least 70%, at least 75%, at least 80%, at least 85%, at least 90%, at least 95%, at least 99%, or at least 99.9% of the total isotopic abundance of an element that occupies a specific site of the compound.

Pharmaceutical Compositions

In another aspect, the invention provides a pharmaceutical composition comprising a pharmaceutically acceptable carrier and an effective amount of a compound of Formula (I).

When employed as pharmaceuticals, the compounds provided herein are typically administered in the form of a pharmaceutical composition. Such compositions can be prepared in a manner well known in the pharmaceutical art and comprise at least one active compound.

In one embodiment, with respect to the pharmaceutical composition, the carrier is a parenteral carrier, oral or topical carrier.

The present invention also relates to a compound of Formula (I) or pharmaceutical composition thereof for use as a pharmaceutical or a medicament.

Generally, the compounds provided herein are administered in a therapeutically effective amount. The amount of the compound actually administered will typically be determined by a physician, in light of the relevant circumstances, including the condition to be treated, the chosen route of administration, the actual compound administered, the age, weight, and response of the individual patient, the severity of the patient's symptoms, and the like.

The pharmaceutical compositions provided herein can be administered by a variety of routes including oral, rectal, transdermal, subcutaneous, intravenous, intramuscular, and intranasal administration. Depending on the intended route of delivery, the compounds provided herein are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope provided herein.

The compounds provided herein can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The above-described components for orally administrable, injectable, or topically administrable compositions are merely representative. Other materials as well as processing techniques and the like are set forth in Part 8 of *Remington's The Science and Practice of Pharmacy,* 21st edition, 2005, Publisher: Lippincott Williams & Wilkins, which is incorporated herein by reference.

The compounds of this invention can also be administered in sustained release forms or from sustained release drug delivery systems. A description of representative sustained release materials can be found in *Remington's Pharmaceutical Sciences*.

The present invention also relates to the pharmaceutically acceptable formulations of a compound of Formula (I). In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as CAPTISOL®. See, e.g., U.S. Pat. No. 5,376,645. In certain embodiments, the formulation comprises hexapropyl-β-cyclodextrin. In a more particular embodiment, the formulation comprises hexapropyl-β-cyclodextrin (10-50% in water).

The present invention also relates to the pharmaceutically acceptable acid addition salt of a compound of Formula (I). The acid which may be used to prepare the pharmaceutically acceptable salt is that which forms a non-toxic acid addition salt, i.e., a salt containing pharmacologically acceptable anions such as the hydrochloride, hydroiodide, hydrobromide, nitrate, sulfate, bisulfate, phosphate, acetate, lactate, citrate, tartrate, succinate, maleate, fumarate, benzoate, para-toluenesulfonate, and the like.

The following formulation examples illustrate representative pharmaceutical compositions that may be prepared in accordance with this invention. The present invention, however, is not limited to the following pharmaceutical compositions.

Exemplary Formulation 1—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Exemplary Formulation 2—Capsules: A compound of Formula (I), or pharmaceutically acceptable salt thereof, may be admixed as a dry powder with a starch diluent in an approximate 1:1 weight ratio. The mixture is filled into 250 mg capsules (125 mg of active compound per capsule).

Exemplary Formulation 3—Liquid: A compound of Formula (I), or pharmaceutically acceptable salt thereof, (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then be added to produce a total volume of 5 mL.

Exemplary Formulation 4—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Exemplary Formulation 5—Injection: A compound of Formula (I), or pharmaceutically acceptable salt thereof, may be dissolved or suspended in a buffered sterile saline injectable aqueous medium to a concentration of approximately 5 mg/mL.

Exemplary Formulation 6—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 90-150 mg tablets (30-50 mg of active compound per tablet) in a tablet press.

Exemplary Formulation 7—Tablets: A compound of Formula (I), or pharmaceutically acceptable salt thereof, may be may be admixed as a dry powder with a dry gelatin binder in an approximate 1:2 weight ratio. A minor amount of magnesium stearate is added as a lubricant. The mixture is formed into 30-90 mg tablets (10-30 mg of active compound per tablet) in a tablet press.

Exemplary Formulation 8—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 0.3-30 mg tablets (0.1-10 mg of active compound per tablet) in a tablet press.

Exemplary Formulation 9—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 150-240 mg tablets (50-80 mg of active compound per tablet) in a tablet press.

Exemplary Formulation 10—Tablets: A compound of Formula (I), or pharmaceutically acceptable salt thereof, may be admixed as a dry powder with a dry gelatin binder in an approximate 1:2 weight ratio. A minor amount of magnesium stearate is added as a lubricant. The mixture is formed into 270-450 mg tablets (90-150 mg of active compound per tablet) in a tablet press.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses.

When used to prevent the onset of a CNS-disorder, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

Methods of Treatment and Use

Compounds of the present invention, e.g., a compound of Formula (I), and pharmaceutically acceptable salts thereof, as described herein, are generally designed to modulate NMDA function, and therefore to act as oxysterols for the treatment and prevention of, e.g., CNS-related conditions in a subject. In some embodiments, the compounds described herein, e.g., a compound of Formula (I), and pharmaceutically acceptable salts thereof, as described herein, are generally designed to penetrate the blood brain barrier (e.g., designed to be transported across the blood brain barrier). Modulation, as used herein, refers to, for example, the inhibition or potentiation of NMDA receptor function. In certain embodiments, the compound of Formula (I), or pharmaceutically acceptable salt thereof, acts as a negative allosteric modulator (NAM) of NMDA, and inhibit NMDA receptor function. In certain embodiments, the present invention, e.g., a compound of Formula (I), or pharmaceutically acceptable salt thereof, acts as a positive allosteric modulator (PAM) of NMDA, and potentiate NMDA receptor function. In certain embodiments, the compound of Formula (I), or pharmaceutically acceptable salt thereof, blocks or reduces the potentiation or inhibition of NMDA receptor function by a naturally-occurring substrate. Such compounds do not act as negative allosteric modulators (NAMs) or positive allosteric modulators (PAMs) of NMDA. In some embodiments, the disorder is cancer. In some embodiments, the disorder is diabetes. In some embodiments, the disorder is a sterol synthesis disorder. In some embodiments, the disorder is a gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, or colitis. In some embodiments, the disorder is inflammatory bowel disease.

Exemplary conditions related to NMDA-modulation include, but are not limited to, gastrointestinal (GI) disorder, e.g., constipation, irritable bowel syndrome (IBS), inflammatory bowel disease (IBD) (e.g., ulcerative colitis, Crohn's disease), structural disorders affecting the GI, anal disorders (e.g., hemorrhoids, internal hemorrhoids, external hemorrhoids, anal fissures, perianal abscesses, anal fistula), colon polyps, cancer, colitis, and CNS conditions, e.g., as described herein.

Exemplary conditions (e.g., CNS conditions) related to NMDA-modulation include, but are not limited to, adjustment disorders, anxiety disorders (including obsessive-compulsive disorder, posttraumatic stress disorder, social phobia, generalized anxiety disorder), cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g., Shank3)), neurodevelopmental disorders (including Rett syndrome), multiple sclerosis, sterol synthesis disorders, Smith-Lemli-Optiz syndrome, pain (including acute pain, chronic pain, and neuropathic pain), seizure disorders (including status epilepticus and monogenic forms of epilepsy such as Dravet's disease, Tuberous Sclerosis Complex (TSC), and infantile spasms), stroke, subarachnoid hemorrhage, intracerebral hemorrhage, cerebral ischemia, traumatic brain injury, movement disorders (including Huntington's disease and Parkinson's disease) attention deficit disorder, attention deficit hyperactivity disorder, metabolic encephalopathies (including phenylketoneuria), post-partum psychosis, syndromes associated with high titers of anti-NMDA receptor antibodies (including anti-NMDA receptor encephalitis), neurodegenerative disorders, neuroinflammation, neuropsychiatric lupus, Niemann-Pick C disorder, and tinnitus.

In certain embodiments, compounds of the present invention, e.g., a compound of Formula (I), or pharmaceutically acceptable salt thereof, can be used to induce sedation or anesthesia.

In certain embodiments, the compound of Formula (I), or pharmaceutically acceptable salt thereof, is useful in the treatment or prevention of adjustment disorders, anxiety disorders (including obsessive-compulsive disorder, post-traumatic stress disorder, social phobia, generalized anxiety disorder), cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), dissociative disorders, eating disorders, mood disorders (including depression (e.g., postpartum depression), bipolar disorder, dysthymic disorder, suicidality), schizophrenia or other psychotic disorders (including schizoaffective disorder), sleep disorders (including insomnia), substance abuse-related disorders, personality disorders (including obsessive-compulsive personality disorder), autism spectrum disorders (including those involving mutations to the Shank group of proteins (e.g., Shank3)), neurodevelopmental disorders (including Rett syndrome), multiple sclerosis, sterol synthesis disorders, Smith-Lemli-Optiz syndrome, pain (including acute pain, chronic pain, and neuropathic pain), seizure disorders (including status epilepticus and monogenic forms of epilepsy such as Dravet's disease, Tuberous Sclerosis Complex (TSC), and infantile spasms), stroke, subarachnoid hemorrhage, intracerebral hemorrhage, cerebral ischemia, traumatic brain injury, movement disorders (including Huntington's disease and Parkinson's disease) attention deficit disorder, attention deficit hyperactivity disorder, metabolic encephalopathies (including phenylketoneuria), post-partum psychosis, syndromes associated with high titers of anti-NMDA receptor antibodies (including anti-NMDA receptor encephalitis), neurodegenerative disorders, neuroinflammation, neuropsychiatric lupus, Niemann-Pick C disorder, and tinnitus.

In certain embodiments, the compound of Formula (I), or pharmaceutically acceptable salt thereof, is useful in the treatment or prevention of adjustment disorders, anxiety disorders (including obsessive-compulsive disorder, post-traumatic stress disorder, social phobia, generalized anxiety disorder), cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), substance abuse-related disorders, dissociative disorders, eating disorders mood disorders (including depression (e.g., postpartum depression), bipolar disorder, dysthymic disorder, suicidality), schizophrenia or other psychotic disorders (including schizoaffective disorder), personality disorders (including obsessive-compulsive personality disorder), autism spectrum disorders (including those involving mutations to the Shank group of proteins (e.g., Shank3)), or post-partum psychosis.

In certain embodiments, the compound of Formula (I), or pharmaceutically acceptable salt thereof, is useful in the treatment or prevention of neurodevelopmental disorders (including Rett syndrome), multiple sclerosis, sterol synthesis disorders, Smith-Lemli-Optiz syndrome, pain (including acute pain, chronic pain, and neuropathic pain), seizure disorders (including status epilepticus and monogenic forms of epilepsy such as Dravet's disease, Tuberous Sclerosis Complex (TSC), and infantile spasms), stroke, subarachnoid hemorrhage, intracerebral hemorrhage, cerebral ischemia, traumatic brain injury, movement disorders (including Huntington's disease and Parkinson's disease) attention deficit disorder, attention deficit hyperactivity disorder, metabolic encephalopathies (including phenylketoneuria), syndromes associated with high titers of anti-NMDA receptor antibodies (including anti-NMDA receptor encephalitis), neurodegenerative disorders, neuroinflammation, neuropsychiatric lupus, Niemann-Pick C disorder, or tinnitus.

In some embodiments, a compound of the invention, e.g., a compound of Formula (I) that acts as a PAM of NMDA receptor function can be useful in the treatment or prevention of conditions (e.g., CNS-related conditions) including schizophrenia or other psychotic disorders (including schizoaffective disorder), sleep disorders (including insomnia), autism spectrum disorders (including those involving mutations to the Shank group of proteins (e.g., Shank3)), multiple sclerosis, movement disorders (including Huntington's disease and Parkinson's disease), attention deficit disorder, attention deficit hyperactivity disorder, metabolic encephalopathies (including phenylketoneuria), post-partum psychosis, and syndromes associated with high titers or anti-NMDA receptor antibodies (including anti-NMDA receptor encephalitis).

In some embodiments, a compound of the invention, e.g., a compound of Formula (I), that acts as a NAM of NMDA receptor function can be useful in the treatment or prevention of conditions (e.g., CNS-related conditions) including anxiety disorders (including obsessive-compulsive disorder, posttraumatic stress disorder, social phobia, generalized anxiety disorder), mood disorders (including depression (e.g., postpartum depression), bipolar disorder, dysthymic disorder, suicidality), personality disorders (including obsessive-compulsive personality disorder), neurodevelopmental disorders (including Rett syndrome), pain (including acute and chronic pain), seizure disorders (including status epilepticus and monogenic forms of epilepsy such as Dravet's disease, and Tuberous Sclerosis Complex (TSC)), stroke, traumatic brain injury, adjustment disorders, neuropsychiatric lupus, and tinnitus.

In some embodiments, a compound of the invention, e.g., a compound of Formula (I), that acts as a PAM or a NAM of NMDA receptor function can be useful in the treatment or prevention of conditions (e.g., CNS-related conditions) including cognitive disorders (including Alzheimer's disease and other forms of dementia including cortico-basal dementia-progressive supranucelar palsy, frontal-temoral dementia, primary progressive aphasia, Parkinson's disease dementia, and Lewy body dementia), sterol synthesis disorders, and eating disorders.

In another aspect, provided is a method of treating or preventing brain excitability in a subject susceptible to or afflicted with a condition associated with brain excitability, comprising administering to the subject an effective amount of a compound of the present invention, e.g., a compound of Formula (I), or a pharmaceutically acceptable salt thereof. In yet another aspect, the present invention provides a combination of a compound of the present invention, e.g., a compound of Formula (I), or pharmaceutically acceptable salt thereof, and another pharmacologically active agent. The compounds provided herein can be administered as the sole active agent or they can be administered in combination with other agents. Administration in combination can proceed by any technique apparent to those of skill in the art including, for example, separate, sequential, concurrent and alternating administration.

Movement Disorders

Also described herein are methods for treating a movement disorder. As used herein, "movement disorders" refers to a variety of diseases and disorders that are associated with hyperkinetic movement disorders and related abnormalities in muscle control. Exemplary movement disorders include, but are not limited to, Parkinson's disease and parkinsonism (defined particularly by bradykinesia), dystonia, chorea and Huntington's disease, ataxia, tremor (e.g., essential tremor), myoclonus and startle, tics and Tourette syndrome, Restless legs syndrome, stiff person syndrome, and gait disorders.

Tremor is an involuntary, at times rhythmic, muscle contraction and relaxation that can involve oscillations or twitching of one or more body parts (e.g., hands, arms, eyes, face, head, vocal folds, trunk, legs). Tremor includes hereditary, degenerative, and idiopathic disorders such as Wilson's disease, Parkinson's disease, and essential tremor, respectively; metabolic diseases (e.g., thyoid-parathyroid-, liver disease and hypoglycemia); peripheral neuropathies (associated with Charcot-Marie-Tooth, Roussy-Levy, diabetes mellitus, complex regional pain syndrome); toxins (nicotine, mercury, lead, CO, Manganese, arsenic, toluene); drug-induced (narcoleptics, tricyclics, lithium, cocaine, alcohol, adrenaline, bronchodilators, theophylline, caffeine, steroids, valproate, amiodarone, thyroid hormones, vincristine); and psychogenic disorders. Clinical tremor can be classified into physiologic tremor, enhanced physiologic tremor, essential tremor syndromes (including classical essential tremor, primary orthostatic tremor, and task- and position-specific tremor), dystonic tremor, parkinsonian tremor, cerebellar tremor, Holmes' tremor (i.e., rubral tremor), palatal tremor, neuropathic tremor, toxic or drug-induced tremor, and psychogenic tremor. Other forms of tremor include cerebellar tremor or intention tremor, dystonic tremor, essential tremor, orthostatic tremor, parkinsonian tremor, physiological tremor, psychogenic tremor, or rubral tremor.

Cerebellar tremor or intention tremor is a slow, broad tremor of the extremities that occurs after a purposeful movement. Cerebellar tremor is caused by lesions in or damage to the cerebellum resulting from, e.g., tumor, stroke, disease (e.g., multiple sclerosis, an inherited degenerative disorder).

Dystonic tremor occurs in individuals affected by dystonia, a movement disorder in which sustained involuntary muscle contractions cause twisting and repetitive motions and/or painful and abnormal postures or positions. Dystonic tremor may affect any muscle in the body. Dystonic tremors occurs irregularly and often can be relieved by complete rest.

Essential tremor or benign essential tremor is the most common type of tremor. Essential tremor may be mild and nonprogressive in some, and may be slowly progressive, starting on one side of the body but affect both sides within 3 years. The hands are most often affected, but the head, voice, tongue, legs, and trunk may also be involved. Tremor frequency may decrease as the person ages, but severity may increase. Heightened emotion, stress, fever, physical exhaustion, or low blood sugar may trigger tremors and/or increase their severity. Symptoms generally evolve over time and can be both visible and persistent following onset.

Orthostatic tremor is characterized by fast (e.g., greater than 12 Hz) rhythmic muscle contractions that occurs in the legs and trunk immediately after standing. Cramps are felt in the thighs and legs and the patient may shake uncontrollably when asked to stand in one spot. Orthostatic tremor may occurs in patients with essential tremor.

Parkinsonian tremor is caused by damage to structures within the brain that control movement. Parkinsonian tremor is often a precursor to Parkinson's disease and is typically seen as a "pill-rolling" action of the hands that may also affect the chin, lips, legs, and trunk. Onset of parkinsonian tremor typically begins after age 60. Movement starts in one limb or on one side of the body and can progress to include the other side.

Physiological tremor can occur in normal individuals and have no clinical significance. It can be seen in all voluntary muscle groups. Physiological tremor can be caused by certain drugs, alcohol withdrawal, or medical conditions including an overactive thyroid and hypoglycemia. The tremor classically has a frequency of about 10 Hz.

Psychogenic tremor or hysterical tremor can occur at rest or during postural or kinetic movement. Patient with psychogenic tremor may have a conversion disorder or another psychiatric disease.

Rubral tremor is characterized by coarse slow tremor which can be present at rest, at posture, and with intention. The tremor is associated with conditions that affect the red nucleus in the midbrain, classical unusual strokes.

Parkinson's Disease affects nerve cells in the brain that produce dopamine. Symptoms include muscle rigidity, tremors, and changes in speech and gait. Parkinsonism is characterized by tremor, bradykinesia, rigidity, and postural instability. Parkinsonism shares symptoms found in Parkinson's Disease, but is a symptom complex rather than a progressive neurodegenerative disease.

Dystonia is a movement disorder characterized by sustained or intermittent muscle contractions causing abnormal, often repetitive movements or postures. Dystonic movements can be patterned, twisting, and may be tremulous. Dystonia is often initiated or worsened by voluntary action and associated with overflow muscle activation.

Chorea is a neurological disorder characterized by jerky involuntary movements typically affecting the shoulders, hips, and face.

Huntington's Disease is an inherited disease that causes nerve cells in the brain to waste away. Symptoms include uncontrolled movements, clumsiness, and balance problems. Huntington's disease can hinder walk, talk, and swallowing.

Ataxia refers to the loss of full control of bodily movements, and may affect the fingers, hands, arms, legs, body, speech, and eye movements.

Myoclonus and Startle is a response to a sudden and unexpected stimulus, which can be acoustic, tactile, visual, or vestibular.

Tics are an involuntary movement usually onset suddenly, brief, repetitive, but non-rhythmical, typically imitating normal behavior and often occurring out of a background of normal activity. Tics can be classified as motor or vocal, motor tics associated with movements while vocal tics associated with sound. Tics can be characterized as simple or complex. For example simple motor tics involve only a few muscles restricted to a specific body part.

Tourette Syndrome is an inherited neuropsychiatric disorder with onset in childhood, characterized by multiple motor tics and at least one vocal tic.

Restless Legs Syndrome is a neurologic sensorimotor disorder characterized by an overwhelming urge to move the legs when at rest.

Stiff Person Syndrome is a progressive movement disorder characterized by involuntary painful spasms and rigidity of muscles, usually involving the lower back and legs. Stiff-legged gait with exaggerated lumbar hyperlordosis typically results. Characteristic abnormality on EMF recordings with continuous motor unit activity of the paraspinal axial muscles is typically observed. Variants include "stiff-limb syndrome" producing focal stiffness typically affecting distal legs and feet.

Gait disorders refer to an abnormality in the manner or style of walking, which results from neuromuscular, arthritic, or other body changes. Gait is classified according to the system responsible for abnormal locomotion, and include hemiplegic gait, diplegia gait, neuropathic gait, myopathic gait, parkinsonian gait, choreiform gait, ataxic gait, and sensory gait.

Mood Disorders

Also provided herein are methods for treating a mood disorder, for example clinical depression, postnatal depression or postpartum depression, perinatal depression, atypical depression, melancholic depression, psychotic major depression, catatonic depression, seasonal affective disorder, dysthymia, double depression, depressive personality disorder, recurrent brief depression, minor depressive disorder, bipolar disorder or manic depressive disorder, depression caused by chronic medical conditions, treatment-resistant depression, refractory depression, suicidality, suicidal ideation, or suicidal behavior.

Clinical depression is also known as major depression, major depressive disorder (MDD), severe depression, unipolar depression, unipolar disorder, and recurrent depression, and refers to a mental disorder characterized by pervasive and persistent low mood that is accompanied by low self-esteem and loss of interest or pleasure in normally enjoyable activities. Some people with clinical depression have trouble sleeping, lose weight, and generally feel agitated and irritable. Clinical depression affects how an individual feels, thinks, and behaves and may lead to a variety of emotional and physical problems. Individuals with clinical depression may have trouble doing day-to-day activities and make an individual feel as if life is not worth living.

Postnatal depression (PND) is also referred to as postpartum depression (PPD), and refers to a type of clinical depression that affects women after childbirth. Symptoms can include sadness, fatigue, changes in sleeping and eating habits, reduced sexual desire, crying episodes, anxiety, and irritability. In some embodiments, the PND is a treatment-resistant depression (e.g., a treatment-resistant depression as described herein). In some embodiments, the PND is refractory depression (e.g., a refractory depression as described herein).

In some embodiments, a subject having PND also experienced depression, or a symptom of depression during pregnancy. This depression is referred to herein as) perinatal depression. In an embodiment, a subject experiencing perinatal depression is at increased risk of experiencing PND.

Atypical depression (AD) is characterized by mood reactivity (e.g., paradoxical anhedonia) and positivity, significant weight gain or increased appetite. Patients suffering from AD also may have excessive sleep or somnolence (hypersomnia), a sensation of limb heaviness, and significant social impairment as a consequence of hypersensitivity to perceived interpersonal rejection.

Melancholic depression is characterized by loss of pleasure (anhedonia) in most or all activities, failures to react to pleasurable stimuli, depressed mood more pronounced than that of grief or loss, excessive weight loss, or excessive guilt.

Psychotic major depression (PMD) or psychotic depression refers to a major depressive episode, in particular of melancholic nature, where the individual experiences psychotic symptoms such as delusions and hallucinations.

Catatonic depression refers to major depression involving disturbances of motor behavior and other symptoms. An individual may become mute and stuporose, and either is immobile or exhibits purposeless or bizarre movements.

Seasonal affective disorder (SAD) refers to a type of seasonal depression wherein an individual has seasonal patterns of depressive episodes coming on in the fall or winter.

Dysthymia refers to a condition related to unipolar depression, where the same physical and cognitive problems are evident. They are not as severe and tend to last longer (e.g., at least 2 years).

Double depression refers to fairly depressed mood (dysthymia) that lasts for at least 2 years and is punctuated by periods of major depression.

Depressive Personality Disorder (DPD) refers to a personality disorder with depressive features.

Recurrent Brief Depression (RBD) refers to a condition in which individuals have depressive episodes about once per month, each episode lasting 2 weeks or less and typically less than 2-3 days.

Minor depressive disorder or minor depression refers to a depression in which at least 2 symptoms are present for 2 weeks.

Bipolar disorder or manic depressive disorder causes extreme mood swings that include emotional highs (mania or hypomania) and lows (depression). During periods of mania the individual may feel or act abnormally happy, energetic, or irritable. They often make poorly thought out decisions with little regard to the consequences. The need for sleep is usually reduced. During periods of depression there may be crying, poor eye contact with others, and a negative outlook on life. The risk of suicide among those with the disorder is high at greater than 6% over 20 years, while self harm occurs in 30-40%. Other mental health issues such as anxiety disorder and substance use disorder are commonly associated with bipolar disorder.

Depression caused by chronic medical conditions refers to depression caused by chronic medical conditions such as cancer or chronic pain, chemotherapy, chronic stress.

Treatment-resistant depression refers to a condition where the individuals have been treated for depression, but the symptoms do not improve. For example, antidepressants or physchological counseling (psychotherapy) do not ease depression symptoms for individuals with treatment-resistant depression. In some cases, individuals with treatment-resistant depression improve symptoms, but come back. Refractory depression occurs in patients suffering from depression who are resistant to standard pharmacological treatments, including tricyclic antidepressants, MAOIs, SSRIs, and double and triple uptake inhibitors and/or anxiolytic drugs, as well as non-pharmacological treatments (e.g., psychotherapy, electroconvulsive therapy, vagus nerve stimulation and/or transcranial magnetic stimulation).

Suicidality, suicidal ideation, suicidal behavior refers to the tendency of an individual to commit suicide. Suicidal ideation concerns thoughts about or an unusual preoccupation with suicide. The range of suicidal ideation varies greatly, from e.g., fleeting thoughts to extensive thoughts, detailed planning, role playing, incomplete attempts. Symptoms include talking about suicide, getting the means to commit suicide, withdrawing from social contact, being preoccupied with death, feeling trapped or hopeless about a situation, increasing use of alcohol or drugs, doing risky or self-destructive things, saying goodbye to people as if they won't be seen again.

Symptoms of depression include persistent anxious or sad feelings, feelings of helplessness, hopelessness, pessimism, worthlessness, low energy, restlessness, difficulty sleeping, sleeplessness, irritability, fatigue, motor challenges, loss of interest in pleasurable activities or hobbies, loss of concentration, loss of energy, poor self-esteem, absence of positive thoughts or plans, excessive sleeping, overeating, appetite loss, insomnia, self-harm, thoughts of suicide, and suicide attempts. The presence, severity, frequency, and duration of symptoms may vary on a case to case basis. Symptoms of depression, and relief of the same, may be ascertained by a physician or psychologist (e.g., by a mental state examination).

Anxiety Disorders

Provided herein are methods for treating anxiety disorders Anxiety disorder is a blanket term covering several different forms of abnormal and pathological fear and anxiety. Current psychiatric diagnostic criteria recognize a wide variety of anxiety disorders.

Generalized anxiety disorder is a common chronic disorder characterized by long-lasting anxiety that is not focused on any one object or situation. Those suffering from generalized anxiety experience non-specific persistent fear and worry and become overly concerned with everyday matters. Generalized anxiety disorder is the most common anxiety disorder to affect older adults.

In panic disorder, a person suffers from brief attacks of intense terror and apprehension, often marked by trembling, shaking, confusion, dizziness, nausea, difficulty breathing. These panic attacks, defined by the APA as fear or discomfort that abruptly arises and peaks in less than ten minutes, can last for several hours and can be triggered by stress, fear, or even exercise; although the specific cause is not always apparent. In addition to recurrent unexpected panic attacks, a diagnosis of panic disorder also requires that said attacks have chronic consequences: either worry over the attacks' potential implications, persistent fear of future attacks, or significant changes in behavior related to the attacks. Accordingly, those suffering from panic disorder experience symptoms even outside of specific panic episodes. Often, normal changes in heartbeat are noticed by a panic sufferer, leading them to think something is wrong with their heart or they are about to have another panic attack. In some cases, a heightened awareness (hypervigilance) of body functioning occurs during panic attacks, wherein any perceived physiological change is interpreted as a possible life threatening illness (i.e. extreme hypochondriasis).

Obsessive compulsive disorder is a type of anxiety disorder primarily characterized by repetitive obsessions (distressing, persistent, and intrusive thoughts or images) and compulsions (urges to perform specific acts or rituals). The OCD thought pattern may be likened to superstitions insofar as it involves a belief in a causative relationship where, in reality, one does not exist. Often the process is entirely illogical; for example, the compulsion of walking in a certain pattern may be employed to alleviate the obsession of impending harm. And in many cases, the compulsion is entirely inexplicable, simply an urge to complete a ritual triggered by nervousness. In a minority of cases, sufferers of OCD may only experience obsessions, with no overt compulsions; a much smaller number of sufferers experience only compulsions.

The single largest category of anxiety disorders is that of phobia, which includes all cases in which fear and anxiety is triggered by a specific stimulus or situation. Sufferers typically anticipate terrifying consequences from encountering the object of their fear, which can be anything from an animal to a location to a bodily fluid.

Post-traumatic stress disorder or PTSD is an anxiety disorder which results from a traumatic experience. Post-traumatic stress can result from an extreme situation, such as combat, rape, hostage situations, or even serious accident. It can also result from long term (chronic) exposure to a severe stressor, for example soldiers who endure individual battles but cannot cope with continuous combat. Common symptoms include flashbacks, avoidant behaviors, and depression.

Epilepsy

Epilepsy is a brain disorder characterized by repeated seizures over time. Types of epilepsy can include, but are not limited to generalized epilepsy, e.g., childhood absence epilepsy, juvenile nyoclonic epilepsy, epilepsy with grandmal seizures on awakening, West syndrome, Lennox-Gastaut syndrome, partial epilepsy, e.g., temporal lobe epilepsy, frontal lobe epilepsy, benign focal epilepsy of childhood.

Epileptogenesis

Epileptogenesis is a gradual process by which a normal brain develops epilepsy (a chronic condition in which seizures occur). Epileptogenesis results from neuronal damage precipitated by the initial insult (e.g., status epilepticus).

Status Epilepticus (SE)

Status epilepticus (SE) can include, e.g., convulsive status epilepticus, e.g., early status epilepticus, established status epilepticus, refractory status epilepticus, super-refractory status epilepticus; non-convulsive status epilepticus, e.g., generalized status epilepticus, complex partial status epilepticus; generalized periodic epileptiform discharges; and periodic lateralized epileptiform discharges. Convulsive status epilepticus is characterized by the presence of convulsive status epileptic seizures, and can include early status epilepticus, established status epilepticus, refractory status epilepticus, super-refractory status epilepticus. Early status epilepticus is treated with a first line therapy. Established status epilepticus is characterized by status epileptic seizures which persist despite treatment with a first line therapy, and a second line therapy is administered. Refractory status epilepticus is characterized by status epileptic seizures which persist despite treatment with a first line and a second line therapy, and a general anesthetic is generally administered. Super refractory status epilepticus is characterized by status epileptic seizures which persist despite treatment with a first line therapy, a second line therapy, and a general anesthetic for 24 hours or more.

Non-convulsive status epilepticus can include, e.g., focal non-convulsive status epilepticus, e.g., complex partial non-convulsive status epilepticus, simple partial non-convulsive status epilepticus, subtle non-convulsive status epilepticus; generalized non-convulsive status epilepticus, e.g., late onset absence non-convulsive status epilepticus, atypical absence non-convulsive status epilepticus, or typical absence non-convulsive status epilepticus.

Seizure

A seizure is the physical findings or changes in behavior that occur after an episode of abnormal electrical activity in the brain. The term "seizure" is often used interchangeably with "convulsion." Convulsions are when a person's body shakes rapidly and uncontrollably. During convulsions, the person's muscles contract and relax repeatedly.

Based on the type of behavior and brain activity, seizures are divided into two broad categories: generalized and partial (also called local or focal). Classifying the type of seizure helps doctors diagnose whether or not a patient has epilepsy.

Generalized seizures are produced by electrical impulses from throughout the entire brain, whereas partial seizures are produced (at least initially) by electrical impulses in a relatively small part of the brain. The part of the brain generating the seizures is sometimes called the focus.

There are six types of generalized seizures. The most common and dramatic, and therefore the most well known, is the generalized convulsion, also called the grand-mal seizure. In this type of seizure, the patient loses consciousness and usually collapses. The loss of consciousness is followed by generalized body stiffening (called the "tonic" phase of the seizure) for 30 to 60 seconds, then by violent jerking (the "clonic" phase) for 30 to 60 seconds, after which the patient goes into a deep sleep (the "postictal" or after-seizure phase). During grand-mal seizures, injuries and accidents may occur, such as tongue biting and urinary incontinence.

Absence seizures cause a short loss of consciousness (just a few seconds) with few or no symptoms. The patient, most often a child, typically interrupts an activity and stares blankly. These seizures begin and end abruptly and may occur several times a day. Patients are usually not aware that they are having a seizure, except that they may be aware of "losing time."

Myoclonic seizures consist of sporadic jerks, usually on both sides of the body. Patients sometimes describe the jerks as brief electrical shocks. When violent, these seizures may result in dropping or involuntarily throwing objects.

Clonic seizures are repetitive, rhythmic jerks that involve both sides of the body at the same time.

Tonic seizures are characterized by stiffening of the muscles.

Atonic seizures consist of a sudden and general loss of muscle tone, particularly in the arms and legs, which often results in a fall.

Seizures described herein can include epileptic seizures; acute repetitive seizures; cluster seizures; continuous seizures; unremitting seizures; prolonged seizures; recurrent seizures; status epilepticus seizures, e.g., refractory convulsive status epilepticus, non-convulsive status epilepticus seizures; refractory seizures; myoclonic seizures; tonic seizures; tonic-clonic seizures; simple partial seizures; complex partial seizures; secondarily generalized seizures; atypical absence seizures; absence seizures; atonic seizures; benign Rolandic seizures; febrile seizures; emotional seizures; focal seizures; gelastic seizures; generalized onset seizures; infantile spasms; Jacksonian seizures; massive bilateral myoclonus seizures; multifocal seizures; neonatal onset seizures; nocturnal seizures; occipital lobe seizures; post traumatic seizures; subtle seizures; Sylvan seizures; visual reflex seizures; or withdrawal seizures. In some embodiments, the seizure is a generalized seizure associated with Dravet Syndrome, Lennox-Gastaut Syndrome, Tuberous Sclerosis Complex, Rett Syndrome or PCDH19 Female Pediatric Epilepsy.

EXAMPLES

In order that the invention described herein may be more fully understood, the following examples are set forth. The synthetic and biological examples described in this application are offered to illustrate the compounds, pharmaceutical compositions, and methods provided herein and are not to be construed in any way as limiting their scope.

Materials and Methods

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include (but are not limited to) recrystallization, column chromatography, HPLC, or supercritical fluid chromatography (SFC). The following schemes are presented with details as to the preparation of representative pyrazoles that have been listed herein. The compounds provided herein may be prepared from known or commercially available starting materials and reagents by one skilled in the art of organic synthesis. Exemplary chiral columns available for use in the separation/purification of the enantiomers/diastereomers provided herein include, but are not limited to, CHIRALPAK® AD-10, CHIRALCEL® OB, CHIRALCEL® OB-H, CHIRALCEL® OD, CHIRALCEL® OD-H, CHIRALCEL® OF, CHIRALCEL® OG, CHIRALCEL® OJ and CHIRALCEL® OK.

Exemplary general method for preparative HPLC: Column: Waters RBridge prep 10 μm C18, 19*250 mm. Mobile phase: acetonitrile, water (NH$_4$HCO$_3$) (30 L water, 24 g NH$_4$HCO$_3$, 30 mL NH$_3$.H$_2$O). Flow rate: 25 mL/min Exemplary general method for analytical HPLC: Mobile phase: A: water (10 mM NH$_4$HCO$_3$), B: acetonitrile Gradient: 5%-95% B in 1.6 or 2 min Flow rate: 1.8 or 2 mL/min; Column: XBridge C18, 4.6*50 mm, 3.5 μm at 45° C.

NMDA Modulation

NMDA potentiation in mammalian cells which expressed NMDA receptors was assessed using the whole cell patch clamp to determine the PAM activity of compounds as described below. An automatic patch-clamp system can be used determine the NAM activity of compounds as described below.

Whole-Cell Patch Clamp of Mammalian Cells (Ionworks Barracuda (IWB))

The whole-cell patch-clamp technique was used to investigate the effects of positive allosteric modulating activity of test compounds on GluN1/GluN2A and GluN2B glutamate receptors expressed in mammalian cells. The results are shown in Tables 1 and 2.

HEK293 cells were transformed with adenovirus 5 DNA and transfected with cDNA encoding the human GRIN1/GRIN2A genes. Stable transfectants were selected using G418 and Zeocin-resistance genes incorporated into the expression plasmid and selection pressure maintained with G418 and Zeocin in the medium. Cells were cultured in Dulbecco's Modified Eagle Medium/Nutrient Mixture (D-MEM/F-12) supplemented with 10% fetal bovine serum, 100 µg/ml penicillin G sodium, 100 µg/ml streptomycin sulphate, 100 µg/ml Zeocin, 5 µg/ml blasticidin and 500 µg/ml G418.

Test article effects were evaluated in 8-point concentration-response format (4 replicate wells/concentration). All test and control solutions contained 0.3% DMSO and 0.01% Kolliphor® EL (C5135, Sigma). The test article formulations were loaded in a 384-well compound plate using an automated liquid handling system (SciClone ALH3000, Caliper LifeSciences). The measurements were performed using Ion Works Barracuda platform following this procedure:

Electrophysiological Procedures:
a) Intracellular solution (mM): 50 mM CsCl, 90 mM CsF, 2 mM $MgCl_2$, 5 mM EGTA, 10 mM HEPES. Adjust to pH 7.2 with CsOH.
b) Extracellular solution, HB-PS (composition in mM): NaCl, 137; KCl, 1.0; $CaCl_2$, 5; HEPES, 10; Glucose, 10; pH adjusted to 7.4 with NaOH (refrigerated until use).
c) Holding potential: −70 mV, potential during agonist/PAM application: −40 mV.

Recording Procedure:
a) Extracellular buffer will be loaded into the PPC plate wells (11 µL per well). Cell suspension will be pipetted into the wells (9 µL per well) of the PPC planar electrode.
b) Whole-cell recording configuration will be established via patch perforation with membrane currents recorded by on-board patch clamp amplifiers.
c) Two recordings (scans) will be performed. First, during pre-application of test article alone (duration of pre-application—5 min) and second, during test articles and agonist ($EC_{20}$ L-glutamate and 30 µM glycine) co-application to detect positive modulatory effects of the test article.

Test Article Administration: The first pre-application will consist of the addition of 20 µL of 2× concentrated test article solution and, second, of 20 µL of 1× concentrated test article and agonist at 10 µL/s (2 second total application time).

Potentiating Effect of Positive Allosteric Modulators (PAM) on the Channel

Potentiating effect of positive allosteric modulators (PAM) on the channel will be calculated as $$\% \text{ activation} = (I_{PAM}/I_{EC10-30}) \times 100\% - 100\%$$

where $I_{PAM}$ will be the L-glutamate $EC_{10-30}$-elicited current in presence of various concentrations of test articles and $I_{EC20}$ will be the mean current elicited with L-glutamate $EC_{20}$. PAM concentration-response data will be fitted to an equation of the form:

$$\% \text{ Activation} = \% \text{ L-glutamate } EC_{20} + \{(\% \text{ MAX} - \% \text{ L-glutamate } EC_{20})/[1+([\text{Test}]/EC_{50})^N]\}$$

where [Test] will be the concentration of PAM (test article), $EC_{50}$ will be the concentration of PAM producing half-maximal activation, N will be the Hill coefficient, % L-glutamate $EC_{20}$ will be the percentage of the current Elicited with L-glutamate $EC_{20}$, % MAX is the percentage of the current activated with the highest dose of PAM co-admitted with L-glutamate $EC_{20}$ and % Activation will be the percentage of the current elicited with L-glutamate $EC_{10-30}$ at each PAM concentration.

The maximal amplitude of the evoked currents are measured and defined as Peak Current Amplitude (PCA).

Automated Patch-Clamp System (QPatch HTX):

In this study, HEK 293 cells stably transfected with glutamate-activated channels of the GRIN1/2A subtype will be used together with submaximal NMDA concentrations (300 µM NMDA, co-application with 8 µM Glycine) to investigate the negative allosteric modulation of the test compounds.

Cell Culture

In general, cells will be passaged at a confluence of about 80% to-90%. For electrophysiological measurements cells will be harvested at a confluence of about 80% to 90% from sterile culture flasks containing culture complete medium. Cells will be transferred as suspension in PBS to the QPatch 16X or QPatch HTX system to the centrifuge/washer directly.

Standard Laboratory Conditions: Cells will be incubated at 37° C. in a humidified atmosphere with 5% $CO_2$ (rel. humidity about 95%).

Culture media: The cells will be continuously maintained in and passaged in sterile culture flasks containing a 1:1 mixture of Dulbecco's modified eagle medium and nutrient mixture F-12 (D-MEM/F-12 1×, liquid, with L-Glutamine) supplemented with 10% fetal bovine serum, 1% Penicillin/Streptomycin solution, and 50 µM AP-5 blocker.

Antibiotics: The complete medium as indicated above is supplemented with 100 ng/mL hygromycin, 15 ng/mL blasticidin and 1 ng/mL puromycin.

Induction of Expression: 2.5 ng/mL tetracycline is added 24 h before start of experiments.

Dose Formulation

Dose levels are in terms of test compounds, as supplied. Vehicle will be added to achieve a stock concentration of 10 mM (storage at −10° C. to −30° C.). A further stock solutions of 1.0 mM will be prepared in DMSO. Details of stock solution usage (thawing, dose formulations) will be documented in the raw data. The time period of stock solution usage will be detailed in the report.

Test Compound Concentrations

Dose levels are in terms of test compounds, as supplied. Vehicle will be added to achieve a stock concentration of 10 mM (storage at −10° C. to −30° C.). A further stock solutions of 1.0 mM will be prepared in DMSO. Details of stock solution usage (thawing, dose formulations) will be documented in the raw data. The time period of stock solution usage will be detailed in the report.

One test concentration of 1.0 µM will be tested.

All test solutions will be prepared by diluting the stock solutions with either Mg-free bath solution only or Mg-free bath solution containing NMDA (300 µM) and glycine (8.0 µM) shortly prior to the electrophysiological experiments and kept at room temperature (19° C. to 30° C.) when in use. 0.1% DMSO will be used as vehicle.

Frequency of preparation: For each test concentration, fresh solutions of test compounds will be prepared every day.

Stability of dose formulation: All preparation times will be documented in the raw data. Any observations regarding instability of test compounds will be mentioned in the raw data.

Storage of dose formulation: On the day of experimentation dose formulations will be maintained at room temperature (19° C. to 30° C.) when in use.

Bath Solutions

For preparing the experiments and for formation of the giga-ohm-seal, the following standard bath solution will be used:

Sodium Chloride: 137 mM; Potassium Chloride: 4 mM; Calcium Chloride: 1.8 mM; Magnesium Chloride: 1 mM; HEPES: 10 mM; D-Glucose: 10 mM; Cremophor: 0.02%; pH (NaOH): 7.4

The 1× bath solution will be prepared by diluting 10× bath solution without Glucose and 100× Glucose solution with water at least every 7 days. Both stock solutions have been prepared prior to the experimental start of the present study and stored at 1° C. to 9° C. (10× bath solution) or −10° C. to −30° (100× Glucose solution). The batch number(s) of the bath solution(s) used in the experiments will be documented in the raw data. When in use, the 1× bath solution will be kept at room temperature (19° C. to 30° C.). When not in use, the 1× bath solution will be stored at 1° C. to 9° C.

After the giga-seal was formed the following Mg-free bath solution will be used:

Sodium Chloride: 137 mM; Potassium Chloride: 4 mM; Calcium Chloride: 2.8 mM; HEPES: 10 mM; D-Glucose: 10 mM; Cremophor: 0.02%; pH (NaOH): 7.4

This Mg-free bath solution will be prepared as a 1× solution and stored at 1° C. to 9° C. It will be prepared freshly at least every 10 days.

Intracellular Solution

The 1× intracellular solution will be thawed every day out of a frozen 1× intracellular solution, which has been prepared prior to the experimental start of the present study, aliquoted and stored at −10° C. to −30° C. When in use, the 1× intracellular solution will kept at room temperature (19° C. to 30° C.). Remaining 1× intracellular solution will be stored in the fridge (1° C. to 9° C.). The 1× intracellular solution will include the components outlined below:

Potassium Chloride: 130 mM; Magnesium Chloride: 1 mM; Mg-ATP: 5 mM; HEPES: 10 mM; EGTA: 5 mM; pH (KOH): 7.2

Cell Treatment

For this study, cells will continuously be perfused with NMDA/Glycine, Test Compound or Test Compound/NMDA/Glycin.

In every case, at least 30-second prewash steps with a test compound will be performed in between applications. For details see Table A below.

Each experiment type will be analyzed in at least n=3 isolated cells. The NMDA and Glycine stock solutions will be prepared prior to the experimental start of the present study, stored frozen (−10° C. to −30° C.) until the day of experimentation. Shortly prior to the electrophysiological experiments, frozen stock solutions will be thawed and diluted.

Control: The effect of vehicle (0.1% DMSO) and D-(−)-2-Amino-5-phosphonopentanoic acid (AP-5) (100 μM) will be measured at three cells every second week, in order to assure successful expression of NMDA receptors.

The 50 mM stock solution of AP-5 has been prepared prior to the experimental start of the present study, aliquoted and stored frozen (−10° C. to −30° C.) until the day of experimentation. Shortly prior to the electrophysiological experiments the frozen stock solution will be thawed and then diluted in Mg-free bath solution containing NMDA (300 μM) and glycine (8.0 μM), to give a final perfusion concentration of 100 μM.

Experimental Procedure

Cells are transferred as suspension in serum-free medium to the QPatch HTX system and kept in the cell storage tank/stirrer during experiments. All solutions applied to cells including the intracellular solution will be maintained at room temperature (19° C. to 30° C.).

During the sealing process standard bath solution described above will be used. All solutions applied to cells including the pipette solution will be maintained at room temperature (19° C. to 30° C.). After formation of a Gigaohm seal between the patch electrodes and transfected individual HEK293 cells only Mg-free bath solution will be perfused and the cell membrane will be ruptured to assure electrical access to the cell interior (whole-cell patch-configuration). Inward currents will be measured upon application of 300 μM NMDA (and 8.0 μM Glycine) to patch-clamped cells for 5 sec. During the entire experiment the cells will be voltage-clamped at a holding potential of −80 mV.

For the analysis of test compounds, NMDA receptors will be stimulated by 300 μM NMDA and 8.0 μM Glycine and test compound combinations described below. Thirty-second prewash steps with a test compound will be performed in between applications.

TABLE A

Application Protocol; use dependence of test compounds

| Appl. # | Duration (s) | Application |
| --- | --- | --- |
| 1 | 4 | NMDA/Glycine |
| 2 | 30 | Bath |
| 3 | 4 | NMDA/Glycine |
|   |   | 2 repetitions |
| 4 | 30 | 1 μM Test Compound |
| 5 | 4 | 1 μM Test Compound + NMDA/Glycine |
|   |   | 6 repetitions |
| 6 | 30 | Bath |
| 7 | 4 | NMDA/Glycine |
|   |   | 2 repetitions |

TABLE B

Application Protocol; control experiments

| Appl. # | Duration (s) | Application |
| --- | --- | --- |
| 1 | 4 | NMDA/Glycine |
| 2 | 30 | Bath |
| 3 | 4 | NMDA/Glycine |
|   |   | 2 repetitions |
| 4 | 30 | Bath |
| 5 | 4 | NMDA/Glycine |
|   |   | 6 repetitions |
| 6 | 30 | Bath |
| 7 | 4 | NMDA/Glycine + 100 μM AP-5 |
|   |   | 2 repetitions |

Synthetic Procedures

Abbreviations

THF: tetrahydrofuran; $Na_2SO_4$: sodium sulfate; PE: petroleum ether; DCM: dichloromethane; EtOAc: ethyl acetate; PCC: pyridinium chlorochromate; DMP: Dess-Martin periodinane; TBDPS: t-butyldiphenylsilyl; TBAF: tetra-n-butylammonium fluoride; Ts: p-toluenesulfonyl; $Ac_2O$: acetic anhydride; Py: pyridine; Me: methyl; Et: ethyl; t-Bu: tert-butyl; Ph: phenyl; 9-BBN: 9-borabicyclo[3.3.1]nonane; TEA: triethylamine; BHT: 2,6-di-tert-butyl-4-methylphenol; SFC: supercritical fluid chromatography; MAD: methylaluminum bis (2, 6-di-t-butyl-4-methylphenoxide); MS: mass spectrometry; LCMS: liquid chromatography-mass spectrometry; ESI: electrospray ionization; NMR: nuclear magnetic resonance; TLC: thin layer chromatography; MeCN: acetonitrile; t-BuOK: potassium tert-butoxide.

Example 1. Synthesis of Compound 1
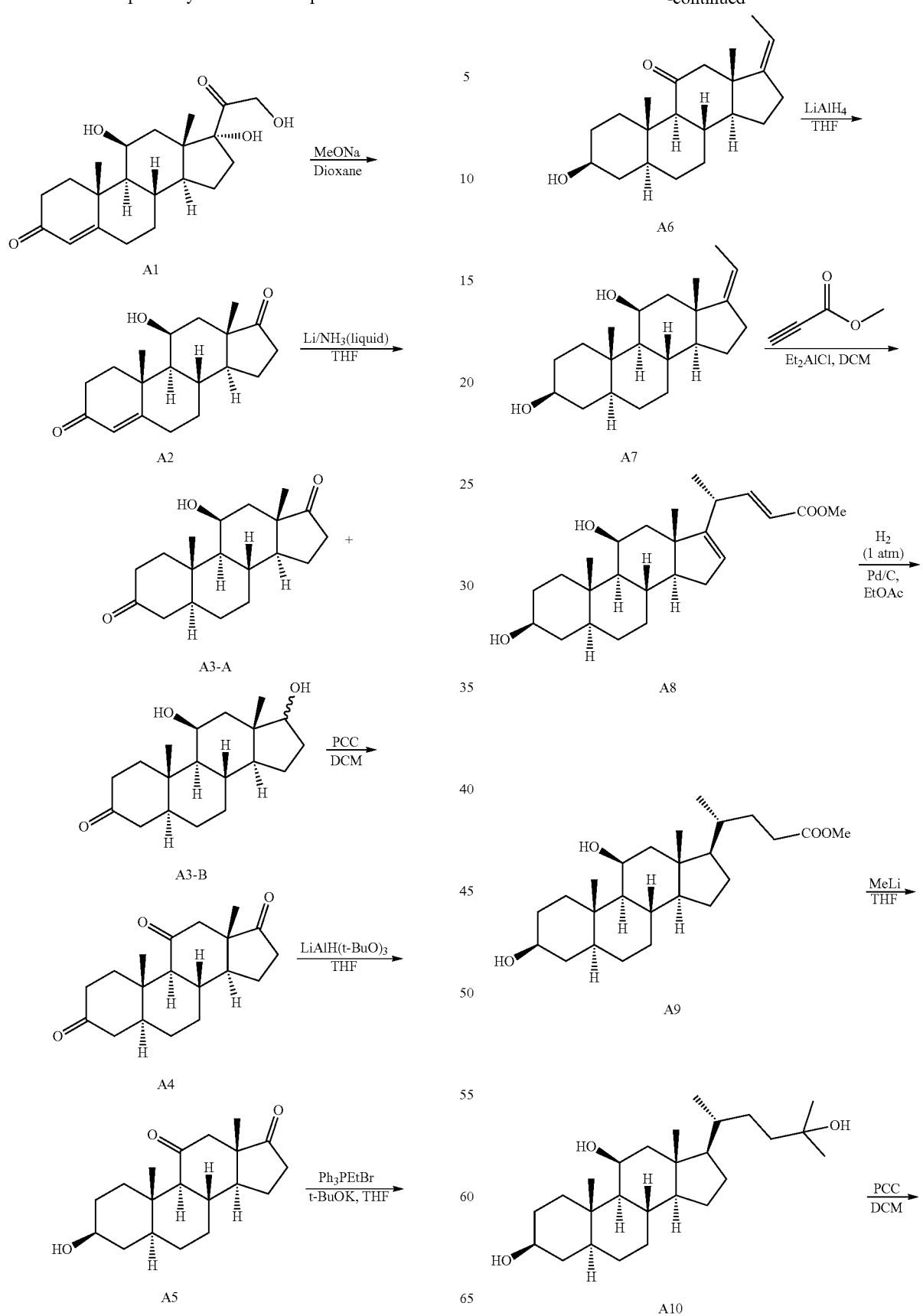

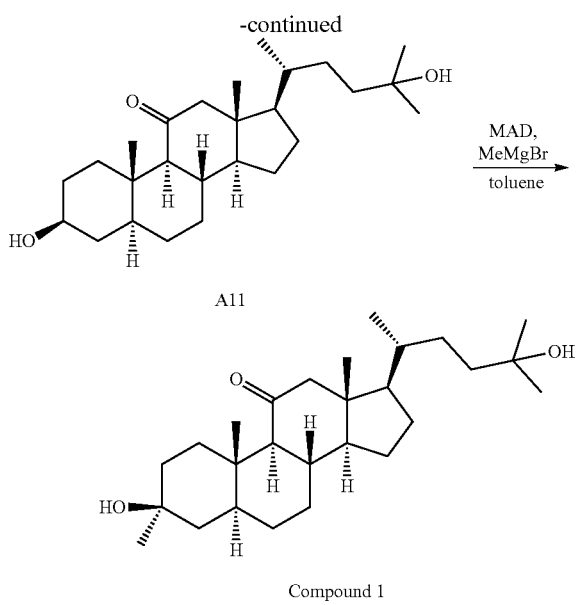

A11

Compound 1

Synthesis of Compound A2. To solution of Compound A1 (40 g, 110 mmol) in dry dioxane (1 L) under $N_2$ was added sodium methoxide (30 g, 550 mmol). The mixture was stirred at 110° C. for 16 hours, at which point TLC analysis showed the starting material was consumed. The mixture was concentrated to remove roughly ⅓ the volume of the solvent, and acidified with 2 M HCl to a pH of 5~6. The solution was then extracted with DCM (3×500 mL), washed with aqueous $NaHCO_3$ (500 mL) and brine (500 mL), dried over $Na_2SO_4$, concentrated, and purified on silica gel (PE:EtOAc:MeOH 3:1:0.1) to give Compound A2 (11 g, 33.1%) as a solid.

Synthesis of Compound A3-A and Compound A3-B. To a solution of lithium (2.5 g, 363 mmol) was added liquid ammonia (1000 mL) at −70° C. in portions. The mixture was stirred at −70° C. for 30 mins until all of the lithium was dissolved. A solution of Compound A2 (11 g, 36 mmol) and tert-BuOH (5.4 g, 72.6 mmol) in anhydrous tetrahydrofuran (400 mL) was added to the reaction dropwise, and the mixture was stirred for 90 mins until the reaction mixture turned light yellow, at which point TLC analysis indicated the starting material was consumed. Ammonium chloride (15 g) was then added, and the mixture was concentrated. The resulting residue was extracted with 0.5N HCl (500 mL) and dichloromethane (500 mL×2), and the combined organic layers were washed with saturated $NaHCO_3$, dried over $Na_2SO_4$, filtered, and concentrated to give a mixture of Compound A3-A and Compound A3-B (10 g, impure) which was used directly in the next step without further purification.

Synthesis of Compound A4. To a solution of Compound A3-A and Compound A3-B (10 g crude, 27.9 mmol) in anhydrous dichloromethane (100 mL) was added PCC (17 g, 66 mmol) and silica gel (17 g). After stirring at 25° C. for 2 h, TLC analysis indicated the starting material was consumed. The resulting solution was concentrated and purified by silica gel (PE:EtOAc 5:1 to 2:1) to afford Compound A4 (4.6 g, 46%) as a solid.

Synthesis of Compound A5. To a solution of Compound A4 (4.6 g, 15 mmol) in THF (50 mL) was slowly added a solution of LiAlH(t-BuO)$_3$ (4.2 mg, 17 mmol) in THF (20 mL) under $N_2$ at −40° C. The reaction solution was stirred at −40° C. for 15 min, at which point TLC analysis indicated the starting material was consumed. The mixture was quenched with saturated $NH_4Cl$ solution (50 mL) and extracted with EtOAc (50 mL×2). The organic layers were combined, dried over $Na_2SO_4$, concentrated, and purified by combi-flash (PE:EA 100%-50%) to afford Compound A5 (2.8 g, 61%) as a solid.

Synthesis of Compound A6. To a suspension of bromo(ethyl)-triphenylphosphorane (17 g, 46 mmol) in anhydrous THF (100 mL) under $N_2$ at 20° C. was added t-BuOK (1 M in THF, 46 mL, 46 mmol). The mixture was stirred at 60° C. for 1 h, followed by the addition of a solution of Compound A5 (2.8 g, 9.19 mmol) in anhydrous THF (50 mL). The resultant mixture was stirred at 60° C. for 16 h, at which point TLC analysis indicated the starting material was consumed. The reaction mixture was quenched with aqueous $NH_4Cl$ (100 mL), extracted with EtOAc (100 mL×3), dried over $Na_2SO_4$, filtered, concentrated, and purified by silica gel (PE:EA:DCM 10:1:1) to give Compound A7 (2.2 g, crude) as a solid.

Synthesis of Compound A7. To a solution of Compound A6 in THF (10 mL) was added LiAlH$_4$ (110 mg, 3.1 mmol). The reaction mixture was stirred at 15° C. for 30 minutes, at which point TLC analysis indicated the reaction was complete. Saturated $NH_4Cl$ (0.2 mL) was added to the reaction, and the mixture was filtered. The filtrate was concentrated to give a residue, to which was added saturated NaCl solution (10 mL), followed by extraction with DCM (3×5 mL). The combined organic phase was dried over $Na_2SO_4$ and concentrated to afford Compound A7 (0.4 g, 80%) as a solid.

Synthesis of Compound A8. To a solution of Compound A7 (0.4 g, 1.3 mmol) and methyl propiolate (260 mg, 3.1 mmol) in DCM (10 mL) was added Et$_2$AlCl (3.8 mL, 3.8 mmol, 1M in hexane) under $N_2$ at 15° C. The reaction mixture was stirred at 15° C. for 16 hours, at which point TLC analysis indicated the reaction was complete. The reaction mixture was quenched with a citric acid solution (10 mL). The resulting solution was washed with DCM (10 mL×2). The organic layers were combined, dried $Na_2SO_4$, concentrated, and purified by combi-flash (PE:EA=100%-65%) to give desired Compound A8 as a solid.

Synthesis of Compound A9. To a solution of Compound A8 in EtOAc (10 mL) was added Pd/C (wet, 10%, 0.02 g). After degassing three times with $H_2$, the reaction mixture was stirred for 16 hours at 15° C. under $H_2$ (15 Psi), after which point LCMS analysis indicated the reaction was complete. The mixture was filtered and the filtrate was concentrated to give crude Compound A9 as a solid, which was used in next step directly without further purification.

Synthesis of Compound A10. To a solution of Compound A9 (0.15 g, 0.37 mmol) in THF (10 mL) was added MeLi (1.2 mL, 1.8 mmol, 1.6 M in diethyl ether). The reaction solution was stirred at 15° C. for 1 hour, at which point TLC analysis indicated the reaction was complete. The mixture was quenched with $NH_4Cl$ solution (10 mL) and extracted with EtOAc (10 mL×2), followed by drying the combined organic phase over $Na_2SO_4$ and concentrating to give Compound A10 (0.15 g) as a solid.

Synthesis of Compound A11. To a solution of Compound A10 (150 mg, 0.37 mmol) in DCM (10 mL) was added silicon grease (150 mg) and PCC (160 mg, 0.74 mmol). The resulting reaction mixture was stirred at 15° C. for 2 hours, after which TLC analysis indicated the reaction was complete. The mixture was filtered, concentrated, and purified by combi-flash (PE:EA=100%-75%) to give Compound A11 (130 mg, 88%) as a solid. $^1$H NMR (400 MHz, CDCl$_3$) δ

2.82-2.71 (m, 1H), 2.60-2.38 (m, 3H), 2.35-2.20 (m, 3H), 2.15-1.90 (m, 3H), 1.88-1.02 (m, 23H), 0.88 (d, J=5.8 Hz, 6H), 0.64 (s, 3H).

Synthesis of Compound 1. To a solution of MAD (0.37 mmol) in toluene (5 mL) was added a solution of Compound A11 (50 mg, 0.12 mmol) in toluene (1 mL) under $N_2$ at −70° C. The mixture was stirred at −70° C. for 30 minutes, followed by addition of MeMgBr (0.12 mL, 0.37 mmol, 3M in ether) under $N_2$. The resulting mixture was stirred at −70° C. for 1 hour, at which point TLC indicated the reaction was complete. The mixture was quenched with a saturated a citric acid solution (10 mL) and extracted with EtOAc (5 mL×2). The combined organic phase was dried over $Na_2SO_4$, concentrated, and purified by combi-flash (PE: EtOAc=100%-70%) to give Compound 1 (6.5 mg, 13%) as a white solid. $^1$H NMR (400 MHz, CDCl$_3$) δ 2.53-2.50 (m, 1H), 2.45-2.35 (m, 1H), 2.25-2.22 (m, 2H), 2.10-1.90 (m, 2H), 1.80-1.05 (m, 26H), 1.00 (s, 3H), 0.95-0.80 (m, 8H), 0.62 (s, 3H). LCMS MS ESI calcd. for $C_{27}H_{47}O_3$ [M+H]$^+$ 419, found 401 [M+H−18]$^+$.

Example 2. Synthesis of Compound 2

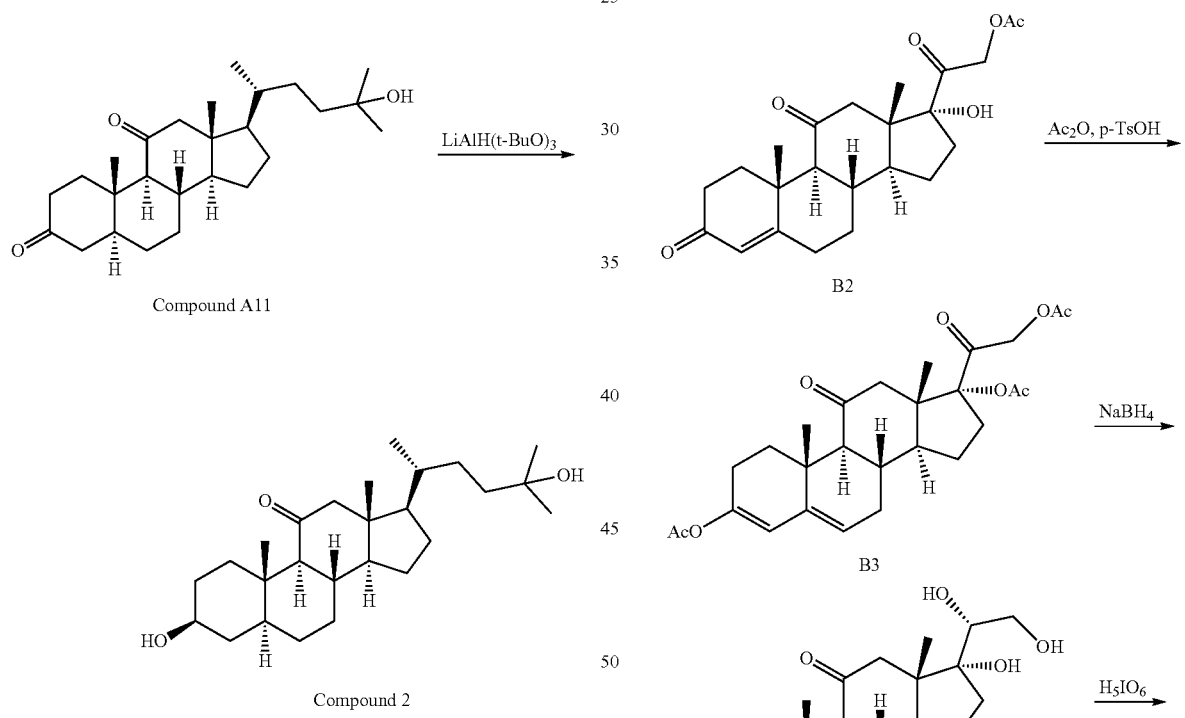

Compound A11

Compound 2

Synthesis of Compound 2. To a solution of Compound A11 (50 mg, 0.12 mmol) in THF (2 mL) was added LiAlH(t-Buo)$_3$ (47.2 mg, 0.186 mmol). The reaction mixture was stirred at 25° C. under $N_2$ for 30 min, after which TLC indicated the reaction was complete. The mixture was then quenched with saturated with NH$_4$Cl solution (5 mL) and extracted with EtOAc (3×2 mL). The combined organic phase was dried over Na$_2$SO$_4$, concentrated, and purified by silica gel to afford Compound 2 (7.5 mg, 15%) as a white solid. $^1$H NMR (400 MHz, CDCl$_3$) δ 3.65-3.49 (m, 1H), 2.50 (s, 2H), 2.29-2.15 (m, 1H), 2.09-1.90 (m, 1H), 1.85-0.97 (m, 32H), 0.93-0.76 (m, 4H), 0.62 (s, 3H). LCMS ESI calcd. for $C_{26}H_{45}O_3$ [M+H]$^+$ 405, found 387[M+H−18]$^+$.

Example 3. Synthesis of Compound 3

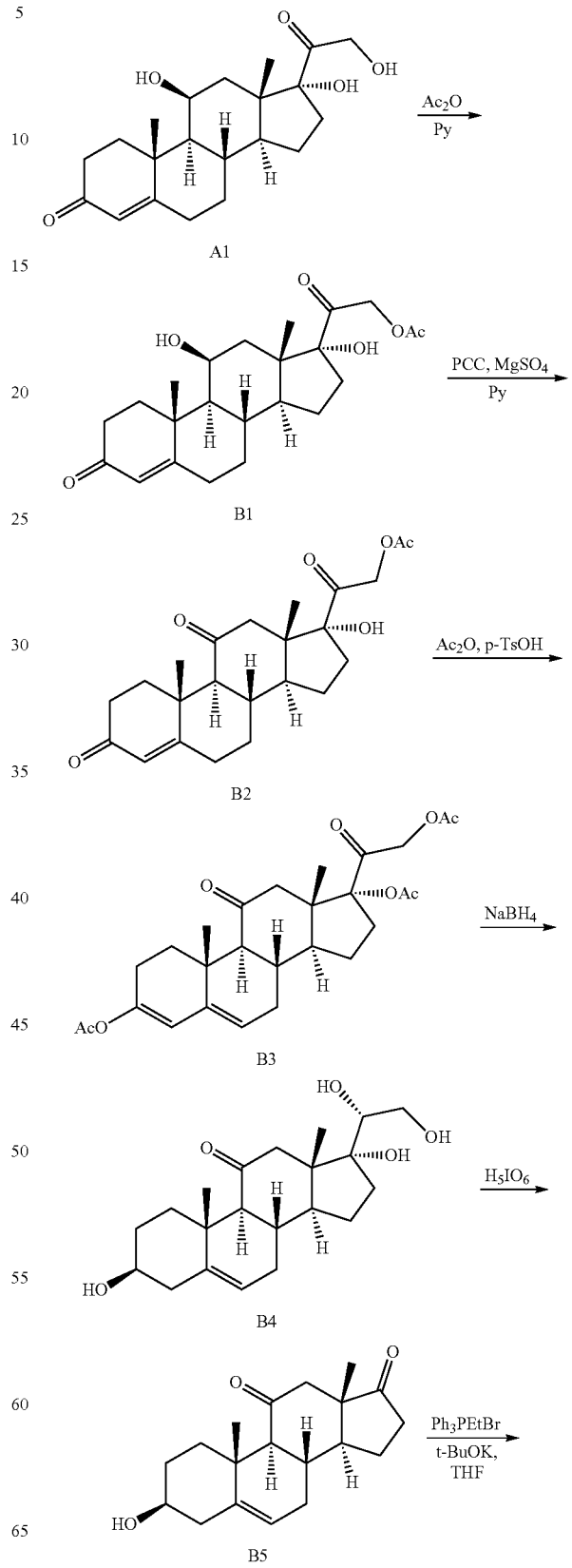

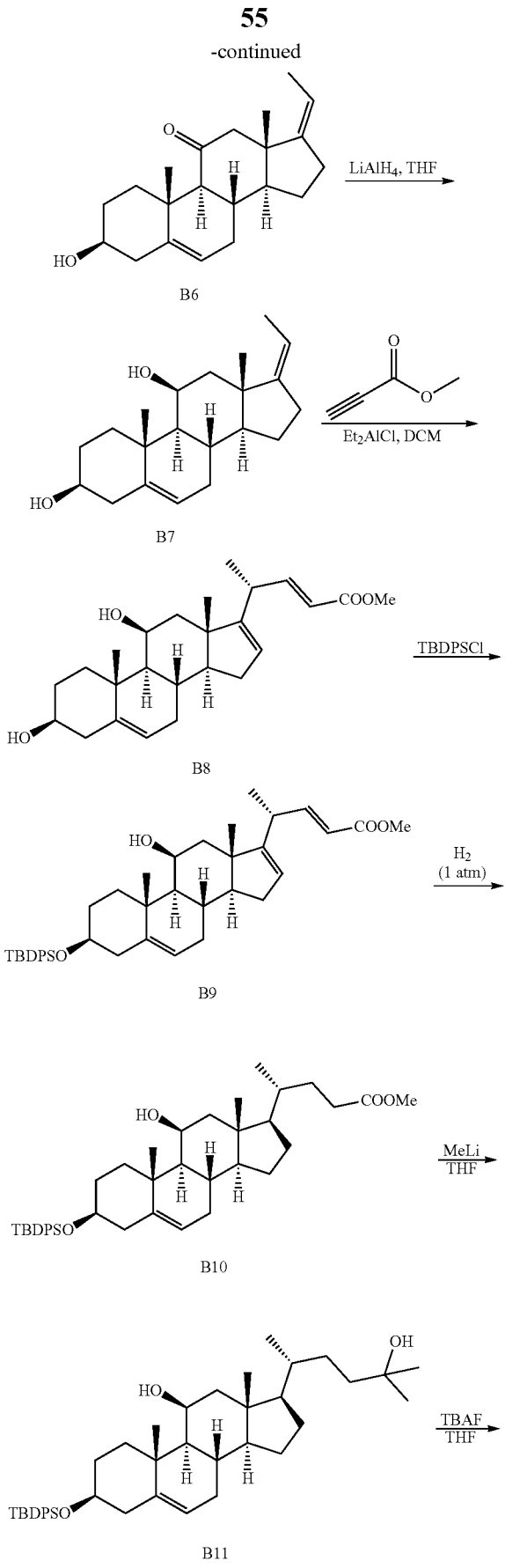

Compound 3

Synthesis of B1. To a solution of A1 (50 g, 14 mmol,) in py (500 mL) was added $Ac_2O$ (21 g, 210 mmol) dropwise at 0° C. The reaction was stirred at 25° C. for 24 hrs. The mixture was poured into 4 L of water. After stirring at 25° C. for 0.5 h, the mixture was filtered. The solid was washed with HCl (1 L, 1 M) and dried to give B1 (55 g, 99%) as a solid. $^1$H NMR (400 MHz, $CDCl_3$) δ 5.69 (s, 1H), 5.03 (d, J=17.6 Hz, 1H), 4.85 (d, J=17.6 Hz, 1H), 4.51-4.44 (brs, 1H), 2.85-2.70 (m, 1H), 2.55-2.40 (m, 2H), 2.39-2.32 (m, 1H), 2.30-1.95 (m, 9H), 1.91-1.79 (m, 2H), 1.75-1.66 (m, 2H), 1.52-1.40 (m, 5H), 1.20-0.97 (m, 3H), 0.97 (s, 3H).

Synthesis of B2. To a solution of B1 (55 g, 14 mmol) in py (1000 mL) was added $MgSO_4$ (35 g, 320 mmol) and PCC (35 g, 160 mmol) at 0° C. The reaction solution was stirred at 25° C. for 12 hrs. The mixture was filtered through Celite. The mixture was poured into 2 L of water to give a dark red suspension. After filtration, the filter cake was washed by 1M HCl (2×500 mL) and $H_2O$ (2×500 mL), and dried under vacuum at 0° C. to give B2 (38 g, 69%) as a brown powder. $^1$H NMR (400 MHz, $CDCl_3$) δ 5.73 (s, 1H), 5.13 (d, J=17.6 Hz, 1H), 4.64 (d, J=17.6 Hz, 1H), 3.05-2.98 (m, 1H), 2.92-2.85 (m, 1H), 2.85-2.70 (m, 2H), 2.55-2.21 (m, 5H), 2.16 (s, 3H), 2.02-1.88 (m, 3H), 1.87-1.45 (m, 5H), 1.48 (s, 3H), 1.38-1.21 (m, 1H), 0.66 (s, 3H).

LCMS Rt=0.601 min in 2.0 min chromatography, 30-90_2MIN_E.M, purity 77%, MS ESI calcd. for $C_{23}H_{31}O_6$ $[M+H]^+$ 403, found 403.

Synthesis of B3. To a solution of B2 (38 g, 94 mmol) in $Ac_2O$ (600 mL, 6.3 mol) was added p-TsOH (19 g, 110 mmol) at 20° C. for 6 hrs. The mixture was poured into 4 L of ice water and stirred at 20° C. for 48 hrs until a solid formed. The filtered cake was concentrated in vacuum at 80° C. to give 35 g of impure product as yellow solid. The crude product was purified by column chromatography (PE:EA=3:1-2:1) to give B3 (29.6 g, 64%) as a solid.

$^1$H NMR (400 MHz, $CDCl_3$) δ 5.70-5.65 (m, 1H), 5.39-5.33 (m, 1H), 4.81-4.68 (m 2H), 2.94-2.82 (m, 2H), 2.71-2.63 (m, 1H), 2.56-2.25 (m, 4H), 2.20-1.82 (m, 15H), 1.55-1.44 (m, 1H), 1.31-1.20 (m, 1H), 1.18 (s, 3H), 0.72 (s, 3H).

LCMS Rt=0.981 min in 2.0 min chromatography, 30-90_2MIN_E.M, purity 61%, MS ESI calcd. for $C_{25}H_{31}O_6$ $[M+H—HOAc]^+$ 427, found 427.

Syntheses of B4 and B5. To a solution of B3 (15 g, 31 mmol) in EtOH (600 mL), MeOH (60 mL) and DCM (50 mL) was slowly added $NaBH_4$ (40 g, 1.1 mol) at 0° C. The reaction mixture was stirred for 1 h at 0° C., then at 20° C. for 15 hrs. The reaction mixture was quenched by adding 600 mL of 1M HCl at 0° C. The mixture was extracted by EtOAc (2×1.5 L). The organic phase was washed with Sat. $NaHCO_3$ (300 mL), brine (200 mL), dried over $Na_2SO_4$, filtered and concentrated to give 9.3 g of crude product as a white solid. 9.3 g of crude product B4 was dissolved in 400 mL of MeOH. To this solution was added periodic acid (7 g, 36 mmol) at 0° C. After stirring for 6 hrs at 20° C., the mixture was quenched by 200 mL of 1 M HCl and extracted by 1.5 L of EtOAc. The organic phase was washed with 500 mL of saturated NaHCO$_3$, 200 mL of brine, dried over Na$_2$SO$_4$, filtered and concentrated to give B5 (6.3 g, crude) as a foaming oil, which was used for the next step without purification.

$^1$H NMR (400 MHz, CDCl$_3$) δ 5.42-5.23 (m, 1H), 3.57-3.48 (m, 1H), 3.39-3.32 (m, 1H), 2.78-2.41 (m, 2H), 2.37-2.10 (m, 4H), 1.95-1.62 (m, 6H), 1.46-0.72 (m, 11H).

LCMS Rt=0.440 min in 2.0 min chromatography, 30-90_2MIN_E.M, purity 100%, MS ESI calcd. for C$_{19}$H$_{25}$O$_2$ [M+H—H$_2$O]$^+$ 285, found 285.

Synthesis B6. To a slurry of Ph$_3$PEtBr (23 g, 62 mmol) in THF (150 mL) was added t-BuOK (7.2 g, 64 mmol) under N$_2$. After addition, the mixture was stirred at 50° C. for 30 minutes. 135 (6.3 g, 21 mmol) in THF (50 mL) was added. The mixture was stirred at 50° C. for 2 hrs. The mixture was quenched with Sat. NH$_4$Cl (200 mL) and extracted with EtOAc (2×400 mL). The combined organic phase was washed with brine (40 mL), dried over Na$_2$SO$_4$, filtered, concentrated and purified by flash column (0-20% of EtOAc in PE) to give B6 (2.7 g, impure) as an oil.

$^1$H NMR (400 MHz, CDCl$_3$) δ 5.39-5.33 (m, 1H), 5.24-5.16 (m, 1H), 3.56-3.46 (m, 1H), 2.98 (d, J=13.6 Hz, 1H), 2.58-2.06 (m, 6H), 1.99-0.92 (m, 17H), 0.86 (s, 3H).

Synthesis of B7. To a solution of B6 (2.75 g, 8.74 mmol) in THF (100 mL) was added LiAlH$_4$ (0.7 g, 18 mmol) in portions. The reaction mixture was stirred at 20° C. for 30 minutes. The reaction was quenched by 150 mL of 1M HCl at 0° C. and extracted with 400 mL of EtOAc. After the layers were separated, the organic phase was washed with 100 mL of Sat. NaHCO$_3$, 100 mL of brine, dried over NaSO$_4$ and concentrated. The residue was purified by flash column eluted with PE:EtOAc=20:1 to 4:1 to give B7 (1.7 g, 60%) as a solid.

$^1$H NMR (400 MHz, CDCl$_3$) δ 5.28-5.24 (m, 1H), 5.15-5.06 (m, 1H), 4.45-4.38 (m, 1H), 3.60-3.46 (m, 1H), 2.50-2.35 (m, 2H), 2.34-2.25 (m, 2H), 2.25-2.14 (m, 2H), 2.04-1.78 (m, 4H), 1.73-1.61 (m, 5H), 1.45-1.04 (m, 13H).

Synthesis of B8. To a solution of B7 (1.7 g, 5.2 mmol) and methyl propionate (1.3 g, 16 mmol) in DCM (70 mL) was added Et$_2$AlCl (16 mL, 16 mmol, 1 M in hexane) under N$_2$ at −20° C. The mixture was stirred at 20° C. for 4 hrs and quenched by 20 mL of Sat.NaHCO$_3$, 50 mL of saturated critic acid at 0° C. The mixture was extracted with 300 mL of EtOAc. The organic phase was washed with brine (50 mL), dried over Na$_2$SO$_4$, filtered and concentrated. The residue was purified by column chromatography and eluted with PE:EtOAc=20:1 to 2:1 to give B8 (1.4 g, 67%) as a solid.

$^1$H NMR (400 MHz, CDCl$_3$) δ 6.92 (dd, J=15.6, 7.9 Hz, 1H), 5.83 (dd, J=15.7, 1.0 Hz, 1H), 5.44-5.38 (m, 1H), 5.27-5.23 (m, 1H), 4.46-4.37 (m, 1H), 3.73 (s, 3H), 3.60-3.43 (m, 1H), 3.10-2.97 (m, 1H), 2.33-2.25 (m, 2H), 2.22-1.82 (m, 8H), 1.74-1.62 (m, 3H), 1.36-1.03 (m, 13H).

Synthesis of B9. To a solution of B8 (500 mg, 1.2 mmol) in DCM (10 mL) was added TBDPSCl (510 mg, 1.9 mmol) and imidazole (170 mg, 2.5 mmol). The mixture was stirred at 15° C. for 16 hrs. The mixture was quenched with water (20 mL) and extracted with DCM (2×10 mL). The combined organic phase was dried over Na$_2$SO$_4$, filtered, concentrated and purified by combi-flash (5% of EtOAc in PE) to give B9 (700 mg, 88%) as a solid.

$^1$H NMR (400 MHz, CDCl$_3$) δ 7.68-7.66 (m, 4H), 7.45-7.35 (m, 6H), 6.95-6.85 (m, 1H), 5.85-5.75 (m, 1H), 5.45-5.35 (m, 1H), 5.05-4.95 (m, 1H), 4.35-4.25 (m, 1H), 3.72 (s, 3H), 3.55-3.45 (m, 1H), 3.05-2.95 (m, 1H), 2.45-2.35 (m, 1H), 2.15-1.81 (m, 7H), 1.80-1.58 (m, 6H), 1.30-1.16 (m, 5H), 1.15-1.11 (m, 3H), 1.10-0.95 (m, 10H).

Synthesis of B10. To a solution of B9 (700 mg, 1.1 mmol) in MeOH (20 mL) and EtOAc (10 mL) was added Pt/C (50 mg). After degassing for three times with H$_2$, the reaction mixture was stirred for 32 hrs at 20° C. under H$_2$ balloon. The mixture was filtered and concentrated to give B10 (640 mg, 91%) as an oil.

$^1$H NMR (400 MHz, CDCl$_3$) δ 7.68-7.66 (m, 4H), 7.45-7.35 (m, 6H), 5.07-5.04 (m, 1H), 4.27-4.24 (m, 1H), 3.69 (s, 3H), 3.60-3.50 (m, 1H), 2.45-2.05 (m, 8H), 1.90-1.58 (m, 8H), 1.56-1.21 (m, 9H), 1.20-0.82 (m, 15H).

Synthesis of B11. To a solution of B10 (640 mg, 1.0 mmol) in THF (20 mL) was added MeLi (3.1 mL, 5.0 mmol, 1.6 M in THF) at 0° C. under N$_2$. After addition, the reaction mixture was stirred at 20° C. for 30 minutes. The mixture was quenched with saturated NH$_4$Cl solution (30 mL) and extracted with EtOAc (2×15 mL). The combined organic phase was dried over Na$_2$SO$_4$, filtered, concentrated and purified by combi-flash (0-10% of EtOAc in PE) to give B11 (410 mg, 64%) as an oil.

$^1$H NMR (400 MHz, CDCl$_3$) δ 7.68-7.66 (m, 4H), 7.45-7.35 (m, 6H), 5.07-5.04 (m, 1H), 4.27-4.24 (m, 1H), 3.60-3.50 (m, 1H), 2.45-2.35 (m, 1H), 2.20-2.00 (m, 2H), 1.90-1.58 (m, 10H), 1.56-1.21 (m, 14H), 1.20-1.06 (m, 9H), 1.05-0.85 (m, 13H).

Synthesis of Compound 3. B11 (350 mg, 0.54 mmol) was dissolved in TBAF (5 mL, 1M in THF). The mixture was stirred at 70° C. for 24 hrs. The reaction was quenched with saturated NH$_4$Cl solution (10 mL) and extracted with EtOAc (2×10 mL). The combined organic phase was dried over Na$_2$SO$_4$, filtered, concentrated and purified by combi-flash (0-20% of EtOAc in PE) to give Compound 3 (200 mg, 91%) as a solid.

$^1$H NMR (400 MHz, CDCl$_3$) δ 5.26-5.22 (m, 1H), 4.35-4.31 (m, 1H), 3.55-3.45 (m, 1H), 2.32-2.29 (m, 2H), 2.20-2.10 (m, 2H), 2.05-1.95 (m, 1H), 1.94-1.75 (m, 3H), 1.70-1.41 (m, 4H), 1.40-0.85 (m, 29H).

LCMS Rt=1.245 min in 2.0 min chromatography, 10-80 AB, purity 100%, MS ESI calcd. for C$_{26}$H$_{44}$O$_3$Na [M+Na]$^+$ 427, found 427.

Example 4. Synthesis of Compound 4

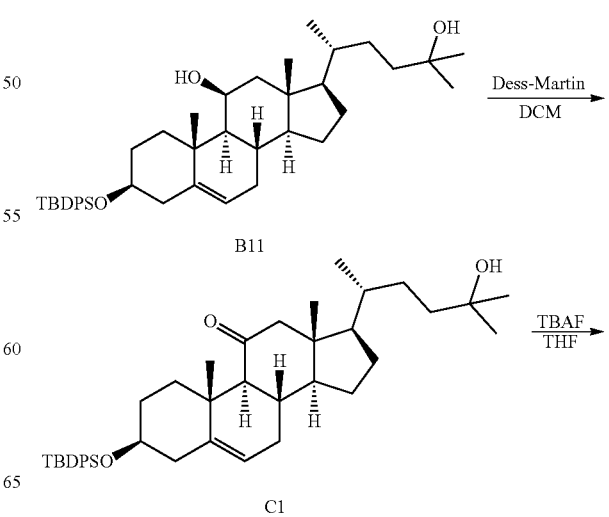

-continued

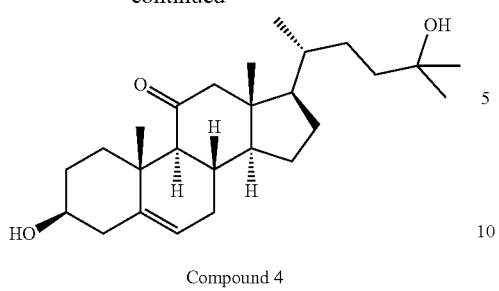

Compound 4

Synthesis of C1. To a solution of B11 (60 mg, 0.093 mmol) in DCM (5 mL) was added DMP (78 mg, 0.19 mmol). The mixture was stirred at 20° C. for 16 hrs. The mixture was quenched with saturated $Na_2SO_3$ and saturated $NaHCO_3$ (V:V=1:1, 10 mL) and extracted with DCM (2×10 mL). The combined organic phase was dried over $Na_2SO_4$, filtered and concentrated to give C1 (65 mg, crude) as an oil.

$^1$H NMR (400 MHz, $CDCl_3$) δ 7.68-7.66 (m, 4H), 7.45-7.35 (m, 6H), 5.07-5.04 (m, 1H), 3.60-3.50 (m, 1H), 2.65-2.46 (m, 2H), 2.45-1.95 (m, 7H), 1.80-0.81 (m, 34H), 0.80-0.65 (m, 2H), 0.62 (s, 3H).

Synthesis of Compound 4. C1 (60 mg, 0.094 mmol) was dissolved in TBAF (3 mL) and the reaction was stirred at 70° C. for 3 hrs. The reaction was quenched with saturated $NH_4Cl$ solution (10 mL) and extracted with EtOAc (2×10 mL). The combined organic phase was dried over $Na_2SO_4$, filtered, concentrated and purified by combi-flash (0-20% of EtOAc in PE) to give Compound 4 (10 mg, 27%) as a solid.

$^1$H NMR (400 MHz, $CDCl_3$) δ 5.35-5.30 (m, 1H), 3.55-3.45 (m, 1H), 2.70-2.60 (m, 2H), 2.30-1.95 (m, 5H), 1.94-1.58 (m, 7H), 1.56-1.05 (m, 17H), 1.04-0.75 (m, 6H), 0.65 (s, 3H).

LCMS Rt=1.227 min in 2.0 min chromatography, 10-80 AB, purity 100%, MS ESI calcd. for $C_{26}H_{41}O_2$ [M+H—$H_2O$]$^+$ 385, found 385.

Example 4. Synthesis of Compound 5

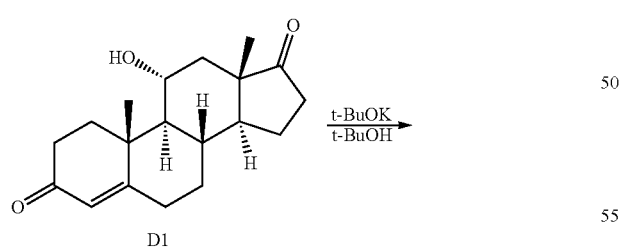

D1

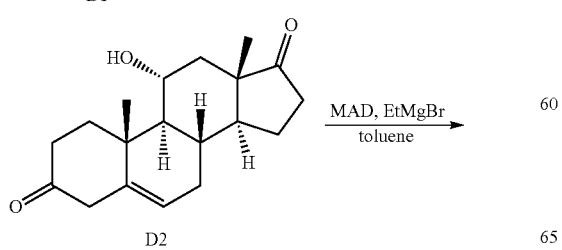

D2

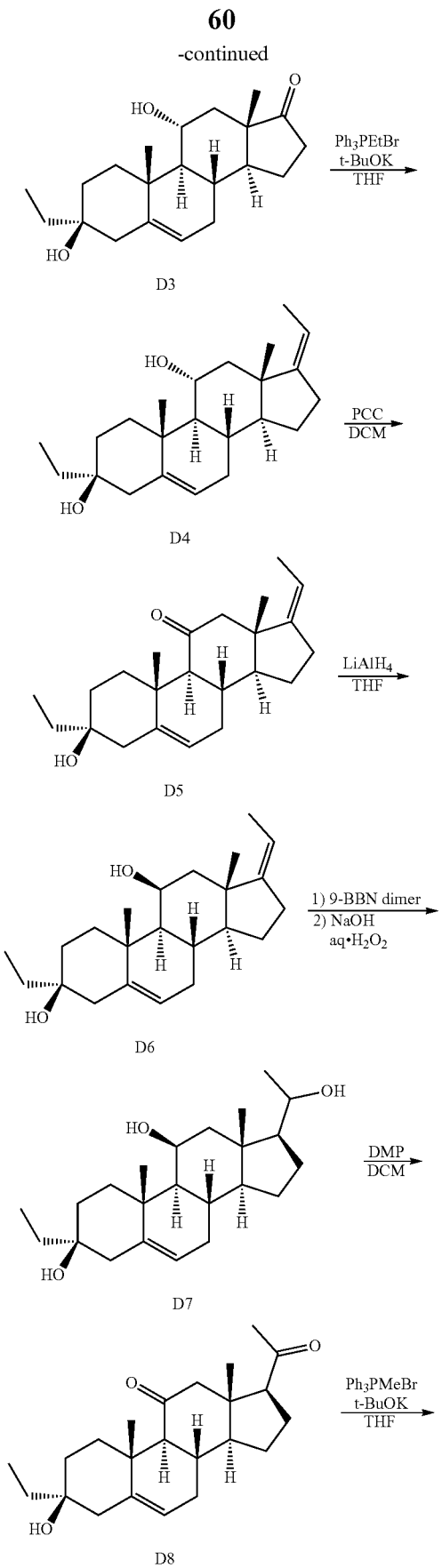

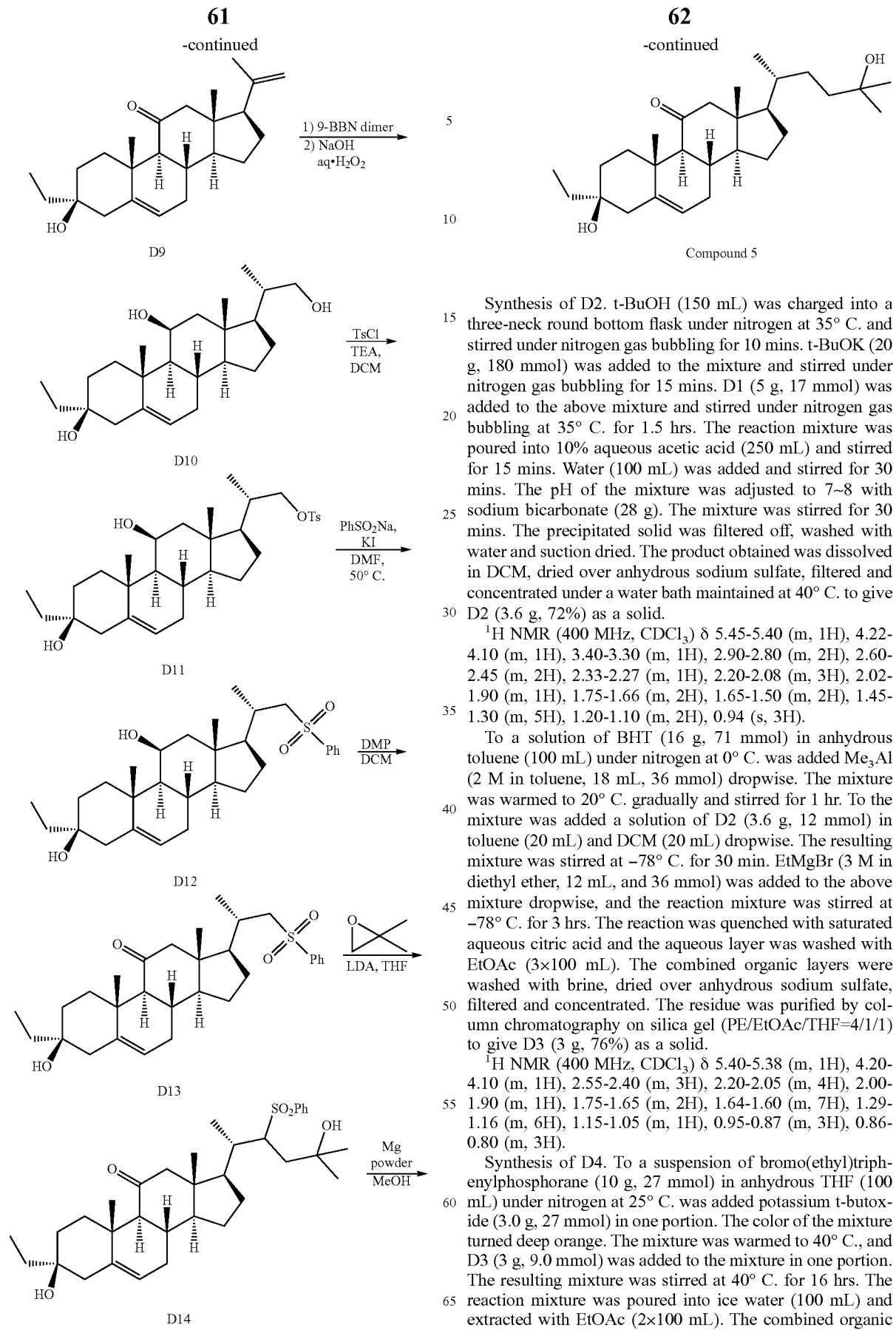

Synthesis of D2. t-BuOH (150 mL) was charged into a three-neck round bottom flask under nitrogen at 35° C. and stirred under nitrogen gas bubbling for 10 mins. t-BuOK (20 g, 180 mmol) was added to the mixture and stirred under nitrogen gas bubbling for 15 mins. D1 (5 g, 17 mmol) was added to the above mixture and stirred under nitrogen gas bubbling at 35° C. for 1.5 hrs. The reaction mixture was poured into 10% aqueous acetic acid (250 mL) and stirred for 15 mins. Water (100 mL) was added and stirred for 30 mins. The pH of the mixture was adjusted to 7~8 with sodium bicarbonate (28 g). The mixture was stirred for 30 mins. The precipitated solid was filtered off, washed with water and suction dried. The product obtained was dissolved in DCM, dried over anhydrous sodium sulfate, filtered and concentrated under a water bath maintained at 40° C. to give D2 (3.6 g, 72%) as a solid.

$^1$H NMR (400 MHz, CDCl$_3$) δ 5.45-5.40 (m, 1H), 4.22-4.10 (m, 1H), 3.40-3.30 (m, 1H), 2.90-2.80 (m, 2H), 2.60-2.45 (m, 2H), 2.33-2.27 (m, 1H), 2.20-2.08 (m, 3H), 2.02-1.90 (m, 1H), 1.75-1.66 (m, 2H), 1.65-1.50 (m, 2H), 1.45-1.30 (m, 5H), 1.20-1.10 (m, 2H), 0.94 (s, 3H).

To a solution of BHT (16 g, 71 mmol) in anhydrous toluene (100 mL) under nitrogen at 0° C. was added Me$_3$Al (2 M in toluene, 18 mL, 36 mmol) dropwise. The mixture was warmed to 20° C. gradually and stirred for 1 hr. To the mixture was added a solution of D2 (3.6 g, 12 mmol) in toluene (20 mL) and DCM (20 mL) dropwise. The resulting mixture was stirred at −78° C. for 30 min. EtMgBr (3 M in diethyl ether, 12 mL, and 36 mmol) was added to the above mixture dropwise, and the reaction mixture was stirred at −78° C. for 3 hrs. The reaction was quenched with saturated aqueous citric acid and the aqueous layer was washed with EtOAc (3×100 mL). The combined organic layers were washed with brine, dried over anhydrous sodium sulfate, filtered and concentrated. The residue was purified by column chromatography on silica gel (PE/EtOAc/THF=4/1/1) to give D3 (3 g, 76%) as a solid.

$^1$H NMR (400 MHz, CDCl$_3$) δ 5.40-5.38 (m, 1H), 4.20-4.10 (m, 1H), 2.55-2.40 (m, 3H), 2.20-2.05 (m, 4H), 2.00-1.90 (m, 1H), 1.75-1.65 (m, 2H), 1.64-1.60 (m, 7H), 1.29-1.16 (m, 6H), 1.15-1.05 (m, 1H), 0.95-0.87 (m, 3H), 0.86-0.80 (m, 3H).

Synthesis of D4. To a suspension of bromo(ethyl)triphenylphosphorane (10 g, 27 mmol) in anhydrous THF (100 mL) under nitrogen at 25° C. was added potassium t-butoxide (3.0 g, 27 mmol) in one portion. The color of the mixture turned deep orange. The mixture was warmed to 40° C., and D3 (3 g, 9.0 mmol) was added to the mixture in one portion. The resulting mixture was stirred at 40° C. for 16 hrs. The reaction mixture was poured into ice water (100 mL) and extracted with EtOAc (2×100 mL). The combined organic layers were dried over anhydrous sodium sulfate, filtered and concentrated. The residue was purified by column chromatography on silica gel (PE/EtOAc=8/1) to give D4 (2.1 g, 68%) as a solid.

$^1$H NMR (400 MHz, CDCl$_3$) δ5.37-5.35 (m, 1H), 5.20-5.10 (m, 1H), 4.20-4.05 (m, 1H), 2.65-2.57 (m, 1H), 2.45-2.37 (m, 3H), 2.28-2.18 (m, 1H), 2.08-1.98 (m, 2H), 1.70-1.61 (m, 8H), 1.60-1.35 (m, 3H), 1.25-1.10 (m, 7H), 1.08-0.92 (m, 2H), 0.90-0.87 (m, 3H), 0.86-0.80 (m, 3H).

Synthesis of D5. To a solution of D4 (1 g, 2.9 mmol) in DCM (15 mL) was added silica gel (1.4 g) and PCC (1.3 mg, 5.8 mmol) at 25° C. The reaction was stirred at 25° C. for 3 hrs. The reaction was filtered and concentrated in vacuum to give crude product which was purified by combi-flash (0%-12% of EtOAc in PE) to give D5 (960 mg, 97%) as a solid.

$^1$H NMR (400 MHz, CDCl$_3$) δ 5.30-5.26 (m, 1H), 5.24-5.19 (m, 1H), 3.00-2.95 (m, 1H), 2.70-2.60 (m, 1H), 2.55-2.30 (m, 4H), 2.20-2.16 (m, 1H), 2.07-2.01 (m, 1H), 1.90-1.70 (m, 5H), 1.68-1.55 (m, 5H), 1.55-1.25 (m, 4H), 1.22 (s, 3H), 1.00-0.90 (m, 1H), 0.80-0.80 (m, 6H).

Synthesis of D6. To a solution of D5 (870 mg, 2.5 mmol) in THF (30 mL) was added LiAlH$_4$ (190 mg, 5.1 mmol) at 0° C. The reaction was stirred at 20° C. for 20 mins. The reaction was quenched with H$_2$O (2 mL) and adjusted with HCl (20 mL, 1N) until the solution became clear. The mixture was extracted with EtOAc (3×20 mL). The combined organic phase was washed with saturated NaHCO$_3$ (50 mL), dried over Na$_2$SO$_4$, filtered and concentrated in vacuum to give crude product D6 (860 mg) as a solid which was used for next step without further purification.

Synthesis of D7. To a solution of D6 (5.5 g, 16 mmol) in THF (100 mL) was added 9-BBN dimer (7.8 g, 32 mmol) at 15° C. under N$_2$. After stirring at 50° C. for 1 hour, the mixture was cooled to 15° C. NaOH solution (32 mL, 5 M, 160 mmol) was added dropwise below 15° C., followed an addition of H$_2$O$_2$ (18 g, 30%, 160 mmol), during which time, the inner temperature was maintained below 15° C. The mixture was poured into water (1000 mL) and filtered to give crude D7 (10 g) as a solid, which was used in the next step directly.

$^1$H NMR (400 MHz, CDCl$_3$) δ 5.21-5.15 (m, 1H), 4.40-4.29 (m, 1H), 3.77-3.66 (m, 1H), 2.46-2.38 (m, 1H), 2.29-2.12 (m, 1H), 2.09-2.00 (m, 2H), 1.98-1.78 (m, 4H), 1.77-1.68 (m, 2H), 1.62-1.53 (m, 2H), 1.47-1.32 (m, 4H), 1.31-1.27 (m, 4H), 1.26-1.18 (m, 5H), 1.17-1.09 (m, 1H), 1.08-0.99 (m, 3H), 0.97-0.89 (m, 3H), 0.88-0.82 (m, 3H).

Synthesis of D8. To a solution of D7 (10 g, 27 mmol) in DCM (500 mL) was added DMP (23 g, 55 mmol). After stirring at 15° C. for 10 min, the reaction mixture was quenched with saturated NaHCO$_3$ solution (500 mL) until the pH of the aqueous layer became about 9. The mixture was filtered. The DCM layer was separated and the aqueous phase was washed with DCM (200 mL). The combined organic layers were washed with saturated Na$_2$S$_2$O$_3$ aqueous (3×400 mL), saturated NaHCO$_3$ (400 mL), and brine (400 mL). The solution was then dried over Na$_2$SO$_4$, filtered and concentrated to give a crude, which was purified by combi-flash (0-30% of EtOAc in PE) to give D8 (3.5 g, 35%) as a solid.

$^1$H NMR (400 MHz, CDCl$_3$) δ 5.30-5.25 (m, 1H), 2.75-2.65 (m, 2H), 2.63-2.55 (m, 1H), 2.48-2.42 (m, 1H), 2.39-2.31 (m, 1H), 2.29-2.18 (m, 1H), 2.15-2.08 (m, 4H), 2.06-2.02 (m, 1H), 1.89-1.72 (m, 6H), 1.67-1.60 (m, 2H), 1.46-1.30 (m, 4H), 1.21 (s, 3H), 1.03-0.93 (m, 1H), 0.88-0.80 (m, 3H), 0.60 (s, 3H).

Synthesis of D9. To a suspension of MePh$_3$PBr (6.2 g, 18 mmol) in THF (100 mL) was added t-BuOK (2.0 g, 18 mmol). After stirring at 40° C. for 10 minutes, the Wittig reagent was slowly added dropwise to a solution of D8 (3.2 g, 8.8 mmol) in THF (50 mL) at 15° C. After addition, the mixture was quenched with NH$_4$Cl (200 mL) and extracted with EtOAc (3×50 mL). The combined organic phase was dried over Na$_2$SO$_4$, filtered, concentrated and purified by combi-flash (0-25% of EtOAc in PE) to give D9 (2.9 g, 92%) as a solid.

$^1$H NMR (400 MHz, CDCl$_3$) δ 5.36-5.18 (m, 1H), 4.89 (s, 1H), 4.71 (s, 1H), 2.65-2.46 (m, 2H), 2.40-2.31 (m, 1H), 2.30-2.20 (m, 2H), 2.16-1.98 (m, 2H), 1.91-1.98 (m, 4H), 1.76-1.62 (m, 5H), 1.51-1.32 (m, 4H), 1.31-1.13 (m, 6H), 1.04-0.93 (m, 1H), 0.88-0.82 (m, 3H), 0.55 (s, 3H).

Synthesis of D10. To a mixture of D9 (3.2 g, 9.0 mmol) in THF (80 mL) was added 9-BBN dimer (4.4 g, 18 mmol) at 15° C. under N$_2$. After stirring at 50° C. for 1 hour, the mixture was cooled to 15° C. NaOH solution (18 mL, 5 M, 90 mmol) was added dropwise below 15° C., followed by an addition of H$_2$O$_2$ (10 g, 30%, 90 mmol) below 15° C. The mixture was extracted with EtOAc (2×50 mL). The combined organic phase was washed with saturated Na$_2$S$_2$O$_3$ (3×100 mL), dried over Na$_2$SO$_4$, filtered and concentrated to give crude D10 (6 g) as a solid, which was used in next step directly.

$^1$H NMR (400 MHz, CDCl$_3$) δ 5.24-5.09 (m, 1H), 4.44-4.28 (m, 1H), 3.73-3.59 (m, 1H), 3.44-3.30 (m, 1H), 2.48-2.32 (m, 1H), 2.22-2.08 (m, 2H), 2.06-2.00 (m, 1H), 1.95-1.77 (m, 4H), 1.75-1.63 (m, 4H), 1.50-1.33 (m, 5H), 1.29-1.13 (m, 8H), 1.09-1.00 (m, 5H), 0.94 (s, 3H), 0.89-0.82 (m, 3H).

Synthesis of D11. To a solution of D10 (6 g, 16 mmol) in DCM (200 L) was added 1-methyl-1H-imidazole (2.0 g, 24 mmol) and TEA (3.2 g, 32 mmol) at 20° C. TsCl (6.1 g, 32 mmol) was added into the above solution. After stirring at 20° C. for 2 hours, the mixture was washed with water (2×100 mL), dried over Na$_2$SO$_4$, filtered, concentrated and purified by combi-flash (0-40% of EtOAc in PE) to give D11 (2.8 g, 59% yield for 2 steps) as a solid.

$^1$H NMR (400 MHz, CDCl$_3$) δ 7.81-7.74 (m, 2H), 7.38-7.31 (m, 2H), 5.21-5.14 (m, 1H), 4.35-4.29 (m, 1H), 3.97-3.92 (m, 1H), 3.84-3.76 (m, 1H), 2.49-2.35 (m, 4H), 2.18-2.00 (m, 3H), 1.91-1.73 (m, 3H), 1.72-1.58 (m, 5H), 1.50-1.31 (m, 4H), 1.28 (s, 3H), 1.26-1.09 (m, 5H), 1.05-0.92 (m, 5H), 0.91-0.80 (m, 6H).

Synthesis of D12. To a solution of D11 (2.8 g, 5.3 mmol) in DMF (20 mL) was added KI (4.4 g, 26 mol) at 15° C. After stirring at 60° C. for 1 hour, sodium benzenesulfinate (5.2 g, 32 mmol) was added in one portion and the mixture was heated at 60° C. for 2 h. The mixture was then quenched with saturated NH$_4$Cl (50 mL) and extracted with EtOAc (2×30 mL). The combined organic phase was washed with LiCl (3% in water, 2×50 mL), dried over Na$_2$SO$_4$, filtered, concentrated and purified by combi-flash (0-30% of EtOAc in PE) to give D12 (1.6 g, 61%) as a solid.

$^1$H NMR (400 MHz, CDCl$_3$) δ 7.95-7.88 (m, 2H), 7.67-7.54 (m, 3H), 5.19-5.14 (m, 1H), 4.34-4.27 (m, 1H), 3.17-3.08 (m, 1H), 2.89-2.80 (m, 1H), 2.643-2.36 (m, 1H), 2.16-2.06 (m, 3H), 2.04-1.99 (m, 1H), 1.92-1.81 (m, 2H), 1.76-1.56 (m, 4H), 1.48-1.30 (m, 3H), 1.27 (s, 3H), 1.26-1.05 (m, 9H), 1.04-0.94 (m, 3H), 0.88 (s, 3H), 0.86-0.82 (m, 3H).

Synthesis of D13. To a solution of D12 (1.2 g, 2.4 mmol) in DCM (30 mL) was added DMP (2.0 g, 4.8 mmol). The reaction mixture was stirred at 15° C. for 10 min. The reaction mixture was then quenched with saturated NaHCO$_3$ aqueous (50 mL) until pH of the aqueous layer became about 9 and then filtered. The organic layer was separated and the aqueous phase was washed with DCM (20 mL). The combined organic phase was washed with saturated $Na_2S_2O_3$ aqueous (3×40 mL), saturated $NaHCO_3$ (40 mL), brine (40 mL), dried over $Na_2SO_4$, filtered and concentrated to give crude D13 (1.1 g, 92%) as a solid.

$^1$H NMR (400 MHz, $CDCl_3$) δ 7.95-7.88 (m, 2H), 7.70-7.54 (m, 3H), 5.29-5.24 (m, 1H), 3.16-3.06 (m, 1H), 2.92-2.83 (m, 1H), 2.65-2.51 (m, 2H), 2.38-2.30 (m, 1H), 2.25-2.16 (m, 1H), 2.14-1.98 (m, 3H), 1.95-1.85 (m, 1H), 1.82-1.58 (m, 7H), 1.50-1.34 (m, 3H), 1.27-1.16 (m, 9H), 1.01-0.91 (m, 1H), 0.87-0.80 (m, 3H), 0.64 (s, 3H).

Synthesis of D14. To a solution of diisopropylamine (160 mg, 1.60 mmol) in THF (0.5 mL) was added n-BuLi (0.56 mL, 2.5 M in hexane, 1.40 mmol) at −70° C. under $N_2$. The mixture was then stirred at 15° C. for 10 minutes. A solution of D13 (200 mg, 0.40 mmol) in THF (1.5 mL) was added at −70° C. After stirring at −70° C. for 1 h, 2,2-dimethyloxirane (43 mg, 0.60 mmol) was added. The mixture was stirred at −70° C. for another 1 h, after which time the mixture was warmed to 15° C. and stirred for 16 hrs. The mixture was quenched with $NH_4Cl$ (30 mL, sat. aq.) and extracted with EtOAc (2×20 mL). The organic layer was separated, dried over $Na_2SO_4$, filtered, and concentrated to give D14 (200 mg, crude) as a solid, which was used for the next step directly.

Synthesis of Compound 5. To a solution of D14 (200 mg, 0.35 mmol) in MeOH (30 mL) was added $NiCl_2$ (8.8 mg, 0.070 mmol) and Mg powder (340 mg, 14 mmol) at 65° C. in one portion. After stirring at 65° C. for 10 minutes, another batch of Mg powder (170 mg, 7 mmol) was added in one portion. The mixture was stirred at 65° C. for another 10 minutes, then quenched with HCl (20 mL, 2N) until the reaction became clear and extracted with EtOAc (3×10 mL). The combined organic layer was washed with sat. $NH_4Cl$ (30 mL), dried over $Na_2SO_4$, filtered, concentrated and purified by silica gel chromatography (0-15% of EtOAc in PE) to give impure Compound 5 (30 mg, 20%) as a white solid, which was further separated by SFC (column: OD (250 mm*30 mm, 5 um)), gradient: 40-40% B (A=0.05% $NH_3/H_2O$, B=MeOH), flow rate: 50 mL/min) to give pure Compound 5 (10 mg, 7%) as a solid.

$^1$H NMR (400 MHz, $CDCl_3$) δ 5.31-5.25 (m, 1H), 2.67-2.52 (m, 2H), 2.38-2.32 (m, 1H), 2.25-2.18 (m, 1H), 2.15-1.94 (m, 3H), 1.87-1.55 (m, 8H), 1.54-1.27 (m, 8H), 1.26-1.21 (m, 4H), 1.20-1.11 (m, 8H), 1.03-0.88 (m, 4H), 0.87-0.81 (m, 3H), 0.65 (s, 3H).

LCMS Rt=1.111 min in 2.0 min chromatography, 30-90AB_E, purity 100%, MS ESI calcd. for $C_{28}H_{45}O_2$ $[M+H-H_2O]^+$ 413, found 413.

Example 5. Synthesis of Compound 6

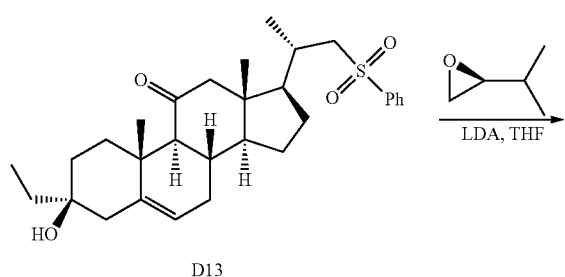

D13

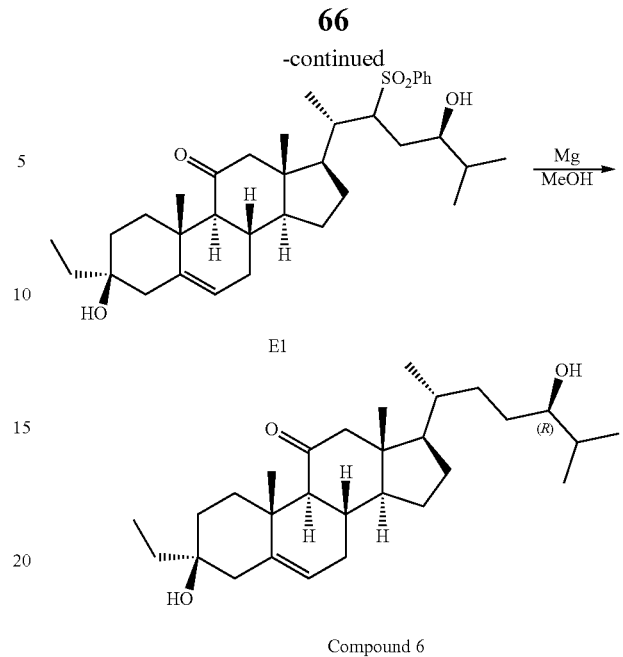

E1

Compound 6

Synthesis of E1. To a solution of diisopropylamine (160 mg, 1.60 mmol) in THF (0.5 mL) was added n-BuLi (0.56 mL, 2.5 M in hexane, 1.4 mmol) at −70° C. under $N_2$. The mixture was then stirred at 15° C. for 10 minutes. A solution of D13 (200 mg, 0.40 mmol) in THF (1.5 mL) was added at −70° C. After stirring at −70° C. for 1 h, (S)-2-isopropyloxirane (52 mg, 0.60 mmol) was added at −70° C. The mixture was stirred at −70° C. for another 1 h, warmed to 15° C. and stirred for 16 hrs. The reaction mixture was quenched with saturated $NH_4Cl$ (50 mL, aq.) and extracted with EtOAc (2×30 mL). The organic layer was separated, dried over $Na_2SO_4$, filtered, and concentrated to give E1 (200 mg, crude) as a solid, which was used for next step directly.

Synthesis of Compound 6. To a solution of E1 (250 mg, 0.43 mmol) in MeOH (30 mL) was added $NiCl_2$ (11 mg, 0.085 mmol) and Mg powder (410 mg, 17 mmol) at 65° C. in one portion. The mixture was stirred at 65° C. for 10 minutes. Then another batch of Mg powder (200 mg, 8.5 mmol) was added at 65° C. in one portion. The mixture was stirred at 65° C. for another 10 minutes. The mixture was quenched with HCl (50 mL, 2N) until the reaction became clear. The mixture was the washed with EtOAc (3×20 mL). The combined organic layer was washed with sat. $NH_4Cl$ (50 mL), dried over $Na_2SO_4$, filtered, concentrated and purified by silica gel chromatography (0-15% of EtOAc in PE) to give impure Compound 6 (40 mg, 21%), which was further purified by SFC ((column: AD (250 mm*30 mm, 10 um), gradient: 35-35% B (A=0.05% $NH_3/H_2O$, B=MeOH), flow rate: 60 mL/min)) to give pure Compound 6 (8 mg, 4%) as a solid.

$^1$H NMR (400 MHz, $CDCl_3$) δ 5.31-5.26 (m, 1H), 3.36-3.28 (m, 1H), 2.69-2.55 (m, 2H), 2.39-2.31 (m, 1H), 2.25-2.18 (m, 1H), 2.14-1.94 (m, 3H), 1.86-1.70 (m, 4H), 1.69-1.58 (m, 4H), 1.47-1.33 (m, 8H), 1.29-1.13 (m, 8H), 0.94-0.88 (m, 9H), 0.86-0.82 (m, 3H), 0.65 (s, 3H).

LCMS Rt=1.182 min in 2.0 min chromatography, 30-90AB_E, purity 100%, MS ESI calcd. for $C_{29}H_{47}O_2$ $[M+H-H_2O]^+$ 427, found 427.

Example 6. Synthesis of Compound 7

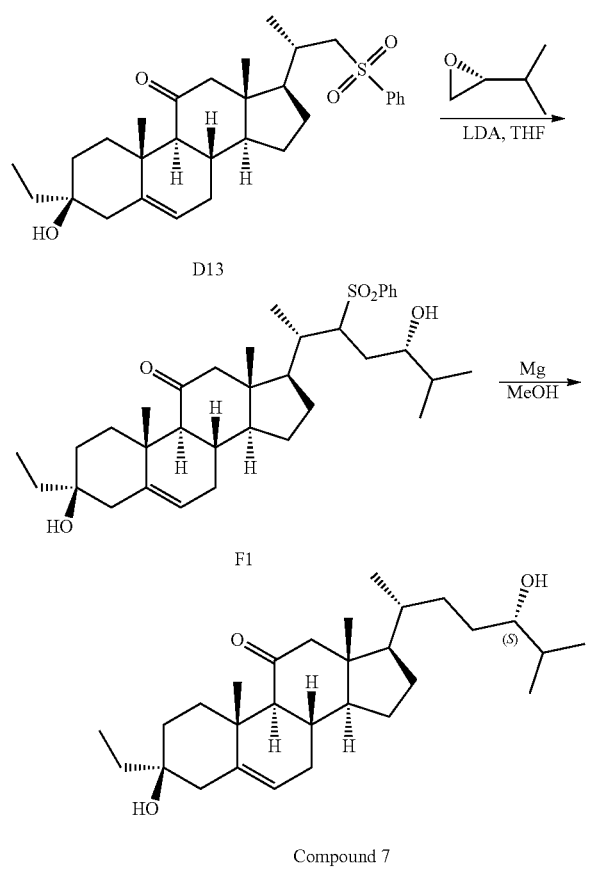

Synthesis of F1. To a solution of diisopropylamine (160 mg, 1.60 mmol) in THF (0.5 mL) was added n-BuLi (0.56 mL, 2.5 M in hexane, 1.40 mmol) at −70° C. under $N_2$. The resulting mixture was stirred at 15° C. for 10 minutes. A solution of D13 (200 mg, 0.40 mmol) in THF (1.5 mL) was added at −70° C. After stirring at −70° C. for 1 h, (R)-2-isopropyloxirane (52 mg, 0.60 mmol) was added at −70° C. The mixture was stirred at −70° C. for another 1 h, warmed to 15° C. and stirred for 16 hrs. The reaction mixture was quenched with $NH_4Cl$ (50 mL, sat. aq.) and extracted with EtOAc (2×30 mL). The organic layer was separated, dried over $Na_2SO_4$, filtered, and concentrated to give F1 (200 mg, crude) as a solid, which was used for next step without further purification.

Synthesis of Compound 7. To a solution of F1 (250 mg, 0.43 mmol) in MeOH (30 mL) was added $NiCl_2$ (11 mg, 0.085 mmol) and Mg powder (410 mg, 17 mmol) at 65° C. in one portion. After stirring at 65° C. for 10 minutes, another batch of Mg powder (200 mg, 8.5 mmol) was added at 65° C. in one portion and stirred at 65° C. for another 10 minutes. The reaction mixture was quenched with HCl (50 mL, 2N) until the reaction became clear and extracted with EtOAc (3×20 mL). The combined organic layer was washed with saturated $NH_4Cl$ (50 mL), dried over $Na_2SO_4$, filtered, concentrated and purified by silica gel chromatography (0-15% of EtOAc in PE) to give impure Compound 7 (80 mg, 42%), which was further purified by SFC ((column: AD (250 mm*30 mm, 10 um), gradient: 35-35% B (A=0.05% NH3/H2O, B=MeOH), flow rate: 60 mL/min)) to give pure Compound 7 (38 mg, 20%) as a solid.

$^1$H NMR (400 MHz, $CDCl_3$) δ 5.32-5.25 (m, 1H), 3.36-3.25 (m, 1H), 2.70-2.53 (m, 2H), 2.39-2.31 (m, 1H), 2.25-2.18 (m, 1H), 2.14-1.94 (m, 3H), 1.86-1.70 (m, 4H), 1.69-1.56 (m, 5H), 1.53-1.31 (m, 6H), 1.29-1.16 (m, 7H), 1.08-0.94 (m, 2H), 0.93-0.88 (m, 9H), 0.87-0.81 (m, 3H), 0.65 (s, 3H).

LCMS Rt=1.179 min in 2.0 min chromatography, 30-90AB_E, purity 100%, MS ESI calcd. for $C_{29}H_{47}O_2$ $[M+H-H_2O]^+$ 427, found 427.

Example 7. Synthesis of Compound 8

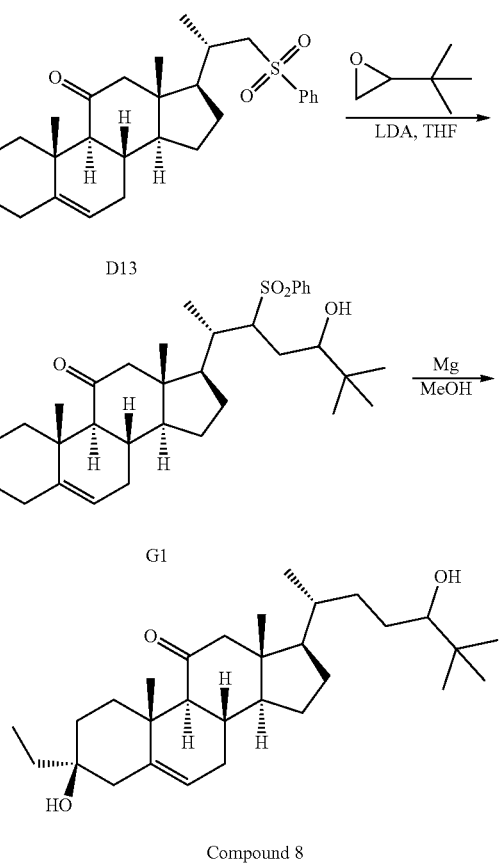

Synthesis of G1. To a solution of diisopropylamine (320 mg, 3.2 mmol) in THF (0.5 mL) was added n-BuLi (1.1 mL, 2.5 M in hexane, 2.8 mmol) at −70° C. under $N_2$. After addition, the mixture was stirred at 15° C. for 10 minutes. A solution of D13 (400 mg, 0.80 mmol) in THF (3 mL) was added at −70° C. After stirring at −70° C. for 1 h, 2-(tert-butyl)oxirane (120 mg, 1.2 mmol) was added at −70° C. The mixture was stirred at −70° C. for another 1 h, after which time the mixture was warmed to 15° C. and stirred for 16 hrs. The reaction mixture was quenched with saturated $NH_4Cl$ (30 mL) and extracted with EtOAc (2×15 mL). The combined organic phase was dried over $Na_2SO_4$, filtered, and concentrated to give G1 (400 mg, crude) as a solid, which was used for the next step directly.

Synthesis of Compound 8. To a solution of G1 (400 mg, 0.67 mmol) in MeOH (40 mL) was added $NiCl_2$ (17 mg, 0.13 mmol) and Mg powder (640 mg, 27 mmol) at 65° C. in one portion. After stirring at 65° C. for 10 minutes, another batch of Mg powder (320 mg, 13 mmol) was added at 65° C. in one portion. After stirring at 65° C. for another 10 minutes, the mixture was quenched with HCl (20 mL, 2N) until the reaction became clear and extracted with EtOAc (3×15 mL). The combined organic layer was washed with sat. NH₄Cl (50 mL), dried over Na₂SO₄, filtered, concentrated and purified by silica gel chromatography (0-15% of EtOAc in PE) to give impure Compound 8 (80 mg, 26%) as a solid.

Example 8. Preparation of Compound 9 and Compound 10

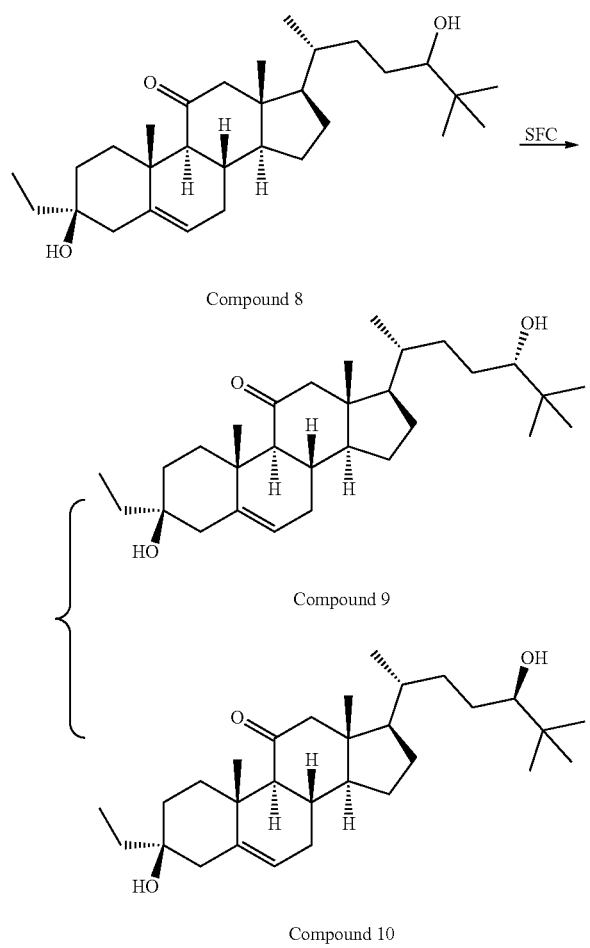

80 mg of Compound 8 was separated by SFC ((column: AD (250 mm*30 mm, 5 um), gradient: 35-35% B (A=0.05% NH₃/H₂O, B=MeOH), flow rate: 60 mL/min)) to give Compound 9 (Peak 1, 21 mg, 26%) and Compound 10 (Peak 2, 13 mg, 16%) as a solid.

SFC of Compound 8

SFC Peak 1: Rt=5.107 min and Peak 2 Rt=6.110 min in 10 min chromatography, AD_3_EtOH_DEA_5_40_25ML ("Column: Chiralpak AD-3 150×4.6 mm I.D., 3 um Mobile phase: A: CO₂ B: ethanol (0.05% DEA) Gradient: from 5% to 40% of B in 5 min and hold 40% for 2.5 min, then 5% of B for 2.5 min Flow rate: 2.5 mL/min Column temp.: 35° C.").

Compound 9 Data $^1$H NMR (400 MHz, CDCl₃) δ 5.30-5.25 (m, 1H), 3.14-3.04 (m, 1H), 2.68-2.54 (m, 2H), 2.38-2.31 (m, 1H), 2.26-2.19 (m, 1H), 2.14-1.93 (m, 3H), 1.84-1.69 (m, 5H), 1.68-1.58 (m, 4H), 1.47-1.35 (m, 4H), 1.34-1.23 (m, 3H), 1.22 (s, 3H), 1.20-1.14 (m, 1H), 1.11-0.95 (m, 3H), 0.94-0.87 (m, 12H), 0.86-0.81 (m, 3H), 0.65 (s, 3H), LCMS Rt=1.216 min in 2.0 min chromatography, 30-90AB_E, purity 100%, MS ESI calcd. for C₃₀H₄₉O₂ [M+H—H₂O]⁺ 441, found 441.

SFC Rt=5.096 min in 10 min chromatography, AD_3_EtOH_DEA_5_40_25ML, 100% de.

The absolute stereochemistry of Compound 9 was determined by X-ray crystallography. The structure of Compound 10 was subsequently inferred from the X-ray crystal structure of Compound 9.

Compound 10 Data $^1$H NMR (400 MHz, CDCl₃) δ 5.30-5.25 (m, 1H), 3.17-3.11 (m, 1H), 2.68-2.54 (m, 2H), 2.38-2.31 (m, 1H), 2.26-2.19 (m, 1H), 2.14-1.97 (m, 3H), 1.86-1.71 (m, 4H), 1.68-1.58 (m, 3H), 1.50-1.34 (m, 7H), 1.32-1.24 (m, 4H), 1.23-1.17 (m, 4H), 1.02-0.94 (m, 1H), 0.93-0.87 (m, 12H), 0.86-0.82 (m, 3H), 0.66 (s, 3H).

LCMS Rt=1.211 min in 2.0 min chromatography, 30-90AB_E, purity 100%, MS ESI calcd. for C₃₀H₄₉O₂ [M+H—H₂O]⁺ 441, found 441.

SFC Rt=6.049 min in 10 min chromatography, AD_3_EtOH_DEA_5_40_25ML, 100% de.

Example 9. Syntheses of Compound 11

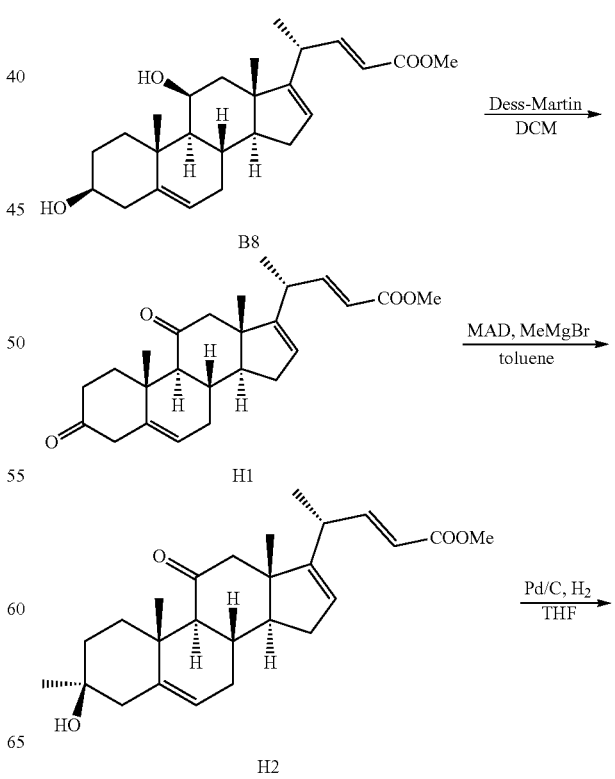

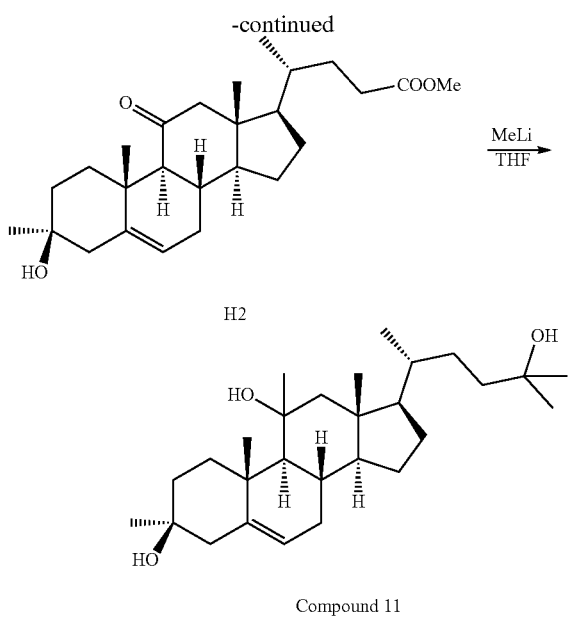

Compound 11

Synthesis of H1. To a solution of B8 (200 mg, 0.5 mmol) in DCM (20 mL) was added DMP (840 mg, 2 mmol). After stirring at 15° C. for 2 hrs, the mixture was filtered and the filter cake was washed with DCM (2×10 mL). The filtrated was quenched with saturated $Na_2SO_3$ and $NaHCO_3$ (50 mL, v/v=1/1) and the resulting solution was washed with DCM (2×10 mL) to give H1 (220 mg, crude) as an oil, which was used directly.

$^1$H NMR (400 MHz, $CDCl_3$) δ 6.91-6.85 (m, 1H), 5.88-5.84 (m, 1H), 5.55-5.50 (m, 1H), 5.40-5.39 (m, 1H), 3.75 (s, 3H), 3.35-3.25 (m, 1H), 3.02-2.82 (m, 3H), 2.60-1.82 (m, 8H), 1.49-1.15 (m, 8H), 0.90-0.72 (m, 5H).

Synthesis of H2. To a solution of 2,6-di-tert-butyl-4-methylphenol (610 mg, 2.8 mmol) in toluene (20 mL) was added $AlMe_3$ (1.40 mL, 2 M in toluene, 2.8 mmol) dropwise at 0° C. After stirring at 15° C. for 1 h, a solution of compound H1 (220 mg, 0.55 mmol) in toluene (5 mL) was added dropwise at −78° C. dropwise under $N_2$. The mixture was stirred at −78° C. for 1 h and MeMgBr (0.92 mL, 3 M in ether, 2.8 mmol) was added dropwise at −70° C. The mixture was stirred at −70° C. for another 1 h, quenched with citric acid solution (30 mL) and then extracted with EtOAc (2×15 mL). The combined organic phase was dried, filtered, concentrated and purified by combi-flash (0-25% of EtOAc in PE) to give H2 (90 mg, 39%) as a solid.

$^1$H NMR (400 MHz, $CDCl_3$) δ 6.91-6.85 (m, 1H), 5.84-5.79 (m, 1H), 5.51-5.50 (m, 1H), 5.30-5.29 (m, 1H), 3.72 (s, 3H), 2.98-2.92 (m, 1H), 2.70-2.62 (m, 1H), 2.49-2.05 (m, 6H), 2.04-1.71 (m, 8H), 1.70-1.11 (m, 5H), 1.10-0.91 (m, 1H), 0.90-0.76 (m, 4H), 0.74 (s, 3H).

Synthesis of H3. To a solution of H2 (90 mg, 0.22 mmol) in THF (10 mL) was added Pd/C (wet, 200 mg). The mixture was stirred at 15° C. for 16 hrs under $H_2$ (15 psi). The mixture was filtered and concentrated to give H3 (90 mg, 100%) as an oil.

$^1$H NMR (400 MHz, $CDCl_3$) δ 5.30-5.29 (m, 1H), 3.67 (s, 3H), 2.65-2.62 (m, 1H), 2.39-2.34 (m, 2H), 2.35-2.24 (m, 2H), 2.22-2.20 (m, 1H), 1.99-1.95 (m, 3H), 1.43 (s, 3H), 1.42-1.22 (m, 12H), 1.10 (s, 3H), 0.90-0.89 (m, 6H), 0.65 (s, 3H).

Synthesis of Compound 11. To a solution of H3 (90 mg, 0.22 mmol) in THF (10 mL) was added MeLi (0.68 mL, 1.1 mmol, 1.6 M in THF) under $N_2$. After stirring at 15° C. for 1 h, the mixture was quenched with saturated $NH_4Cl$ (10 mL) and extracted with EtOAc (3×5 mL). The combined organic phase was dried over $Na_2SO_4$, filtered, concentrated and purified by flash column (15% of EtOAc in PE/DCM=2/1) to give 35 mg impure product, which was recrystallized from MeCN (2 mL) for 3 times to give pure Compound 11 (6 mg, 6%) as a solid.

$^1$H NMR (400 MHz, $CDCl_3$) δ 5.30-5.29 (m, 1H), 2.55-2.45 (m, 1H), 2.25-2.15 (m, 1H), 2.10-2.01 (m, 1H), 2.00-1.92 (m, 2H), 1.90-1.71 (m, 4H), 1.70-1.58 (m, 2H), 1.55-1.22 (m, 15H), 1.21-0.98 (m, 15H), 0.97-0.92 (m, 3H), 0.88 (s, 3H).

LCMS Rt=1.079 min in 2.0 min chromatography, 30-90AB_ELSD, purity 100%, MS ESI calcd. for $C_{28}H_{45}O$ $[M+H-2H_2O]^+$ 397, found 397.

TABLE 1

| Compound | NMDA Potentiation | |
|---|---|---|
| | GluN2A PCA IWB Ephys % potentiation at 3 μM | GluN2B PCA IWB Ephys % potentiation at 3 μM |
| Compound 1 | B | B |
| Compound 2 | A | A |
| Compound 3 | A | B |
| Compound 4 | B | B |
| Compound 11 | B | B |

For Table 1, "A" indicates % potentiation up to 100%, and "B" indicates potentiation of >100% as described in the above section entitled "Potentiating effect of positive allosteric modulators (PAM) on the channel."

TABLE 2

| | $EC_{50}$ and $E_{max}$ Data | | | |
|---|---|---|---|---|
| Compound | GluN2A PCA $EC_{50}$ (nM) | GluN2B PCA $EC_{50}$ (nM) | GluN2A PCA $E_{max}$ (%) | GluN2B PCA $E_{max}$ (%) |
| Compound 1 | E | E | I | I |
| Compound 2 | F | E | H | H |
| Compound 3 | G | E | H | I |
| Compound 4 | D | D | I | I |
| Compound 5 | D | D | I | I |
| Compound 6 | C | C | I | I |
| Compound 7 | C | C | I | I |
| Compound 9 | C | C | J | I |
| Compound 10 | C | C | J | I |
| Compound 11 | E | F | I | I |

For Table 2, "C" indicates an $EC_{50}$ of 1 to 100 nM, "D" indicates an $EC_{50}$ of greater than 100 nM up to 500 nM, "E" indicates an $EC_{50}$ greater than 500 nM up to 1 μM; "F" indicates an $EC_{50}$ of greater than 1 μM to 9.999 μM; "G" indicates an $EC_{50}$ greater than or equal to 10 μM, "H" indicates an $E_{Max}$ of up to 100%, and "I" indicates an $E_{max}$ between 100% and 500%, and "J" indicates an $E_{max}$ greater than 500%.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above description, but rather is as set forth in the appended claims. Those of ordinary skill in the art will appreciate that various changes and modifications to this description may be made without departing from the spirit or scope of the present invention, as defined in the following claims.

What is claimed is:

1. A method for treating a CNS-related condition in a subject in need thereof, comprising administering to the subject an effective amount of a compound of Formula (I):

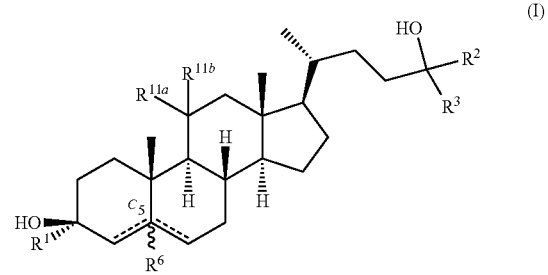

or a pharmaceutically acceptable salt thereof, wherein:
$R^1$ is hydrogen or $C_1$-$C_6$ alkyl;
each of $R^2$ and $R^3$ is independently hydrogen, $C_1$-$C_6$ alkyl, or carbocyclyl, or $R^2$ and $R^3$, together with the carbon atom to which they are attached, form a 3-8 membered ring;
$R^6$ is absent or hydrogen;
$R^{11a}$ is hydrogen or $C_1$-$C_6$ alkyl and $R^{11b}$ is —OH, or $C_1$-$C_6$ alkyl, or $R^{11a}$ and $R^{11b}$ are joined together to form oxo; and
═══ represents a single or double bond, wherein when one ═══ is a double bond, the other ═══ is a single bond; and when one of the ═══ is a double bond, $R^6$ is absent; or
a pharmaceutical composition comprising said compound of Formula (I) or pharmaceutically acceptable salt thereof, and a pharmaceutically acceptable carrier;
wherein the CNS-related condition is related to NMDA-modulation and is selected from the group consisting of schizophrenia, psychotic disorders, sleep disorder, autism spectrum disorders, multiple sclerosis, cognitive disorders, movement disorders, attention deficit disorder, attention deficit hyperactivity disorder, metabolic encephalopathies, postpartum psychosis, Smith Lemli-Opitz syndrome, and Niemann-Pick C disorder.

2. The method of claim 1, wherein the compound of Formula (I) is a compound of Formula (I-A) or Formula (I-B):

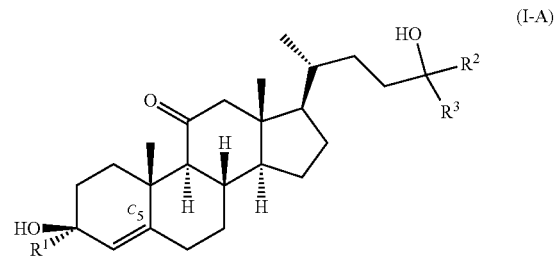

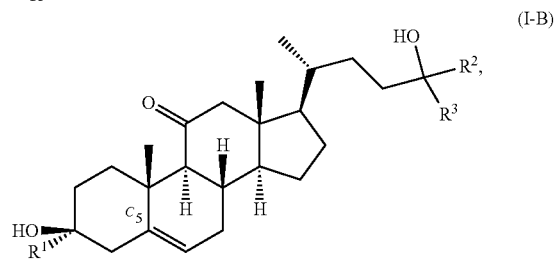

or a pharmaceutically acceptable salt thereof.

3. The method of claim 1, wherein the compound of Formula (I) is a compound of Formula (II-A) or Formula (II-B):

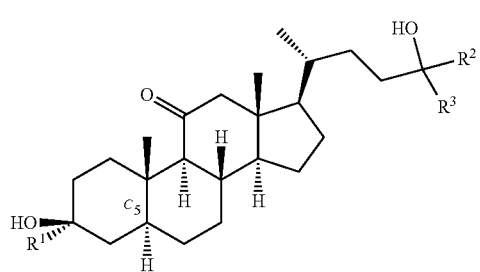
(II-A)
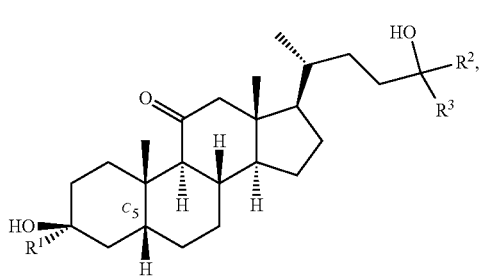
(II-B)
or a pharmaceutically acceptable salt thereof.
4. The method of claim 1, wherein the compound of Formula (I) is selected from the group consisting of:
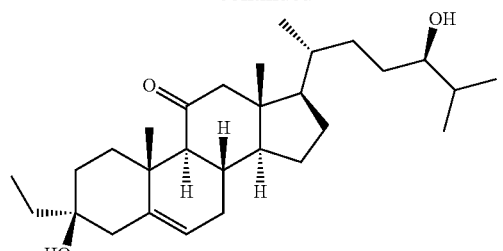
,
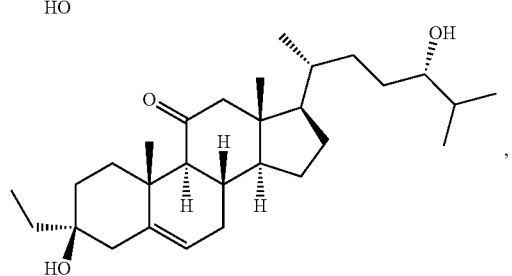
,
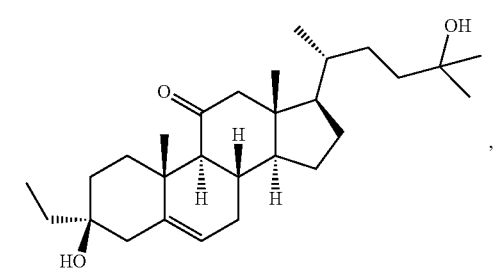
,
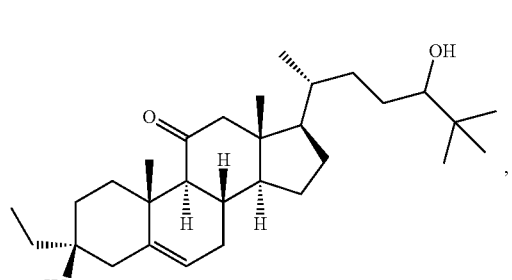
,
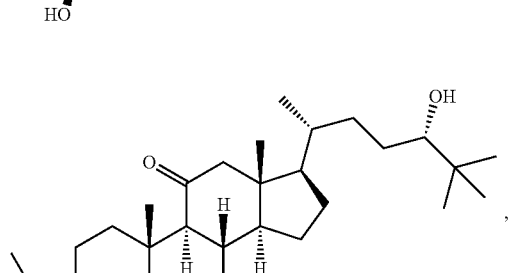
,
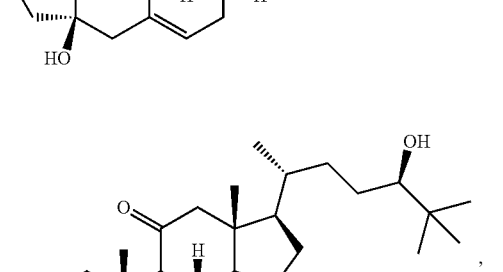
,
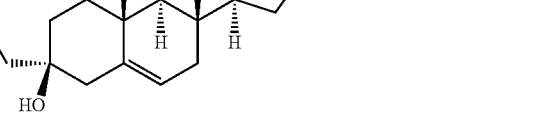
, and

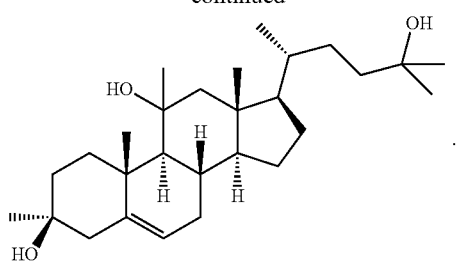
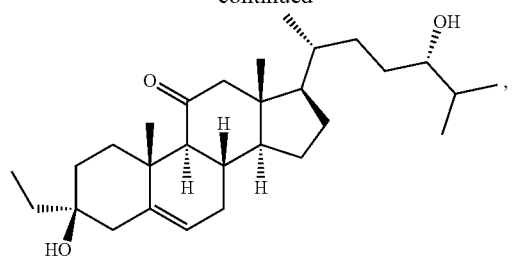
5. The method of claim 1, wherein the compound is a pharmaceutically acceptable salt of a compound selected from the group consisting of:
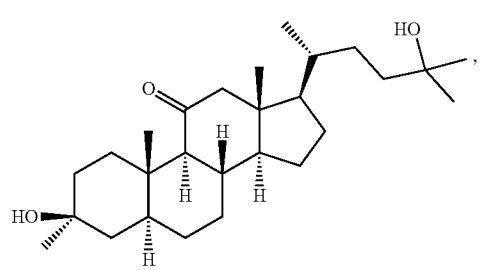
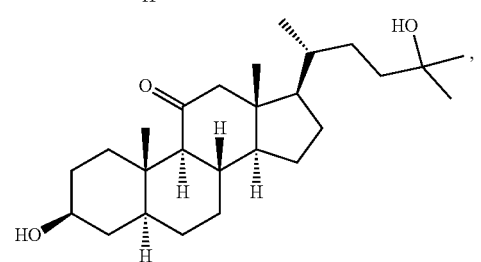
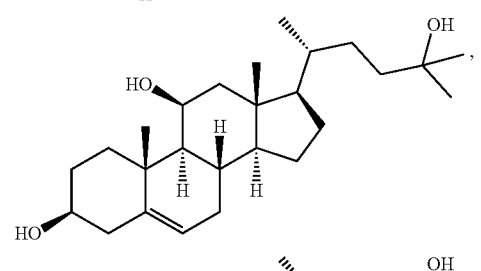
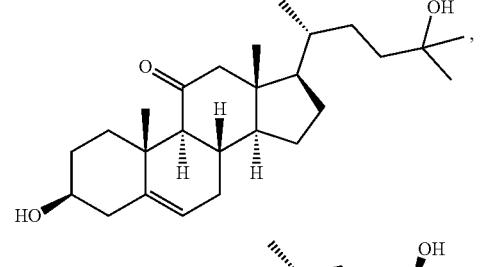
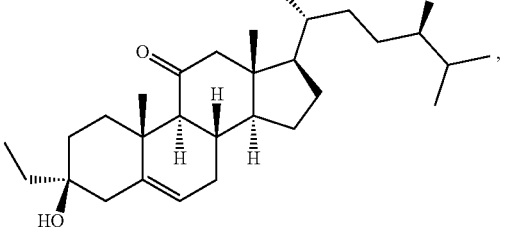
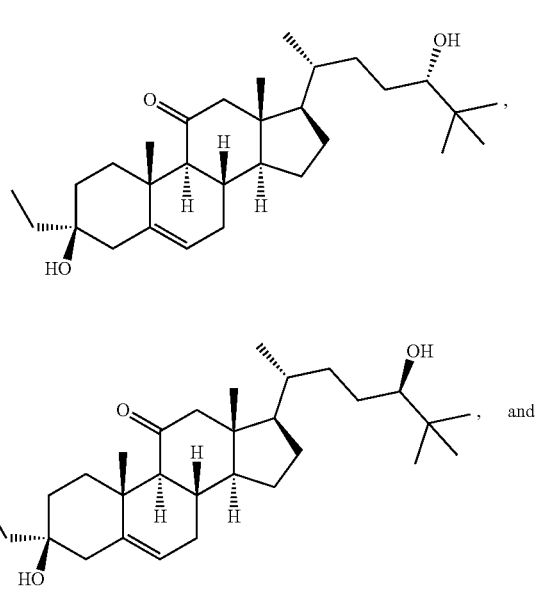
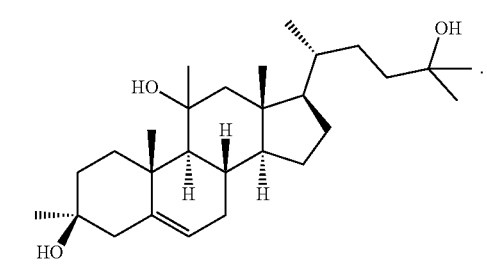

6. The method of claim 1, wherein the compound of Formula (I) is a compound of Formula (III):

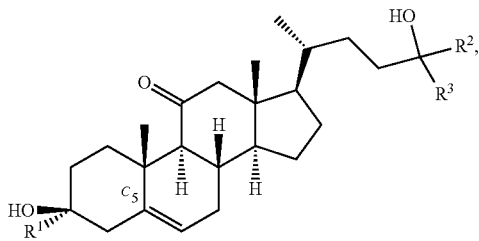

or a pharmaceutically acceptable salt thereof.

7. The method of claim 1, wherein the CNS-related condition is selected from the group consisting of schizophrenia, psychotic disorders, sleep disorder, autism spectrum disorders, multiple sclerosis, movement disorders, attention deficit disorder, attention deficit hyperactivity disorder, metabolic encephalopathies, and postpartum psychosis.

8. The method of claim 7, wherein the CNS-related condition is a movement disorder.

9. The method of claim 8, wherein the movement disorder is selected from Huntington's Disease and Parkinson's disease.

10. The method of claim 1, wherein the CNS-related condition is a cognitive disorder.

11. The method of claim 10, wherein the cognitive disorder is selected from Alzheimer's disease and dementia.

12. The method of claim 11, wherein the dementia is selected from cortical-basal dementia, progressive supranuclear palsy, frontal-temporal dementia, primary progressive aphasia, Parkinson's disease dementia, and Lewy body dementia.

13. The method of claim 1, wherein the CNS-related condition is selected from the group consisting of Smith Lemli-Opitz syndrome, and Niemann-Pick C disorder.

* * * * *